(12) United States Patent
Dickinson et al.

(10) Patent No.: US 6,248,738 B1
(45) Date of Patent: Jun. 19, 2001

(54) ISOQUINOLINES AS UROKINASE INHIBITORS

(75) Inventors: Roger Peter Dickinson; Christopher Gordon Barber; Paul Vincent Fish, all of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/424,497

(22) PCT Filed: Oct. 5, 1998

(86) PCT No.: PCT/EP98/06353

§ 371 Date: May 30, 2000

§ 102(e) Date: May 30, 2000

(87) PCT Pub. No.: WO99/20608

PCT Pub. Date: Apr. 29, 1999

(30) Foreign Application Priority Data

Oct. 16, 1997 (GB) .................................................. 9721964

(51) Int. Cl.$^7$ ...................... C07D 217/22; C07D 401/06; A61K 31/44
(52) U.S. Cl. ................... 514/235.2; 514/253.05; 514/310; 544/128; 544/363; 546/143
(58) Field of Search ..................................... 544/128, 363; 546/143; 514/235.2, 253.05, 310

(56) References Cited

PUBLICATIONS

Rachlin, Journal of Med. Chem, vol. 23, pp. 13–20, 1980.*
Yang. Journal of Med. Chem. vol. 33, pp. 2956–2963, 1990.*

\* cited by examiner

*Primary Examiner*—Zinna Northington Davis
(74) *Attorney, Agent, or Firm*—P. C. Richardson; P. H. Ginsburg; A. L. Koller

(57) ABSTRACT

Compounds of formula (I):

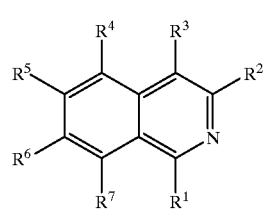

and pharmaceutically acceptable salts thereof, wherein one of $R^1$ and $R^2$ is H and the other is $N=C(NH_2)_2$ or $NHC(=NH)NH_2$, and the other substituents are as defined herein, are urokinase (uPA) inhibitors.

27 Claims, No Drawings

ISOQUINOLINES AS UROKINASE INHIBITORS

This application is the U.S. national stage of PCT/EP98/06353, which has an international filing date of Oct. 5, 1998, and which claims priority from GB 9721964.6, which was filed on Oct. 16, 1997.

This invention relates to certain isoquinolines useful as urokinase inhibitors, and in particular to isoquinolinylguanidines useful as urokinase inhibitors.

Urokinase (urinary-type plasminogen activator or uPA; International Union of Biochemistry classification number EC.3.4.21.31) is a serine protease produced by a large variety of cell types (smooth muscle cells, fibroblasts, endothelial cells, macrophages and tumour cells). It has been implicated as playing a key role in cellular invasion and tissue remodelling. A principal substrate for uPA is plasminogen which is converted by cell surface-bound uPA to yield the serine protease plasmin. Locally produced high plasmin concentrations mediate cell invasion by breaking down the extracellular matrix. Important processes involving cellular invasion and tissue remodelling include wound repair, bone remodelling, angiogenesis, tumour invasiveness and spread of metastases.

Beneficial effects of urokinase inhibitors have been reported using anti-urokinase monoclonal antibodies and certain other known urokinase inhibitors. For instance, anti-urokinase monoclonal antibodies have been reported to block tumour cell invasiveness in vitro (W. Hollas, et al, *Cancer Res.* 51:3690; A. Meissauer, et al, *Exp.Cell Res.* 192:453 (1991); tumour metastases and invasion in vivo (L. Ossowski, *J. Cell Biol.* 107:2437 (1988)); L. Ossowski, et al, *Cancer Res.* 51:274 (1991)) and angiogenesis in vivo (J. A. Jerdan et al, *J.Cell Biol.* 115[3Pt 2]: 402a (1991). Also, Amiloride™, a known urokinase inhibitor of only moderate potency, has been reported to inhibit tumour metastasis in vivo (J. A. Kellen et al, *Anticancer Res.*, 8:1373 (1988)) and angiogenesis/capillary network formation in vitro (M. A. Alliegro et al, *J.Cell Biol.* 115[3Pt 2]:402a).

Conditions of particular interest for treatment by urokinase inhibitors include chronic dermal ulcers (including venous ulcers, diabetic ulcers and pressure sores), which are a major cause of morbidity in the ageing population and cause a significant economic burden on healthcare systems. Chronic dermal ulcers are characterised by excessive uncontrolled proteolytic degradation resulting in ulcer extension, loss of functional matrix molecules (e.g. fibronectin) and retardation of epithelisation and ulcer healing. A number of groups have investigated the enzymes responsible for the excessive degradation in the wound environment, and the role of plasminogen activators has been highlighted (M. C. Stacey et al., *Br. J. Surgery*, 80, 596; M. Palolahti et al., *Exp. Dermatol.*, 2, 29, 1993; A. A. Rogers et al., *Wound Repair and Regen.*, 3, 273, 1995). Normal human skin demonstrates low levels of plasminogen activators which are localised to blood vessels and identified as tissue type plasminogen activator (tPA). In marked contrast, chronic ulcers demonstrate high levels of urokinase type plasminogen activator (uPA) localised diffusely throughout the ulcer periphery and the lesion, and readily detectable in wound fluids.

uPA could affect wound healing in several ways. Plasmin, produced by activation of plasminogen, can produce breakdown of extracellular matrix by both indirect (via activation of matrix metalloproteases) and direct means. Plasmin has been shown to degrade several extracellular matrix components, including gelatin, fibronectin, proteoglycan core proteins as well as its major substrate, fibrin. Whilst activation of matrix metalloproteases (MMPs) can be performed by a number of inflammatory cell proteases (e.g. elastase and cathepsin G), the uPA/plasmin cascade has been implicated in the activation of MMPs in situ, providing a broad capacity for degrading all components of the extracellular matrix. Furthermore, in addition to its effect on production of plasmin, uPA has been shown to catalyse direct cleavage of fibronectin yielding antiproliferative peptides. Thus, over-expression of uPA in the wound environment has the potential to promote uncontrolled matrix degradation and inhibition of tissue repair. Inhibitors of the enzyme thus have the potential to promote healing of chronic wounds.

Several related enzymes such as tPA, which also acts via production of plasmin, play a key role in the fibrinolytic cascade. Because of this it is important that an inhibitor has adequate potency and selectivity for uPA relative to both tPA and plasmin to avoid the possibility of anti-fibrinolytic side effects.

The utility of such potent and selective urokinase inhibitors is highlighted by the broad range of invasive biological processes mediated by urokinase. These processes include, but are not limited to, wound healing, angiogenesis-dependent conditions such as retinopathy, bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

Various aromatic amidines have been reported to inhibit uPA (J. D. Geratz, M. C.-F. Cheng, Thromb. Diathes. haemorrh. (Stuttg.), 33, 230, 1975; J. Stürzebecher, F. Markwardt, Pharmazie, 33, 599, 1978; J. D. Geratz et al., Thromb. Res., 24, 73, 1981). The compounds reported in these publications are generally relatively weak and/or non-selective for uPA relative to other related serine proteases. EP 0 568 289 A2 discloses a series of benzo[b]thiophene-2-carboxamidines with significantly greater potency and selectivity with respect to tPA and plasmin (see also M. J. Towle et al., *Cancer Res.*, 53, 2553, 1993; A. J. Bridges et al., *Bioorg. Med. Chem.*, 1, 403, 1993).

There are few reports of guanidine derivatives as uPA inhibitors. Amiloride™ (see below) is a weak but selective inhibitor of uPA (J.-D. Vassalli, D. Belin, *FEBS Letters*, 214, 187, 1987), and various substituted phenylguanidines are reported to have a similar level of potency (H. Yang et al., *J. Med. Chem.*, 33, 2956, 1990).

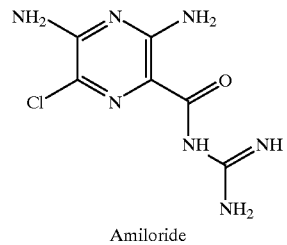

Amiloride

The compounds described herein are potent reversibly-competitive inhibitors of urokinase enzymatic activity, with selectivity for urokinase relative to certain other important proteases, including the fibrinolytic enzymes tissue-type plasminogen activator (tPA) and plasmin.

The selectivity of the instantly-claimed compounds for inhibition of urokinase over inhibition of other proteases such as tPA and plasmin, and the fact that they inhibit reversibly, prevents them from having thrombogenic properties.

Thus, according to the present invention, there is provided an isoquinolinylguanidine derivative of formula (I):

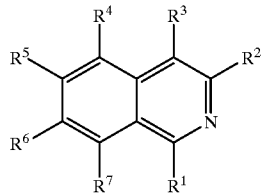

or a pharmaceutically acceptable salt thereof, wherein
one of $R^1$ and $R^2$ is H and the other is $N=C(NH_2)_2$ or $NHC(=NH)NH_2$, $R^3$ is H, halogen, $C_{1-6}$ alkyl optionally substituted by one or more halogen, or $C_{1-6}$ alkoxy optionally substituted by one or more halogen, $R^4$, $R^5$, $R^6$ and $R^7$ are each independently H, OH, halogen, $C_{1-6}$ alkyl optionally substituted by one or more substituents independently selected from halogen or OH, $C_{1-6}$ alkoxy optionally substituted by one or more halogen, CN, $CO(C_{1-6}$ alkyl optionally substituted by one or more halogen), $(C_m$-alkylene$)CO_2R^8$, $(C_n$-alkylene)CN, $O(C_n$-alkylene)CN, $O(C_n$-alkylene)$CO_2R^8$, $(C_m$-alkylene)$CONR^9R^{10}$, $(C_m$-alkylene)$NH^9COR^{10}$, $O(C_n$-alkylene)$CONR^9R^{10}$, $(C_m$-alkylene)$NR^9SO_2R^{11}$, $(C_m$-alkylene)$S(O)_pR^{11}$, $(C_m$-alkylene)$SO_2NR^9R^{10}$, $CH=CHCOR^8$, $CH=CHCONR^9R^{10}$, $CH=CHSO_2R^8$, $CH=CHSO_2NR^9R^{10}$, $CH=CHSO_2$aryl, or a group of formula X-aryl or X-het, or, where two of $R^4$, $R^5$, $R^6$ and $R^7$ are attached to adjacent carbon atoms, they can be taken together to form an $-O(C_n$-alkylene)O-moiety, $R^8$ is H, $C_{1-6}$ alkyl optionally substituted by one or more halogen, or aryl($C_{1-6}$ alkylene), $R^9$ and $R^{10}$ are each independently H, $C_{1-6}$ alkyl optionally substituted by one or more halogen, aryl($C_{1-6}$ alkylene), aryl, heteroaryl or heteroaryl($C_{1-6}$ alkylene), or $R^9$ and $R^{10}$ may be linked together by an alkylene moiety to form, with the atoms to which they are attached, a 4- to 7-membered ring optionally incorporating an additional hetero-group selected from an O or S atom or a $NR^{12}$ group, $R^{11}$ is aryl, heteroaryl, or $C_{1-6}$ alkyl optionally substituted by one or more halogen, $R^{12}$ is H, $C_{1-6}$ alkyl optionally substituted by one or more halogen, or $CO(C_{1-6}$ alkyl optionally substituted by one or more halogen), X is a direct link, $C_n$-alkylene, O, $(C_n$-alkylene)O, $O(C_n$-alkylene), CH(OH), C($C_{1-6}$ alkyl)OH, CO, $S(O)_p(C_m$-alkylene), $(C_m$-alkylene)$S(O)_p$, CH=CH, or C≡C, "aryl" is phenyl or naphthyl optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CON^4R^{15}$, $(C_m$-alkylene)$S(O)_pR^{13}$, $(C_m$-alkylene)$SO_2NR^{14}R^{15}$, $(C_m$-alkylene)$NR^{14}SO_2R^{16}$, $CH=CHSO_2R^{13}$, $CH=CHSO_2NR^{14}R^{15}$, $CH=CHSO_2$aryl$^1$, $CH=CHCOR^{13}$, and $CH=CHCONR^{14}R^{15}$, "heteroaryl" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^5$, $O(C_n$-alkylene)$CONR^{14}R^{15}$, $(C_m$-alkylene)$NR^{14}SO_2R^{16}$, $(C_m$-alkylene)$S(O)_pR^{13}$, $(C_m$-alkylene)$SO_2NR^{14}R^{15}$, $CH=CHCOR^{13}$, $CH=CHCONR^{14}R^{15}$, $CH=CHSO_2R^{13}$, $CH=CHSO_2NR^{14}R^{15}$, or $CH=CHSO_2$aryl$^1$, "het" is an optionally benzo-fused 5- or 6-membered heterocyclic group linked to the "X" moiety by any available atom in the heterocyclic or benzo-ring (if present), which heterocyclic group is selected from dioxolyl, dioxolanyl, furyl, thienyl, pyrrolyl, oxazolyl, oxazinyl, thiazinyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, or a fully unsaturated, partially or fully saturated analogue thereof, such "het" group being optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$NR^{14}SO_2R^{16}$, $(C_m$-alkylene)$S(O)_pR^{13}$, $(C_m$-alkylene)$SO_2NR^{14}R^{15}$, $CH=CHCOR^{13}$, $CH=CHCONR^{14}R^{15}$, $CH=CHSO_2R^{13}$, $CH=CHSO_2NR^{14}R^{15}$, and $CH=CHSO_2$aryl$^1$, "aryl$^1$" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$S(O)_pR^{13}$, $(C_m$-alkylene)$SO_2NR^{14}R^{15}$, $(C_m$-alkylene)$NR^{14}SO_2R^{16}$, $CH=CHSO_2R^{13}$, $CH=CHSO_2NR^{14}R^{15}$, $CH=CHCOR^{13}$, and $CH=CHCONR^{14}R^{15}$, $R^{13}$ is H, $C_{1-6}$ alkyl optionally substituted by one or more halogen, or aryl$^2(C_{1-6}$ alkylene), $R^{14}$ and $R^{15}$ are each independently H, $C_{1-6}$ alkyl optionally substituted by one or more halogen, aryl$^2(C_{1-6}$ alkylene), aryl$^2$, heteroaryl or heteroaryl $^1$(C$_{1-6}$ alkylene), or R$^9$ and R$^{10}$ may be linked together by an alkylene moiety to form, with the atoms to which they are attached, a 4- to 7-membered ring optionally incorporating an additional hetero-group selected from an O or S atom or a NR group, R$^{16}$ is aryl$^2$, heteroaryl$^1$, or C$_{1-6}$ alkyl optionally substituted by one or more halogen, "aryl$^2$" is phenyl or naphthyl optionally substituted by one or more substituents independently selected from halogen, C$_{1-6}$ alkyl optionally substituted by one or more substituents independently selected from halogen or OH, C$_{1-6}$ alkoxy optionally substituted by one or more halogen, CN, O(C$_n$-alkylene)CN, (C$_n$-alkylene)CN, or CO(C$_{1-6}$ alkyl optionally substituted by one or more halogen), "heteroaryl$^1$" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl$^1$" group being optionally substituted by one or more substituents independently selected from halogen, C$_{1-6}$ alkyl optionally substituted by one or more substituents independently selected from halogen or OH, C$_{1-6}$ alkoxy optionally substituted by one or more halogen, CN, O(C$_n$-alkylene)CN, (C$_n$-alkylene)CN, or CO(C$_{1-6}$ alkyl optionally substituted by one or more halogen), wherein the "C-alkylene" linking groups in the definitions above are linear or branched, and are optionally substituted by one or more (C$_{1-6}$ alkyl optionally substituted by one or more halogen) groups, m is an integer from 0 to 3, n is an integer from 1 to 3, and p is an integer from 0 to 2.

Pharmaceutically-acceptable salts are well know to those skilled in the art, and for example include those mentioned by Berge et al, in *J.Pharm.Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more of the substituents on the compound of formula (I) contains an acidic moiety, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

Alkyl groups, including the alkyl moiety of alkoxy groups, may be straight-chain, branched-chain or cyclic where the number of carbon atoms allows.

"Halo" refers to fluoro, chloro, bromo and iodo.

Certain of the compounds of the formula (I) may exist as geometric isomers. Certain of the compounds of the formula (I) may exist as tautomers. The compounds of the formula (I) may possess one or more asymmetric centres and so exist in two or more stereoisomeric forms. The present invention includes all the individual tautomers, stereoisomers and geometric isomers of the compounds of formula (I) and mixtures thereof.

Preferably, R$^1$ is N=C(NH$_2$)$_2$ or NHC(=NH)NH$_2$ and R$^2$ is H.

Preferably, at least two of R$^4$, R$^5$, R$^6$ and R$^7$ are H.

Preferably, R$^3$ is H, halogen or C$_{1-6}$ alkyl optionally substituted by one or more halogen. More preferably, R$^3$ is H, Cl, Br or methyl optionally substituted by one or more halogen. Most preferably, R$^3$ is H, Cl, Br or methyl.

Preferably, R$^4$ is H, OH, halogen, C$_{1-6}$ alkyl optionally substituted by one or more substituents independently selected from halogen or OH, C$_{1-6}$ alkoxy optionally substituted by one or more halogen, CN, (C$_m$-alkylene)CONR$^9$R$^{10}$, O(C$_n$-alkylene)CONR$^9$R$^{10}$, (C$_m$-alkylene)SO$_2$NR$^9$R$^{10}$, or a group of formula X-aryl or X-het.

More preferably, R$^4$ is H, Br, OH, CN, C$_{1-6}$ alkoxy, C$_{1-6}$ alkyl optionally substituted by one or more OH, SO$_2$NR$^9$R$^{10}$, CONR$^9$R$^{10}$, OCH$_2$CONR$^9$R$^{10}$, OCH$_2$aryl, het or aryl.

Yet more preferably, R$^4$ is H, Br, OH, CN, C$_{1-6}$ alkoxy, C$_{1-6}$ alkyl optionally substituted by one or more OH, SO$_2$NR$^9$R$^{10}$, CONH(aryl(C$_{1-6}$ alkyl)), CONH$_2$, OCH$_2$CONR$^9$R$^{10}$, OCH$_2$aryl, phenyl or naphthyl.

Most preferably, R$^4$ is H, Br, CN, OCH$_3$, SO$_2$NH$_2$, CH$_2$OH, CONH$_2$, OCH$_2$CONH$_2$, CONHBn, OBn, OH or Ph.

Preferably, R$^5$ is H, halogen, or C$_{1-6}$ alkyl optionally substituted by one or more substituents independently selected from halogen or OH.

More preferably, R$^5$ is H, Br or methyl optionally substituted by one or more halogen.

Most preferably, R$^5$ is H, Br or methyl.

Preferably, R$^6$ is H, halogen, C$_{1-6}$ alkyl optionally substituted by one or more substituents independently selected from halogen or OH, C$_{1-6}$ alkoxy optionally substituted by one or more halogen, CN, O(C$_n$-alkylene)CN, (C$_n$-alkylene)CN, (C$_m$-alkylene)CONR$^9$R$^{10}$, (C$_m$-alkylene)CO$_2$R$^8$, (C$_m$-alkylene)SO$_2$NR$^9$R$^{10}$, (C$_m$-alkylene)S(O)$_p$R$^{11}$ or a group of formula X-aryl or X-het.

More preferably, R$^6$ is H,Cl, Br, C$_{1-6}$ alkyl optionally substituted by one or more OH, C$_{1-6}$ alkoxy, CN, (C$_m$-alkylene)CONR$^9$R$^{10}$, (C$_m$-alkylene)CO$_2$R$^8$, (C$_m$-alkylene)S(O)$_p$R$^{11}$, (C$_m$-alkylene)SO$_2$NR$^9$R$^{10}$ or a group of formula X-aryl or X-het, where X is a direct link, CH=CH, CH(OH), CO, OCH$_2$, CH$_2$O or CH$_2$.

Yet more preferably, R$^6$ is H, Br, methyl optionally substituted by OH, ethyl optionally substituted by OH, cyclopentyl optionally substituted by OH, cyclohexyl optionally substituted by OH, C$_{1-6}$ alkoxy, CN, O(C$_n$-alkylene)CN, (C$_n$-alkylene)CN, SO$_2$R$^{11}$, SR$^{11}$, CONR$^9$R$^{10}$, CO$_2$R$^8$, SO$_2$NR$^9$R$^{10}$, a group of formula X-(optionally substituted phenyl) or X-het$^1$, where X is a direct link, CH=CH, CH(OH), CO, OCH$_2$, CH$_2$O or CH$_2$, and where the phenyl moiety linked via X is optionally substituted by one or more halogen, C$_{1-6}$ alkyl optionally substituted by one or more substituents independently selected from halogen and OH, C$_{1-6}$ alkoxy optionally substituted by one or more halogen, or CO$_2$R$^{13}$, where "het$^1$" is an optionally benzo-fused dioxolyl, furyl, thienyl, imidazolyl, or a partially or fully saturated analogue thereof, and such "het$^1$" group linked via X being optionally substituted by one or more C$_{1-6}$ alkyl optionally substituted by one or more substituents independently selected from halogen and OH.

Further more preferably, $R^6$ is H, Br, $CO_2H$, (E)CH=CHPh, Ph, $OCH_3$, 1,3-benzo[d]dioxol-5-yl, CN, $CH_2OH$, CONHBn, 4-methoxyphenyl, 1-hydroxycyclohexyl, 1-hydroxycyclopentyl, COPh, $CH(OH)CH_3$, CH(OH)Ph, $CCH_3(OH)Ph$, $OCH_2Ph$, $SO_2Ph$, SPh, $CH_2OPh$, $SO_2NH_2$, $SO_2NHPh$, $SO_2NH$(cyclopentyl), $SO_2$(pyrrolidino), $SO_2$(morpholino), $SO_2$(N-methylpiperazino), (2-methylimidazol-1-yl)methyl, (2-methylbenzimidazol-1-yl)methyl, benzofuran-2-yl, thien-3-yl, thien-2-yl, 4-methylphenyl, 2-methoxyphenyl, 3-methoxyphenyl, 3,5-dimethoxyphenyl, 2,6-dimethoxyphenyl, 3-carboxyphenyl, 3-cyanophenyl or 3-chlorophenyl.

Most preferably, $R^6$ is CH(OH)Ph, 2-methoxyphenyl, 3-methoxyphenyl, 4-methoxyphenyl, 2,6-dimethoxyphenyl, $SO_2NH_2$, $SO_2NHPh$, $SO_2NH$(cyclopentyl), $SO_2$(pyrrolidino), $SO_2$(morpholino), $SO_2Ph$, SPh, $SO_2$(N-methylpiperazino) or 3-carboxyphenyl.

Preferably, $R^7$ is H.

A preferred group of compounds is one in which $R^1$ is $N=C(NH_2)_2$ or $NH(C(=NH)NH_2$, each of $R^2$, $R^4$, R and $R^7$ are H, $R^3$ is Br or Cl, and $R^6$ is 2-methoxyphenyl, 4-methoxyphenyl, CH(OH)Ph, $SO_2Ph$, SPh, 3-carboxyphenyl or 3-methoxyphenyl.

Another preferred group of compounds are those in which two of $R^4$, $R^5$, $R^6$ and $R^7$ are attached to adjacent carbon atoms, and are taken together to form a $OCH_2O$ moiety, Yet another preferred group are the compounds of the Examples, and the salts thereof.

The most preferred compounds are selected from:
(4-chloro-7-(2-methoxyphenyl)isoquinolin-1-yl)guanidine;
(4-chloro-7-(3-methoxyphenyl)isoquinolin-1-yl)guanidine;
(4-chloro-7-(4-methoxyphenyl)isoquinolin-1-yl)guanidine;
(4-chloro-7-(2,6-dimethoxyphenyl)isoquinolin-1-yl)guanidine;
(4-bromo-7-(3-methoxyphenyl)isoquinolin-1-yl)guanidine;
(4-bromo-7-(4-methoxyphenyl)isoquinolin-1-yl)guanidine;
(4-chloro-7-(α-hydroxybenzyl)isoquinolin-1-yl)guanidine;
(4-chloro-7-(3-carboxyphenyl)isoquinolin-1-yl)guanidine;
1-guanidino-7-sulphamoylisoquinoline;
1-guanidino-7-phenylsulphamoylisoquinoline;
4-chloro-1-guanidino-7-sulphamoylisoquinoline;
4-chloro-7-cyclopentylsulphamoyl-1-guanidinoisoquinoline;
4-chloro-1-guanidino-7-(1-pyrrolidinosulphonyl)isoquinoline hydrochloride;
4-chloro-1-guanidino-7-morpholinosulphonylisoquinoline hydrochloride;
4-chloro-1-guanidino-7-[(N-methylpiperazino)sulphonyl]isoquinoline;
4-chloro-1-guanidino-7-(phenylsulphanyl)isoquinoline;
4-chloro-1-guanidino-7-(phenylsulphonyl)isoquinoline; and the salts thereof.

Another aspect of the invention is a pharmaceutical composition comprising a compound or salt according to the above definitions and a pharmaceutically-acceptable adjuvant, carrier or diluent.

Yet another aspect of the invention is a compound or salt according to the above definitions for use as a medicament.

A further aspect of the invention is the use of a compound or salt according to the above definitions for the manufacture of a medicament for the treatment of a condition or process mediated by uPA, such as chronic dermal ulcer, angiogenesis (neo-vascularization), bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

Yet another aspect of the invention is a method of treatment of a condition or process mediated by uPA, such as chronic dermal ulcer, angiogenesis (neo-vascularization), bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis, comprising administering a therapeutic amount of a compound or salt or composition according to the above definitions.

It is to be appreciated that reference to treatment includes prophylaxis as well as the alleviation of established symptoms of uPA-mediated conditions.

The invention further provides Methods for the production of compounds of the invention, which are described below and in the Examples. The skilled person will appreciate that the compounds of the invention could be made by methods other than those herein described, by adaptation of the methods herein described in the sections below and/or adaptation thereof, and of methods known in the art.

In the Methods below, unless otherwise specified, the substituents are as defined above with reference to the compounds of formula (I) above.

Method 1

Compounds of formula (I) can be obtained from the corresponding 1- or 3-aminoisoquinoline derivative (II) as appropriate:

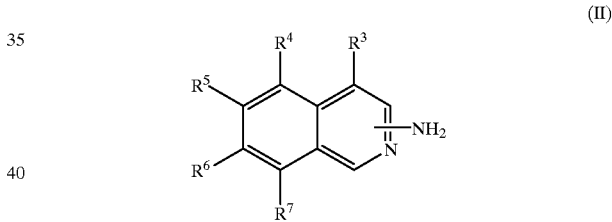

(II)

by reaction with cyanamide ($NH_2CN$) or a reagent which acts as a "$NHC^+=NH$" synthon such as carboxamidine derivatives, e.g. 1H-pyrazole-1-carboxamidine (M. S. Bernatowicz, Y. Wu, G. R. Matsueda, *J. Org. Chem.*, 1992, 57, 2497), the 3,5-dimethylpyrazole analogue thereof (M. A. Brimble et al, *J. Chem.Soc.Perkin Trans.I*(1990)311), simple O-alkylthiouronium salts or S-alkylisothiouronium salts such as O-methylisothiourea (F. El-Fehail et al, *J.Med.Chem.*(1986), 29, 984), S-methylisothiouronium sulphate (S. Botros et al, *J.Med.Chem.*(1986)29,874; P. S. Chauhan et al, *Ind. J. Chem.*, 1993, 32B, 858) or S-ethylisothiouronium bromide (M. L. Pedersen et al, *J.Org.Chem.*(1993) 58, 6966). Alternatively aminoiminomethanesulphinic acid, or aminoiminomethanesulphonic acid may be used (A. E. Miller et al, *Synthesis* (1986) 777; K. Kim et al, *Tet.Lett.*(1988) 29,3183).

Other methods for this transformation are known to those skilled in the art (see for example, "Comprehensive Organic Functional Group Transformations", 1995, Pergamon Press, Vol 6 p639, T. L. Gilchrist (Ed.); Patai's "Chemistry of Functional Groups", Vol. 2. "The Chemistry of Amidines and Imidates", 1991, 488).

Aminoisoquinolines (II) may be prepared by standard published methods (see for example, "The Chemistry of Heterocyclic Compounds" Vol. 38 Pt. 2 John Wiley & Sons, Ed. F. G. Kathawala, G. M. Coppolq, H. F. Schuster) including, for example, by rearrangement from the corresponding carboxy-derivative (Hoffmann, Curtius, Lossen, Schmidt-type rearrangements) and subsequent deprotection.

Aminoisoquinolines (II) may alternatively be prepared by direct displacement of a leaving group such as Cl or Br with a nitrogen nucleophile such as azide (followed by reduction), or by ammonia, or through Pd-catalysis with a suitable amine (such as benzylamine) followed by deprotection using standard conditions well-known in the art.

1-(Chloro or bromo)isoquinolines can be prepared by treatment of the corresponding N-oxides of formula (III) with $POCl_3$ or $POBr_3$ respectively in an inert solvent such as methylene chloride at reflux.

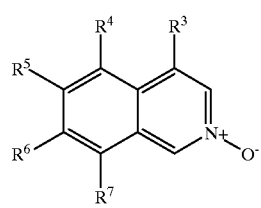

(III)

Haloisoquinolines are commercially available or can alternatively be prepared by various methods, for example those described in: Goldschmidt, Chem.Ber.(1895)28,1532; Brown and Plasz, J.Het.Chem.(1971)6,303; U.S. Pat. No. 3,930,837; Hall et al, Can.J.Chem.(1966)44,2473; White, J.Org.Chem.(1967)32,2689; and Ban, Chem.Pharm.Bull. (1964)12,1296.

1,4-(Dichloro- or dibromo)isoquinolines can be prepared by the method described by M. Robison et al in J.Org.Chem. (1958)23,1071, by reaction of the corresponding isocarbostyryl compound with $PCl_5$ or $PBr_5$.

Method 2

Compounds of formula (I) can be obtained from the corresponding aminoisoquinoline derivative (II) as defined in Method 1 above, via reaction with a reagent which acts as a protected amidine(2+) synthon (IV),

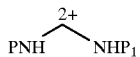

(IV)

such as a compound $PNHC(=X)NHP_1$, $PN=CXNHP_1$ or $PNHCX=NP_1$, where X is a leaving group such as Cl, Br, I, mesylate, tosylate, alkyloxy, etc., and where P and $P_1$ may be the same or different and are N-protecting groups such as are well-known in the art, such as t-butoxycarbonyl, benzyloxycarbonyl, arylsulphonyl such as toluenesulphonyl, nitro, etc.

Examples of reagents that act as synthons (IV) include N,N'-protected-S-alkylthiouronium derivatives such as N,N'-bis(t-butoxycarbonyl)-S-Me-isothiourea, N,N'-bis (benzyloxycarbonyl)-S-methylisothiourea, or sulphonic acid derivatives of these (J. Org. Chem. 1986, 51, 1882), or S-arylthiouronium derivatives such as N,N'-bis(t-butoxycarbonyl)-S-(2,4-dinitrobenzene) (S. G. Lammin, B. L. Pedgrift, A. J. Ratcliffe, Tet. Lett. 1996, 37, 6815), or mono-protected analogues such as [(4-methoxy-2,3,6-trimethylphenyl)sulphonyl]-carbamimidothioic acid methyl ester or the corresponding 2,2,5,7,8-pentamethylchroman-6-sulphonyl analogue (D. R. Kent, W. L. Cody, A. M. Doherty, Tet. Lett., 1996, 37, 8711), or S-methyl-N-nitroisothiourea (L. Fishbein et al, J.Am.Chem.Soc. (1954) 76, 1877) or various substituted thioureas such as N,N'-bis (t-butoxycarbonyl)thiourea (C. Levallet, J. Lerpiniere, S. Y. Ko, Tet. 1997, 53, 5291) with or without the presence of a promoter such as a Mukaiyama's reagent (Yong, Y. F.; Kowalski, J. A.; Lipton, M. A. J. Org. Chem., 1997, 62, 1540), or copper, mercury or silver salts, particularly with mercury (II) chloride. Suitably N-protected O-alkylisoureas may also be used such as O-methyl-N-nitroisourea (N.Heyboer et al, Rec.Chim.Trav.Pays-Bas (1962)81,69). Alternatively other guanylation agents known to those skilled in the art such as 1-H-pyrazole-1-[N,N'-bis(t-butoxycarbonyl)]carboxamidine, the corresponding bis-Cbz derivative (M. S. Bernatowicz, Y. Wu, G. R. Matsueda, Tet. Lett. 1993, 34, 3389) or monoBoc or mono-Cbz derivatives may be used (B. Drake. Synthesis, 1994, 579, M. S. Bernatowicz. Tet. Lett. 1993, 34, 3389). Similarly, 3,5-dimethyl-1-nitroguanylpyrazole may be used (T. Wakayima et al, Tet.Lett.(1986)29,2143).

The reaction can conveniently be carried out using a suitable solvent such as dichloromethane, N,N-dimethylformamide (DMF), methanol.

The reaction is also conveniently carried out by adding mercury (II) chloride to a mixture of the aminoisoquinoline (II) and a thiourea derivative of type (IV) in a suitable base solvent mixture such as triethylamine/dichloromethane.

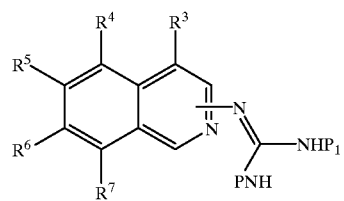

(V)

The product of this reaction is the protected isoquinolinylguanidine (V), which can conveniently be deprotected to give (I) or a salt thereof. For example, if the protecting group P and/or $P_1$ is t-butoxycarbonyl, conveniently the deprotection is carried out using an acid such as trifluoroacetic acid (TFA) or hydrochloric acid, in a suitable solvent such as dichloromethane, to give the bistrifluoroacetate salt of (I).

If P and/or $P_1$ is a hydrogenolysable group, such as benzyloxycarbonyl, the deprotection could be performed by hydrogenolysis.

Other protection/deprotection regimes include:
nitro (K.Suzuki et al, Chem.Pharm.Bull. (1985)33,1528, Nencioni et al, J.Med.Chem.(1991)34,3373, B. T. Golding et al, J.C.S.Chem.Comm.(1994)2613;
p-toluenesulphonyl (J. F. Callaghan et al, Tetrahedron (1993) 49 3479;
mesitylsulphonyl (Shiori et al, Chem.Pharm.Bull.(1987) 35,2698, ibid.(1987)35,2561, ibid., (1989)37,3432, ibid., (1987)35,3880, ibid., (1987)35,1076;
2-adamantoyloxycarbonyl (Iuchi et al, ibid., (1987) 35, 4307; and methylsulphonylethoxycarbonyl (Filippov et al, Syn.Lett.(1994)922)

It will be apparent to those skilled in the art that other protection and subsequent deprotection regimes during synthesis of a compound of the invention may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

Method 3

Compounds with the formula (I) where $R^1$ is guanidinyl and $R^2$ is H, or $R^1$ is H and $R^2$ is guanidinyl can be obtained from compounds of formula (VI):

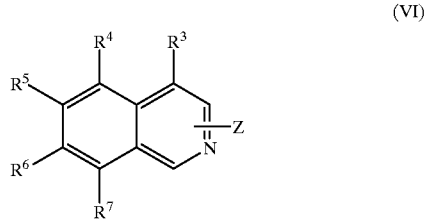

(VI)

where Z is attached at the 1- or 3-position as appropriate and is a suitable leaving group such as Cl, Br or OPh, by displacement of the leaving group by the free base of guanidine.

The free base of guanidine may conveniently be generated in situ from a suitable salt, such as the hydrochloride, carbonate, nitrate, or sulphate with a suitable base such as sodium hydride, potassium hydride, or another alkali metal base, preferably in a dry non-protic solvent such as tetrahydrofuran (THF), DMSO, N,N-dimethylformamide (DMF), ethylene glycol dimethyl ether (DME), N,N-dimethyl acetamide (DMA), toluene or mixtures thereof. Alternatively it can be generated from a suitable salt using an alkoxide in an alcohol solvent such as potassium t-butoxide in t-butanol, or in a non-protic solvent as above.

The thus formed free guanidine can be combined with the 1- or 3-isoquinoline derivative, and the reaction to form compounds of formula (I) can be carried out at from room temperature to 200° C., preferably from about 50° C. to 150° C., preferably for between 4 hours and 6 days.

Method 4

Compounds of the formula (I) when one or more of $R^{4-7}$ is or contains a hydroxy group, may be prepared from a suitably "protected" hydroxy derivative, i.e. a compound of the formula (I) where one or more of $R^{4-7}$ is or contains "$OP^2$", where $P^2$ is a suitable O-protecting group such as O-benzyl. The benzyl group may be removed for example by catalytic hydrogenation using a palladium on charcoal catalyst in a suitable solvent such as ethanol at about 20° C. and elevated pressure, optionally in the presence of an excess of an acid such as HCl or AcOH, or TFA, or by other known deprotection methods.

Suitable O-protecting groups and protection/deprotection can be found in the texts by Greene and Wuts, and Kocienski, supra.

Method 5

Compounds of the invention where $R^4$–$R^7$ is or contains a carboxylic acid group or carbamoyl group can be made from the corresponding compound where the substituent is a nitrile by full or partial hydrolysis. Compounds of the invention where $R^4$–$R^7$ is or contains a carboxylic acid group can be made from the corresponding compound where the substituent is a carbamoyl moiety, by hydrolysis. The hydrolysis can be carried out by methods well-known in the art, for example those mentioned in "Advanced Organic Chemistry" by J. March, 3rd edition (Wiley-Interscience) chapter 6-5, and references therein. Conveniently the hydrolysis is carried out using concentrated hydrochloric acid, at elevated temperatures, and the product forms the hydrochloride salt.

Method 6

Where desired or necessary the compound of formula (I) is converted into a pharmaceutically acceptable salt thereof.

A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

General Methods of Interconversion

Compounds of the formula (I) where one or more of $R^3$–$R^7$ is or contains Cl or Br may be dehalogenated to give the corresponding hydrido compounds of formula (I) by hydrogenolysis, suitably using a palladium on charcoal catalyst, in a suitable solvent such as ethanol at about 20° C. and at elevated pressure.

Compounds of formula (I) where $R^1$ is guanidinyl and one or more of $R^4$–$R^7$ is or contains a carboxy group may be prepared from a compound with a group hydrolysable to give a carboxy moiety, for example a corresponding nitrile or ester, by hydrolysis, for example by acidic hydrolysis with e.g. conc. aq. HCl at reflux. Other hydrolysis methods are well known in the art.

Compounds of formula (I) in which one or more of $R^4$–$R^7$ contains an amide moiety may be made via reaction of an optionally protected corresponding carboxy compound, either by direct coupling with the amine of choice, or via initial formation of the corresponding acid chloride and subsequent reaction with the amine, followed by deprotection if appropriate. Such transformations are well-known in the art.

Certain of the compounds of formula (I) which has an electrophilic group attached to an aromatic ring can be made by reaction of the corresponding hydrido compound with an electrophilic reagent.

For example sulphonylation of the aromatic ring using standard reagents and methods, such as fuming sulphuric acid, gives a corresponding sulphonic acid. This can then be optionally converted into the corresponding sulphonamide by methods known in the art, for example by firstly converting to the sulphonyl chloride followed by reaction with an amine.

Certain of the compounds of the invention can be made by cross-coupling techniques such as by reaction of a compound containing a bromo-substituent attached to e.g. an aromatic ring, with e.g. a boronic acid derivative, an olefin or a tin derivative by methods well-known in the art, for example by the methods described in certain of the Preparations below.

Certain of the compounds of the invention having an electrophilic substituent can be made via halogen/metal exchange followed be reaction with an electrophilic reagent. For example a bromo-substituent may react with a lithiating reagent such as n-butyllithium and subsequently an electrophilic reagent such as $CO_2$, an aldehyde or ketone, to give respectively an acid or an alcohol.

Compounds of the invention are available by either the methods described herein in the Methods and Examples or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

The compounds and salts of the invention may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

For human use, the compounds of formula (I) or their salts can be administered alone, but will generally be administered in admixture with a pharmaceutically acceptable adjuvant, diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, in the form of sterile creams, gels, suspensions, lotions, ointments, dusting powders, sprays, drug-incorporated dressings or via a skin patch. For example they can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride).

All such formulations may also contain appropriate stabilisers and preservatives. For oral and parenteral administration to human patients, the daily dosage level of the compounds of formula (I) or their salts will be from 0.001 to 20, preferably from 0.01 to 20, more preferably from 0.1 to 10, and most preferably from 0.5 to 5 mg/kg (in single or divided doses). Thus tablets or capsules of the compounds will contain from 0.1 to 500, preferably from 50 to 200, mg of active compound for administration singly or two or more at a time as appropriate.

The physician in any event will determine the actual dosage which will be most suitable for a an individual patient and it will vary with the age, weight and response of the particular patient. The above dosages are exemplary of the average case; there can of course be individual instances where higher or lower dosage ranges are merited, and such are within the scope of this invention.

It is to be appreciated that reference to treatment includes prophylaxis as well as the alleviation of established symptoms of the condition to be treated.

Test Methods

Compounds were tested for their ability to inhibit human urokinase, human tPA and human plasmin, using substantially the same methods as described by Yang, et al, *J.Med.Chem.*,(1990)33,2961. The urokinase assay was carried out using S-2444 (Quadratech 820357) as substrate and the urokinase used was HMWT Human Urokinase (Calbiochem 672081). The tPA assay was carried out using S-2288 (Quadratech 820832) tPA substrate, Quadratech 321116 as tPA stimulator, and the tPA used was Human tPA (Quadratech 881157).

The plasmin assay was carried out using human plasmin (Quadratech 810665) acting on Chromozym-PL (Boehringer 378461) as substrate.

As shown below, the substances of the invention are selective uPA inhibitors:

| Example No. | $K_i$ uPA (nM) | vs. tPA* | vs. plasmin* |
|---|---|---|---|
| 15 | 249 | 380 | 204 |
| 19 | 400 | 88 | 68 |
| 35 | 63 | >1000 | 286. |

*selectivity figures

Some of the compounds of the invention are named as derivatives of guanidine, and some as derivatives of isoquinoline.

EXAMPLES AND PREPARATIONS

Melting points were determined using a Gallenkamp melting point apparatus and are uncorrected. Nuclear magnetic resonance data were obtained using a Varian Unity 300 or Varian Inova 400 spectrometer, and are quoted in parts per million from tetramethylsilane. Mass spectral data were obtained on a Finnigan Mat. TSQ 7000 or a Fisons Instruments Trio 1000. The calculated and observed ions quoted refer to the isotopic composition of lowest mass. Reference to "ether" in this section should be read as diethyl ether, unless specified otherwise. "Ph" represents the phenyl group, "Bn" represents the benzyl group and "Me" represents the methyl group. "TLC" means thin layer chromatography. "TFA" represents trifluoroacetic acid.

Example 1

1-Isoquinolinylguanidine

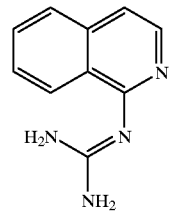

Sodium hydride (192 mg, 60% dispersion in mineral oil, 4.8 mmol) was added in one portion to a stirred solution of guanidine hydrochloride (465 mg, 4.9 mmol) in DMSO (6.0 mL) under nitrogen at room temperature, and the mixture was stirred until the evolution of hydrogen had ceased. 1-Chloroisoquinoline (300 mg, 1.83 mmol) was added and the mixture was heated at 100° C. for 3 days. The solvents were evaporated in vacuo and the residue directly purified by column chromatography upon silica gel using dichloromethane:methanol:ammonia 0.880 (95:5:0.5 to 90:10:1) as eluant to give 1-isoquinolinylguanidine (195 mg, 1.0 mmol) as a white solid.

M.Pt. 163–5° C.;

$^1$H NMR (δ, DMSO-$d_6$, 400 MHz) 6.95 (1H, d), 7.4 (1H, dd), 7.55 (1H, dd), 7.65 (1H, d), 7.85 (1H, d), 8.55 (1H, d); LRMS 187 (MH), 373 ($M_2$H);

Elemental Analysis: Found—C, 61.66; H, 5.37; N, 29.10. Calcd for $C_{10}H_{10}N_4$+0.45 $H_2O$—C, 61.81; H, 5.65; N, 28.83.

Other compounds prepared by the same general method, using appropriate starting materials, are listed in Table 1 below.

Examples 2 and 3 were characterised as the corresponding hydrochloride salts, prepared by addition of ethereal HCl to a solution of the free base and evaporation to dryness. Examples 28 and 29 were characterised as the trifluoroacetate salts, prepared by dissolution of the free base in trifluoroacetic acid and evaporation to dryness.

TABLE 1

(NB unless otherwise specified, substituents are H)

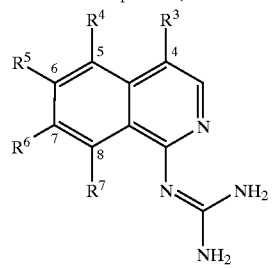

| Ex. | $R^3$ | $R^{4-7}$ | Rn. Condns. (a) | Mp ° C. | Elemental Analysis | LRMS | $^1$H, δ |
|---|---|---|---|---|---|---|---|
| 2$^{(c)}$ | Cl | — | τ-BuOH, 60° C., 4 h | 131–3 | — | 221, 223 (MH) | (DMSO-$d_6$ + TFAD, 300 MHz) 7.85 (1 H, dd), 8.0 (1 H, dd), 8.15 (1 H, d), 8.25 (1 H, s), 8.5 (1 H, d), 14.5–15.0 (4 H, br s) |
| 3$^{(d)}$ | Br | — | τ-BuOH, 90° C., 4 h | 165.5–168 | Found: C, 39.41; H, 3.12; N, 18.16. Calcd for $C_{10}H_9BrN_4$.HCl + 0.2 $H_2O$: C, 39.36; H, 3.43; N, 18.36. | 265, 267 (MH) | (DMSO-$d_6$, 400 MHz) 7.1–7.5 (4 H, br s), 7.6 (1 H, dd), 7.8 (1 H, dd), 7.85 (1 H, d), 8.1 (1 H, s), 8.7 (1 H, d) |
| 4$^{(e)}$ | Me | — | 100° C., 5 days | 46–47 | — | 201 (MH) | (DMSO-$d_6$, 300 MHz) 2.4 (3 H, s), 6.9–7.45 (4 H, br s), 7.45 (1 H, dd), 7.65 (1 H, dd), 7.75 (1 H, d), 7.8 (1 H, s), 8.65 (1 H, d) |
| 5$^{(f)}$ | — | 5-Br | τ-BuOH, reflux, 4 days | | Found: C, 44.35; H, 3.31; N, 20.68. Calcd for $C_{10}H_9BrN_4$ + 0.1 $CH_2Cl_2$: C, 44.34; H, 3.39: N, 20.48. | 265, 267 (MH) | (CDCl$_3$, 300 MHz) 5.5–6.6 (4 H, br s), 7.35 (1 H, dd), 7.45 (1 H, d), 7.85 (1 H, d), 8.15 (1 H, d), 8.7 (1 H, d) |
| 6$^{(g)}$ | — | 5-OMe | 100° C., 3.5 days | 182–4 | Found: C, 60.07; H, 5.49; N, 25.27. Calcd for $C_{11}H_{12}N_4O$ + 0.2 $H_2O$ + 0.02 $CH_2Cl_2$: C, 59,80; H, 5.66; N, 25.32. | 217 (MH) | (CDCl$_3$, 400 MHz) 3.95 (3 H, s), 6.9 (1 H, d), 7.35 (1 H, dd), 7.45 (1 H, d), 8.0 (1 H, d), 8.25 (1 H, d) |
| 7 | — | 5-OBn | 100° C., 2.5 days | 208–210 | Found: C, 61.77; H, 5.17; N, 16.93. Calcd for $C_{17}H_{16}N_4O$ + 0.2 $H_2O$ + 0.5 $CH_2Cl_2$:C, 62.11; H, 5.18; N, 16.56 | 293 (MH) | (DMSO-$d_6$, 400 MHz) 5.3 (2 H, s), 7.3–7.4 (4 H, m), 7.5 (2 H, d), 7.65 (1 H, dd), 7.75 (1 H, d), 8.15 (1 H, d), 8.3 (1 H, d) |
| 8 | — | 5-OCH$_2$—CONH$_2$ | reflux, 4 days | >200 | — | 260 (MH) | (DMSO-$d_6$, 400 MHz) 4.55 (2 H, s), 7.0 (1 H, d), 7.2–7.8 (8 H, br m), 7.95 (1 H, d), 8.2 (1 H, d) |
| 9 | — | 5-CH$_2$OH | 100° C. 3.5 days | 177–9 | Found: C, 56.84; H, 5.23; N, 23.28. Calcd for $C_{11}H_{12}N_4O$ + 0.44 $H_2O$ + 0.15 $CH_2Cl_2$: C, 56,53; H, 5.61; N, 23.65 | 217 (MH) | (DMSO-$d_6$, 400 MHz) 4.8 (2 H, s), 5.2 (1 H; br s), 7.0–7.65 (4 H, br m), 7.65 (1 H, d), 7.95 (1 H, d), 8.5 (1 H, d) |
| 10 | — | 5-CONH$_2$ | 100° C., 3.5 days | 198 | Found: C, 50.28; H, 4.91; N, 26.50. Calcd for $C_{11}H_{11}N_5O$ + 1.3 $H_2O$ + 0.16 $CH_2Cl_2$: C, 50.34; H, 5.27; N, 26.30 | 230 (MH), 459 ($M_2$H) | (MeOH-$d_4$, 400 MHZ) 6.1 (1 H, dd), 6.15 (1 H, d), 6.35 (1 H, d), 6.6 (1 H, d), 7.05 (1 H, d) |
| 11 | — | 5-Ph | 100° C., 3.5 days | 73–5 | Found: C, 69.58; H, 5.35; N, 20.46. Calcd for | 263 (MH), | (DMSO-$d_6$, 400 MHz) 6.85 (1 H, d), 7.0–7.6 (11 H, m), 7.85 (1 H, d), 8.65 (1 H, d) |

TABLE 1-continued (NB unless otherwise specified, substituents are H)

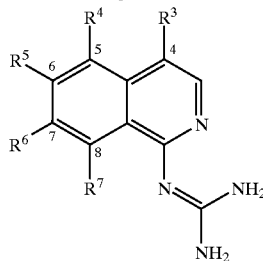

| Ex. | $R^3$ | $R^{4-7}$ | Rn. Condns. (a) | Mp °C. | Elemental Analysis | LRMS | $^1H$, δ |
|---|---|---|---|---|---|---|---|
| | | | | | $C_{16}H_{14}N_4$ + 0.7 $H_2O$ + 0.02 $CH_2Cl_2$; C, 69.56; H, 5.63; N, 20.25. | 525 ($M_2H$) | |
| 12 | — | 5-$SO_2NH_2$ | 100° C., 3 days | >220 | Found: C, 44.78; H, 4.13; N, 25.42. Calcd for $C_{10}H_{11}N_5O_2S$ + 0.25 $H_2O$ + 0.06 MeOH: C, 44.47; H, 4.36; N, 25.77. | 266 (MH) | (DMSO-$d_6$, 400 MHz) 7.0–7.4 (4 H, br s), 7.45–7.5 (3 H, m), 7.55 (1 H, d), 8.0 (1 H, d), 8.1 (1 H, d), 8.9 (1 H, d) |
| 13 | — | 6-Br | 100° C., 3 days | 144–6 | Found: C, 44.15; H, 3.48; N, 20.01. Calcd for $C_{10}H_9BrN_4$ + 0.3 $H_2O$ + 0.05 $CH_2Cl_2$: C, 43.93; H, 3.56; N, 20.39. | 265, 267 (MH) | (DMSO-$d_6$, 300 MHz) 6.95 (1 H, d), 6.95–7.4 (4 H, br s), 7.55 (1 H, d), 7.9–8.0 (2 H, m), 8.5 (1 H, d) |
| 14 | — | 6-Me | 120° C., 6 days | 80 dec. | — | 201 (MH) | (DMSO-$d_6$, 300 MHz) 7.1 (1 H, d), 7.4 (1 H, d), 7.55 (1 H, s), 7.0–8.4 (4 H, br s), 7.95 (1 H, d), 8.55 (1 H, s) |
| 15 | — | 7-Br | reflux, 3 days | 198–200 | Found: C, 44.29; H, 3.29; N, 20.42. Calcd for $C_{10}H_9BrN_4$ + 0.1 $CH_2Cl_2$: C, 44.34; H, 3.39; N, 20.48. | 265 (MH) | (CDCl$_3$, 400 MHz) 5.3–6.8 (4 H, br s), 7.05 (1 H, d), 7.5 (1 H, d), 7.65 (1 H, d), 8.05 (1 H, d), 8.9 (1 H, s) |
| 16[h] | — | 7-OMe | 95° C., 2 days | — | — | 217 (MH), 433 ($M_2H$) | (DMSO-$d_6$, 300 MHz) 3.8 (3 H, s), 7.0–7.5 (6 H, m), 7.6 (1 H, d), 7.8 (1 H, d), 8.0 (1 H, s) |
| 17 | — | 7-Ph | 100° C., 50 h | — | — | 263 (MH) | (DMSO-$d_6$, 400 MHz) 7.0–7.45 (6 H, br m), 7.45–7.55 (2 H, m), 7.7–7.8 (3 H, m), 7.9–8.0 (2 H, m), 8.95 (1 H, s) |
| 18 | — | 7-(3,4-OCH$_2$O—Ph) | 90° C., 40h | — | — | 307 (MH), 613 ($M_2H$) | (DMSO-$d_6$, 400 MHz) 6.0 (2 H, s), 7.0 (2 H, m), 7.2 (1 H, d), 7.25 (1 H, s), 7.65–7.75 (1 H, m), 7.8–7.9 (2 H; m), 8.75 (1 H, s) |
| 19 | — | 7-E-styryl | 100° C., 5 days | 211–3 | Found: C, 72.63; H, 5.66; N, 18.62. Calcd for $C_{18}H_{16}N_4$ + 0.5 $H_2O$: C, 72.71; H, 5.76; N, 18.84. | 289 (MH) | (DMSO-$d_6$, 300 MHz) 7.0–7.45 (10 H, m), 7.6–7.75 (3 H, m), 7.85–8.0 (2 H, m), 8.65 (1 H, s) |
| 20 | — | 7-OBn | 100° C., 5 days | 203–7 | — | 293 (MH) | (MeOH-$d_4$, 300 MHz) 5.3 (2 H, s), 7.3–7.4 (3 H, m), 7.5–7.6 (4 H, m), 7.8–7.95 (2 H, m), 8.1 (1 H, d) |
| 21 | — | 7-CN | 100° C., 17 h | 204–5 | Found: C, 59.13; H, 4.18; N, 30.25. Calcd for $C_{11}H_9N_5$ + 0.21 $CH_2Cl_2$: C, 58,78; H, 4.15; N, 30.57. | 212 (MH) | (DMSO-$d_6$, 400 MHz) 7.0 (1 H, d), 7.0–7.5 (4 H, br s), 7.75 (1 H, d), 7.8 (1 H, d), 8.0 (1 H, d), 8.95 (1 H, s) |
| 22 | — | 7-CH$_2$OH | 100° C., 48 h | >220 | — | 217 (MH) | (DMSO-$d_6$, 300 MHz) 4.7 (2 H, d), 5.25 (1 H, t), 7.6 (1 H, d), 7.85 (1 H, d), 8.0 (1 H, d), 8.0–9.4 (4 H, br s), 8.15 (1 H, d), 8.65 (1 H, s) |
| 23 | — | 7-CH$_2$OPh | 80° C., 17 h | <60 | — | 293 (MH) | (DMSO-$d_6$, 300 MHz) 5.3 (2 H, s), 6.95 (1 H, dd), 7.1 (2 H, d), 7.25 (2 H, dd), 7.6 (1 H, d), 7.9 (1 H, d), 8.05 (1 H, d), 8.15 (1 H, s), 8.9 (1 H, d), 8.2–9.2 (4 H, br s) |
| 24 | — | 7-CH$_2$-(2-Me-1-H-imidazol-1-yl) | 80° C., 28 h | 232–4 | Found: C, 63.10; H, 5.67; N, 28.85. Calcd for $C_{15}H_{16}N_6$ + 0.4 $H_2O$: C, 62.66; H, 5.89; N, 29.23. | 281 (MH) | (DMSO-$d_6$ + TFAD, 400 MHz) 2.6 (3 H, s), 5.5 (2 H, s), 7.55–7.65 (3 H, m), 7.7 (1 H, d), 8.0 (1 H, d), 8,15 (1 H, d), 8.4 (1 H, s) |
| 25 | — | 7-CH$_2$-(2-Me-1-H-benz-imidazol-1-yl) | 95° C., 26 h | 245–7 | Found: C, 66.63; H, 6.19; N, 22.37. Calcd for $C_{19}H_{18}N_6$ + 0.5 $H_2O$ + 0.6 i-PrOH: C, 66.54; H, 6.39; N, 22.38. | 331 (MH), 661 ($M_2H$) | (DMSO-$d_6$, 400 MHz) 2.9 (3 H, s), 5.85 (2 H, s), 7.4–7.6 (3 H, m), 7.65 (1 H, d), 7.7–7.8 (2 H, m), 7.95 (1 H, d), 8.15 (1 H, d), 8.55 (1 H, s) |

TABLE 1-continued (NB unless otherwise specified, substituents are H)

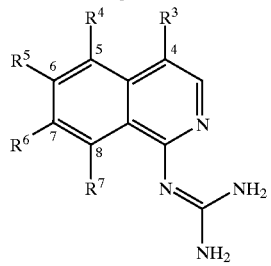

| Ex. | R³ | R⁴⁻⁷ | Rn. Condns. (a) | Mp °C. | Elemental Analysis | LRMS | ¹H, δ |
|---|---|---|---|---|---|---|---|
| 26 | — | 7-CONHBn | 100° C., 2 days | 148–151 | — | 320 (MH) | MeOH-d₄, 300 MHz) 4.65 (2 H, s), 4.8 (5 H, br s), 7.2–7.45 (6 H, m), 7.8 (1 H, dd), 8.0–8.15 (2 H, m), 9.0 (1 H, s) |
| 27 | — | 7-CH(OH)—Ph | 94° C., 8.5 h | 163–5 | Found: C, 63.43; H, 5.39; N, 17.49. Calcd for C₁₇H₁₆N₄O + 0.37 CH₂Cl₂ + 0.2 H₂O; C, 63.73; H, 5.28; N, 17.11. | 293 (MH) | (MeOH-d₄, 400 MHz) 5.9 (1 H, s), 7.1–7.3 (4 H, m), 7.35 (2 H, d), 7.6 (1 H, d), 7.65 (1 H, d), 8.0 (1 H, d), 8.5 (1 H, s) |
| 28 | — | 7-CH(OH)-Me | 95° C., 2.5 days | — | Found C, 47.78; H, 4.21; N, 15.94. Calcd for C₁₂H₁₄N₄O + 1.1 TFA): C, 47.95; H, 4.28; N, 15.75. | 231 (MH) | (TFAD, 400 MHz) 1.4 (3 H, d), 4.9 (1 H, m), 7.55 (1 H, d), 7.8 (1 H, d), 7.9 (1 H, d), 8.1 (1 H, d), 8.3 (1 H, s) |
| 29⁽ᵇ⁾ | — | 7-COPh | 94° C., 3 days | 108 dec. | Found: C, 55.22; H, 4.15; N, 13.36. Calcd for C₁₇H₁₄N₄O + 0.5 H₂O +TFA: C, 55.21; H, 3.90; N, 13.55. | 291 (MH) | (TFAD, 400 MHz) 7.2 (2 H, dd), 7.7 (1 H, dd), 7.75 (2 H, d), 8.15 (1 H, d), 8.25 (1 H, d), 8.35 (1 H, d), 8.45 (1 H, d), 8.9 (1 H, s) |
| 30 | — | 7-C(Me)OH—Ph | 95° C., 2.5 days | 118 dec. | Found: C, 63.82; H, 5.80; N, 16.31. Calcd for C₁₈H₁₈N₄O + 0.48 CH₂Cl₂: C, 63.94; H, 5.57; N, 16.14. | 307 (MH) | (MeOH-d₄, 400 MHz) 2.0 (3 H, s), 4.8 (5 H, br s), 7.0–7.3 (4 H, m), 7.4 (2 H, d), 7.55 (1 H, d), 7.6 (1 H, d), 8.0 (1 H, d), 8.6 (1 H, s) |
| 31 | — | 7-(1-hydroxy-cyclopent-yl) | 100° C., 14 h | 197–8 | — | 271 (MH) | (MeOH-d₄, 300 MHz) 0.4–0.8 (8 H, m), 5.8 (1 H, d), 6.3 (1 H, d), 6.4 (1 H, d), 6.55 (1 H, d), 7.1 (1 H, s) |
| 32 | — | 7-(1-hydroxy-cyclohex-yl) | 100° C., 16 h | 186.5–188 | Found: C, 55.64; H, 6.08; N, 15.25. Calcd for C₁₆H₂₀N₄O + 1 CH₂Cl₂: C, 55.29; H, 6.00; N, 15.17. | 285 (MH) | (MeOH-d₄, 300 MHz) 1.2–2.0 (10 H, m), 7.15 (1 H, d), 7.7 (1 H, d), 7.85 (1 H, d), 8.0 (1 H, d), 8.6 (1 H, s) |
| 33 | Cl | 7-Br | 100° C., 18 h | 218–220 dec. | Found: C, 40.02; H, 2.75; N, 17.78. Calcd for C₁₀H₈BrClN₄ + 0.3 MeOH: C, 40.01; H, 3.00; N, 18.12. | 299, 301 (MH) | (DMSO-d₆, 300 MHz) 6.8–7.4 (4 H, br s), 7.75 (1 H, d), 7.85 (1 H, d), 8.0 (1 H, s), 8.8 (1 H, s) |
| 34 | Cl | 7-(4-Me—Ph) | 100° C., 4 days | 198–200 | Found: C, 61.38; H, 4.59; N, 16.74. Calcd for C₁₇H₁₅ClN₄ + 0.34 CH₂Cl₂: C, 61.32; H, 4.65; N, 16.49. | 311, 313 (MH) | (DMSO-d₆, 300 MHz) 2.35 (3 H, s), 6.9–7.3 (4 H, br s), 7.3 (2 H, d), 7.65 (2 H, d), 7.9 (1 H, d), 7.95 (1 H, s), 8.05 (1 H, d), 8.95 (1 H, s) |
| 35 | Cl | 7-(2-MeO—Ph) | 100° C., 40 h | — | — | 327, 329 (MH) | (DMSO-d₆, 300 MHz) 3.75 (3 H, s), 7.0–7.45 (8 H, m), 7.85 (2 H, br s), 8.0 (1 H, s), 8.7 (1 H, s) |
| 36 | Cl | 7-(3-MeO—Ph) | 100° C., 40 h | 155–6 | Found: C, 59.83; H, 4.45; N, 16.63. Calcd for C₁₇H₁₅ClN₄O + 0.6 H₂O + 0.05 CH₂Cl₂: C, 59.91; H, 4.81; N, 16.39. | 327, 301 (MH) | (DMSO-d₆, 300 MHz) 3.8 (3 H, s), 7.0 (1 H, d), 7.15–7.4 (4 H, br s), 7.25 (1 H, s), 7.3 (1 H, d), 7.45 (1 H, dd), 7.95 (1 H, d), 8.0 (1 H, s), 8.1 (1 H, d), 8.95 (1 H, s) |
| 37 | Cl | 7-(4-MeO—Ph) | 100° C., 2.5 days | 192–4 | Found: C, 60.94; H, 4.51; N, 16.72. Calcd for C₁₇H₁₅ClN₄O + 0.4 H₂O: C, 61.14; H, 4.77; N, 16.77. | 327, 329 (MH) | (DMSO-d₆, 400 MHz) 3.75 (3 H, s), 7.0 (2 H, d), 7.0–7.4 (4 H, br s), 7.65 (2 H, d), 7.85 (1 H, d), 7.9 (1 H, s), 8.0 (1 H, d), 8.85 (1 H, s) |
| 38 | Cl | 7-(3,5-dimethoxy-Ph) | 100° C., 18 h | 210–212 | Found: C, 59.98; H, 4.73; N, 15.53. Calcd for C₁₈H₁₇ClN₄O₂ + 0.02 MeOH + 0.02 CH₂Cl₂: C, 60.33; H, 4.80; N, 15.60. | 357, 359 (MH) | (DMSO-d₆, 400 MHz) 3.8 (6 H, s), 6.5 (1 H; s), 6.8 (2 H, s), 6.9–7.4 (4 H, br s), 7.85 (1 H, d), 7.9 (1 H, s), 8.05 (1 H, d), 8.9 (1 H, s) |

TABLE 1-continued (NB unless otherwise specified, substituents are H)

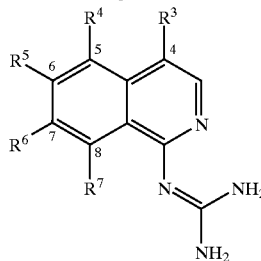

| Ex. | $R^3$ | $R^{4-7}$ | Rn. Condns. (a) | Mp °C. | Elemental Analysis | LRMS | $^1H, \delta$ |
|---|---|---|---|---|---|---|---|
| 39 | Cl | 7-(2,6-dimethoxy-Ph) | 90° C., 18 h | 130–136 | Found C, 57.84; H, 5.14; N, 14.46. Calcd for $C_{18}H_{17}ClN_4O_2 + 0.25$ diethyl ether + water: C, 58.02; H, 5.51; N, 14.24 | 357, 359 (MH) | (DMSO-$d_6$, 300 MHz) 8.5 (1 H, s), 8.15–7.8 (2 H, m), 7.8–7.0 (5 H, m), 7.35 (1 H, t), 6.75 (2 H, d), 3.6 (6 H, s) |
| 40 | Cl | 7-(3,4-OCH$_2$O—Ph) | 90° C., 19 h | — | Found: C, 55.32; H, 3.89; N, 14.90. Calcd for $C_{17}H_{13}ClN_4O_2 + 0.5\ H_2O + 0.3\ CH_2Cl_2$: C, 55.37; H, 3.92; N, 14.93. | 341, 343 (MH) | (MeOH-$d_4$, 300 MHz) 4.6 (2 H, s), 5.5 (1 H, d), 5.8–5.9 (2 H, m), 6.5–6.65 (3 H, m), 7.3 (1 H, s) |
| 41 | Cl | 7-(3-CN—Ph) | 100° C., 18 h | >220° C. | Found: C, 59.85; H, 3.90; N, 19.94. Calcd for $C_{17}H_{12}ClN_5 + 0.8$ water + $0.1\ CH_2Cl_2$: C, 59.59; H, 4.04; N, 29.32 | 322 (MH), 339 (M + NH$_4$) | (DMSO-$d_6$, 300 MHz) 8.95 (1 H, s), 8.15 (1 H, s), 8.1 (1 H, d), 8.05 (1 H, d), 7.95 (1 H, s), 7.9 (1 H, d), 7.85 (1 H, d), 7.7 (1 H, t) |
| 42 | Cl | 7-(3-thienyl) | 100° C., 2.5 days | 211–3 | Found: C, 54.21; H, 3.66; N, 17.73. Calcd for $C_{14}H_{11}ClN_4S + 0.3$ MeOH + $0.07\ CH_2Cl_2$: C, 54.22; H, 3.91; N, 17.60. | 303, 305 (MH) | (DMSO-$d_6$, 400 MHz) 6.9–7.3 (4 H br s) 7.5–7.7 (2 H, m), 7.8–8.0 (3 H, m), 8.05 (1 H, d), 8.9 (1 H, s) |
| 43 | Cl | 7-(2-benzo-furanyl) | 100° C., 18 h | >220 | Found: C, 62.94; H, 3.78; N, 16.20. Calcd for $C_{18}H_{13}ClN_4O + 0.3\ H_2O + 0.03\ CH_2Cl_2$: C, 62.82; H, 3.99; N, 16.25. | 337, 339 (MH) | (DMSO-$d_6$, 400 MHz) 7.0–7.4 (4 H, br s), 7.25 (1 H, dd), 7.3 (1 H, dd), 7,45 (1 H, s), 7.6 (1 H, d), 7.65 (1 H, d), 7.9 (1 H, d), 7.95 (1 H, s), 8.25 (1 H, d), 9.1 (1 H, s) |
| 44 | Cl | 7-CH(OH)—Ph | 100° C., 8 h | 221.5–223 | Found: C, 60.87; H, 4.83; N, 16.01. Calcd. for $C_{17}H_{15}ClN_4O + 0.6\ H_2O + 0.1$ i-Pr$_2$O: C, 60.78; H, 5.10; N, 16.11. | 327, 329 (MH) | (MeOH-$d_4$, 300 MHz) 5.95 (1 H, s), 7.2–7.35 (3 H, m), 7.4 (2 H, d), 7.7 (1 H, d), 7.95 (1 H, d), 8.0 (1 H, s), 8.65 (1 H, s) |
| 45 | Br | 7-Br | 100° C., 2 days | — | Found: C, 34.88; H, 2.27; N, 16.01. Calcd for $C_{10}H_8Br_2N_4 + 0.06\ CH_2Cl_2$: C, 34.61; H, 2.34; N, 16.05. | 345 (MH) | (DMSO-$d_6$, 400 MHz) 6.8–7.4 (4 H, br s), 7.7 (1 H, d), 7.85 (1 H, d), 8.05 (1 H, s), 8.8 (1 H, s) |
| 46 | Br | 7-Ph | 100° C., 3 days | 205–7 | Found: C, 55.43; H, 3.73; N, 16.01. Calcd for $C_{16}H_{13}BrN_4 + 0.1\ CH_2Cl_2$: C, 55.30; H, 3.80; N, 16.02. | 342 (MH) | (DMSO-$d_6$, 300 MHz) 7.0–7.4 (4 H, br s), 7.4 (1 H, dd), 7.5 (2 H, dd), 7.75 (2 H, d), 7.85 (1 H, d), 8.0 (1 H, d), 8.05 (1 H, s), 8.95 (1 H, s) |
| 47 | Br | 7-(4-Me-Ph) | 100° C., 18 h | 203–5 | Found: C, 55.09; H, 4.11; N, 14.79. Calcd for $C_{17}H_{15}BrN_4 + 0.5\ H_2O + 0.11\ CH_2Cl_2$: C, 55.01; H, 4.38; N, 15.00. | 355, 357 (MH), 711 (M$_2$H) | (DMSO-$d_6$, 400 MHz) 2.3 (3 H, s) 6.8–7.4 (6 H, m), 7.6 (2 H, d), 7.8 (1 H, d), 8.0–8.05 (2 H, m), 8.9 (1 H, s) |
| 48 | Br | 7-(3-MeO—Ph) | 100° C., 18 h | 148–150 | Found: C, 53.29; H, 3.99; N, 14.33. Calcd. for $C_{17}H_{15}BrN_4O + 0.2\ CH_2Cl_2$: C, 53.21; H, 4.00; N, 14.43. | 371, 373 (MH) | (DMSO-$d_6$, 400 MHz) 3.8 (3 H, s), 6.95 (1 H, d), 7.0–7.3 (4 H, br s), 7.2 (1 H, s), 7.25 (1 H, d), 7.4 (1 H, dd), 7.8 (1 H, d), 8.0–8.05 (2 H, m), 8.9 (1 H, s) |
| 49 | Br | 7-(4-MeO—Ph) | 100° C., 18 h | 195–7 | Found: C, 53.89; H, 3.98; N, 14.59. Calcd for $C_{17}H_{15}BrN_4O + 0.1\ H_2O + 0.1\ CH_2Cl_2$: C, 53.83; H, 4.07; N, 14.68. | 371, 373 (MH) | (DMSO-$d_6$, 400 MHz) 3.75 (3 H, s), 7.05 (2 H, d), 6.9–7.3 (4 H, br s), 7.65 (2 H, d), 7.8 (1 H, d), 8.0 (1 H, d), 8.0 (1 H, s), 8.85 (1 H, s) |
| 50 | Br | 7-(3-Cl—Ph) | 100° C., 18 h | 183–5 | Found: C, 50.56; H, 3.21; N, 14.41. Calcd for $C_{16}H_{12}BrClN_4 + 0.1$ EtOAc + $0.06\ CH_2Cl_2$: C, 50.75; H, 3.34; N, 14.38. | 375, 377, 379 (MH) | (DMSO-$d_6$, 300 MHz) 7.0–7.3 (4 H, br s), 7.45 (1 H, d), 7.5 (1 H, dd), 7.7 (1 H, d), 7.75 (1 H, s), 7.8 (1 H, d), 8.05 (1 H, d), 8.1 (1 H, s), 8.95 (1 H, s) |

TABLE 1-continued (NB unless otherwise specified, substituents are H)

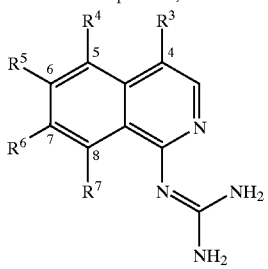

| Ex. | $R^3$ | $R^{4-7}$ | Rn. Condns. (a) | Mp ° C. | Elemental Analysis | LRMS | $^1H, \delta$ |
|---|---|---|---|---|---|---|---|
| 51 | — | 6,7-OCH$_2$O— | 100° C., 5 days | 171 dec | — | 231 (MH) | (DMSO-d$_6$, 300 MHz) 6.1 (2 H, s), 7.0 (1 H, d), 7.1 (1 H, s), 7.0–7.5 (4 H, br s), 7.8 (1 H, d), 7.9 (1 H, s) |

(a)Solvent DMSO unless otherwise specified.
(b)Isolated as a byproduct during the preparation of Example 27.
[References (c) to (h) relate to preparations of starting materials.]
(c)Robison, M. M.; Robison, B. L. J. Org. Chem. 1958, 23, 1071.
(d)Sanders, G. M.; van Dijk, M; den Hertog, H. J. Recl. Trav. Chim. Pays-Bas. 1974, 93, 298.
(e)Eloy, F.; Deryckere Helv. Chim. Acta. 1969, 52, 1755.
(f)Braye, R.; Eloy, F.; Hoogzand, C.; Lenaers, R. Eur. J. Med. Chem., Chim. Therap. 1974, 9, 197.
(g)Copp, F. C.; Franzmann, K. W.; Grundy, J.; Whalley, W. B. J Chem. Soc., Perkin Trans. I, 1985, 2455.
(h)Bevis, M. J.; Forbes, E. J.; Naik, N. N.; Uff; B. C. Tetrahedron, 1971, 27, 1253.

Example 52

3-Isoquinolinylguanidine and the bis (trifluoroacetate) salt thereof

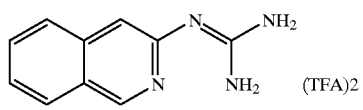

Mercury (II) chloride (192 mg, 0.707 mmol) was added in one portion to a stirred mixture of 3-aminoisoquinoline (84.5 mg, 0.586 mmol), N,N'-di-t-butoxycarbonyl-S-methylisothiourea (Bergeron, R. J.; McManis, J. S. J. Org. Chem. 1987, 52, 1700–1703) (204 mg, 0.703 mmol), and triethylamine (250 μL, 1.79 mmol) in CH$_2$Cl$_2$ (3.0 mL) under N$_2$ at 23° C. The mixture was stirred for 26 hours and then directly purified by column chromatography upon silica gel using hexanes-EtOAc (98:2 to 95:5) as eluant to give 3-(N',N''-di-t-butoxycarbonyl-N-guanidinyl)isoquinoline (189.4 mg, 0.492 mmol) as a white solid.

$^1$H NMR (δ, CDCl$_3$, 300 MHz) 1.55 (18, s), 7.45 (1H, dd), 7.65 (1H, dd), 7.85–7.9 (2H,m), 8.7 (1H, br s), 9.0 (1H, s), 10.5 (1H, br s), 11.6 (1H, br s);

LRMS 387 (MH).

Trifluoroacetic acid (2.5 mL) was added to a solution of 3-(N',N''-di-t-butoxycarbonyl-N-guanidinyl)isoquinoline (181 mg, 0.468 mmol) in CH$_2$Cl$_2$ (1.5 mL) and the mixture was stirred at room temperature for 2 h. The mixture was diluted with CH$_2$Cl$_2$ (5 mL) and the solvents were evaporated in vacuo to yield 3-isoquinolinylguanidine bis (trifluoroaceate) (186.9 mg, 0.449 mmol) as a white solid.

$^1$H NMR (δ, MeOH-d$_4$, 400 MHz) 4.8–5.0 (4H, br s), 7.4 (1H, s), 7.6 (1H, dd), 7.75 (1H, dd), 7.85 (1H, d), 8.05 (1H, d), 9.1 (1H, s);

LRMS 187 (MH);

Elemental Analysis: Found: C, 40.46; H, 2.77; N, 13.36. Calcd for C$_{10}$H$_{10}$N$_4$+2TFA: C, 40.59; H, 2.92; N, 13.52.

Example 53

(5-Hydroxyisoquinolin-1-yl)guanidine

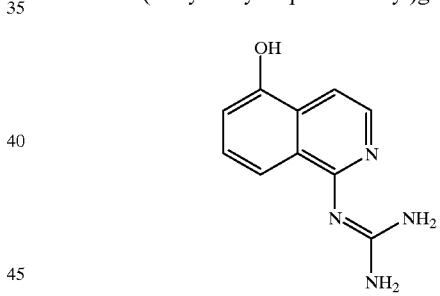

A solution of (5-benzyloxyisoquinolin-1-yl)guanidine (290 mg, 1.0 mmol) in EtOH (10 mL) containing 10% Pd-C (60 mg) and dilute HCl (1.5 mL, 2 M, 3.0 mmol) was stirred under an atmosphere of H$_2$ (4 atmospheres) at 60° C. for 3 d. An additional portion of catalyst (30 mg) and HCl (0.5 mL) were added and hydrogenation continued for a further 3 d. The mixture was filtered through Arbocel with EtOH rinsing, the filtrate was evaporated in vacuo and the residue purified by column chromatography upon silica gel using dichloromethane:methanol:0.88 ammonia (90:10:1 to 84:14:2) as eluant to give (5-hydroxyisoquinolin-1-yl) guanidine (66 mg, 0.33 mmol) as a white solid.

M.Pt.>150° C. dec.;

$^1$H NMR (δ, DMSO-d$_6$, 400 MHz) 3.0–3.4 (1H, br s), 7.05 (1H, d), 7.35 (1H, dd), 7.4–8.4 (3H, br s), 7.45 (1H, br s), 7.95 (1H, d), 8.1 (1H, d), 10.5–11.0 (1H, br s);

LRMS 203 (MH);

Elemental Analysis: Found: C, 52.00; H, 5.35; N, 23.00. Calculated for C$_{10}$H$_{10}$N$_4$O+0.66H$_2$O+0.3CH$_2$Cl$_2$: C, 51.64; H, 5.01; N, 23.38.

Example 54

(7-(4-Methoxyphenyl)isoquinolin-1-yl)guanidine

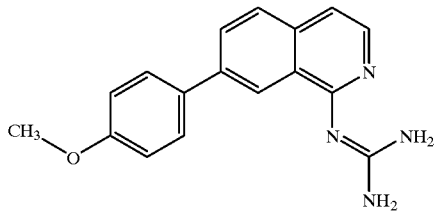

A solution of (4-bromo-7-(4-methoxyphenyl)isoquinolin-1-yl)guanidine (38 mg, 0.1 mmol) in industrial methylated spirits (2.0 mL) containing 5% Pd-C (10 mg) was stirred under an atmosphere of $H_2$ (3.5 atmospheres) at 23° C. for 3 days. The mixture was filtered through Arbocel™ with ethanol rinsing, the filtrate was evaporated in vacuo and the residue was purified by column chromatography on silica gel using dichloromethane:methanol:0.88 ammonia (97:3:0.3) as eluant to give (7-(4-methoxyphenyl)isoquinolin-1-yl)guanidine (24 mg, 0.08 mmol) as a white solid.

M.Pt. 174° C.;

$^1$H NMR (δ, DMSO-$d_6$, 400 MHz) 3.25 (4H, br s, exchangable), 3.8 (3H, br s), 7.05 (2H, d), 7.5–7.6 (1H, m) 7.85 (2H, d), 8.0 (1H, d), 8.05–8.15 (2H, m), 8.75 (1H, s);

LRMS 293 (MH).

Example 55

(7-(3-Carboxyphenyl)-4-chloroisoquinolin-1-yl)guanidine hydrochloride

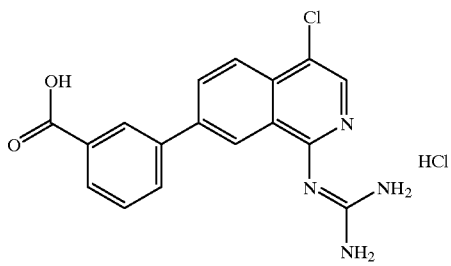

A solution of (4-chloro-7-(cyanophenyl)isoquinolin-1-yl)guanidine (69 mg, 0.21 mmol) in concentrated hydrochloric acid (10 ml) was heated to reflux for 20 hours. After cooling, the precipitate was filtered off, washed with water and dried under high vacuum at 80° C. to afford the title salt (55mg, 0.16 mmol) as an off-white powder.

M.Pt. 312–316° C.;

$^1$H NMR (δ, DMSO-$d_6$, 300 MHz) 13.4–11.2 (1H, br s), 9.4–7.8 (5H, br s), 9.2 (1H, s), 8.45–8.1 (5H, m), 8.0 (1H, d), 7.65 (1H, t);

LRMS 341, 343 (MH);

Elemental Analysis—Found: C, 53.25; H, 3.80; N, 14.28. Calcd for $C_{17}H_{14}Cl_2N_4O_2$+0.33 $H_2O$: C, 53.29; H, 3.86; N, 14.62.

Example 56

(i) 1-Guanidino-7-sulphamoylisoquinoline

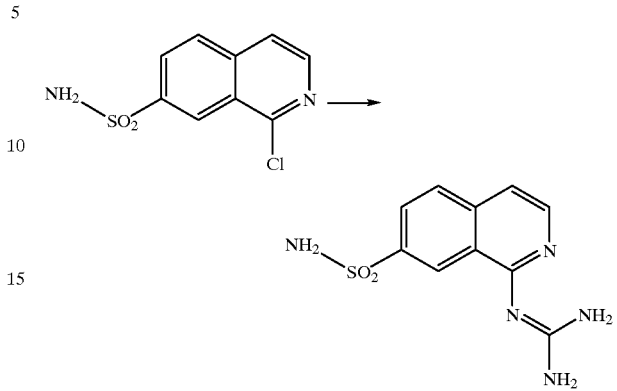

Guanidine hydrochloride (42 mg, 0.44 mmol) was added in one portion to a suspension of NaH (13 mg, 80% dispersion by wt in mineral oil, 0.43 mmol) in DMSO (1.5 mL) and the mixture was heated at 60° C. under $N_2$ for 30 min. 1-Chloro-7-isoquinolinesulphonamide (37 mg, 0.152 mmol) was added and the mixture heated at 100° C. for 24 h. The solvents were evaporated in vacuo and the residue was purified by column chromatography upon silica gel using $CH_2Cl_2$—MeOH-0.880$NH_3$ (97:3:0.3 to 90:10:1) as eluant to give the title compound (34 mg, 0.13 mmol) as an off-white solid.

mp 198–200° C. (dec).

$^1$H (DMSO-$d_6$, 400 MHz) δ7.0 (1H, d), 7.1–7.4 (4H, br s), 7.3 (2H, s), 7.8 (1H, d), 7.9 (1H, d), 8.0 (1H, d), 9.1 (1H, s) ppm.

LRMS 266 (MH$^+$).

Anal. Found: C, 41.38; H, 3.97; N, 24.09. Calc for $C_{10}H_{11}N_5O_2S.0.05CH_2Cl_2.1.1H_2O$: C, 41.72; H, 4.63; N, 24.20.

(ii) 1-Guanidino-7-sulphamoylisoquinoline dihydrochloride

1-Guanidino-7-sulphamoylisoquinoline (12 mg, 0.045 mmol) was dissolved in a solution of ethanol saturated with HCl gas (1.0 mL) and the mixture was stirred at room temperature for 1 hour. The solvents were evaporated in vacuo and the residue was azeotroped with dichloromethane ($CH_2Cl_2$) to give 1-guanidino-7-sulphamoylisoquinoline dihydrochloride (13 mg, 0.043 mmol) as a white solid.

$^1$H (DMSO-$d_6$, 400 MHz) δ7.6 (2H, s), 7.7 (1H, d), 8.2 (1H, s), 8.2 (1H, d), 8.3 (1H, d), 8.4–9.0(4H, br s), 9.1 (1H, d), 11.0 (1H,s) ppm.

Found: C, 34.80; H, 3.85; N, 19.68. Calc for $C_{10}H_{11}N_5O_2S.2HCl.0.5H_2O.0.1EtOH$: C, 34.82; H, 4.18; N, 19.91.

Example 57

1-Guanidino-7-phenylsulphamoylisoquinoline

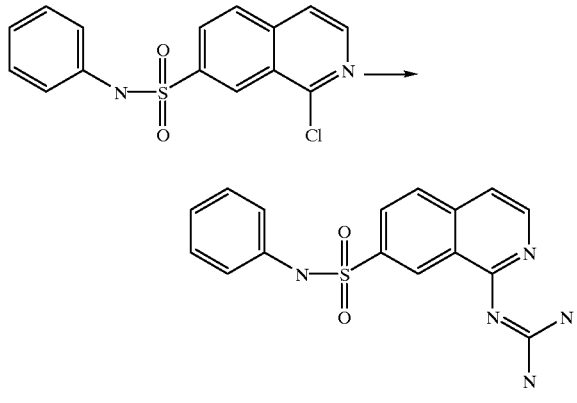

Guanidine hydrochloride (100 mg, 1.05 mmol) was added in one portion to a suspension of sodium hydride (NaH) (30 mg, 80% dispersion by wt. in mineral oil, 1.0 mmol) in dimethylsulphoxide (DMSO) (3.5 mL) and the mixture was heated at 60° C. under nitrogen ($N_2$) for 30 minutes. 1-Chloro-7-phenylsulphamoylisoquinoline (110 mg, 0.345 mmol) was added and the mixture was heated at 100° C. for 3 d. The solvents were evaporated in vacuo and the residue was purified by column chromatography (silica gel using $CH_2Cl_2$-methanol-0.880$NH_3$ (97:3:0.3 to 90:10:1) as eluant) to give 1-guanidino-7-phenylsulphamoylisoquinoline (16 mg, 0.047 mmol) as an off-white solid.

mp 186–188° C.

$^1$H (DMSO-$d_6$, 400 MHz) δ6.95 (2H, d), 7.05 (2H, d), 7.1–7.3 (4H, br s) 7.15–7.2 (2H, m), 7.7 (1H, d), 7.75 (1H, d), 8.0 (1H, d), 9.0 (1H, s), 10.2 (1H, s) ppm.

LRMS 341 (MH$^+$).

Found: C, 51.44; H, 4.14; N, 19.50. Calc for $C_{16}H_{15}N_5O_2S.0.1CH_2Cl_2.1.2H_2O$: C, 52.05; H, 4.78; N, 18.85.

Example 58

(i) 4-Chloro-1-guanidino-7-sulphamoylisoquinoline

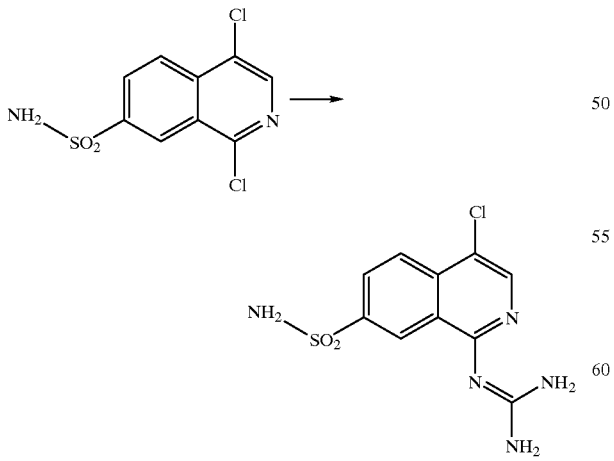

Guanidine hydrochloride (70 mg, 0.73 mmol) was added in one portion to a suspension of NaH (21 mg, 80% dispersion by wt in mineral oil, 0.66 mmol) in DMSO (2.0 mL) and the mixture was heated at 50° C. under $N_2$ for 30 min. 1,4-Dichloro-7-sulphamoylisoquinoline (70 mg, 0.25 mmol) was added and the mixture heated at 90° C. for 18 h. The cooled mixture was partitioned between ethyl acetate (EtOAc) and water, and the organic phase was washed with brine, dried (MgSO$_4$) and evaporated in vacuo. The residue was purified by column chromatography upon silica gel using $CH_2Cl_2$—MeOH-0.880$NH_3$ (95:5:0.5 to 90:10:1) as eluant to give 4-chloro-1-guanidino-7-sulphamoylisoquinoline (50 mg, 0.167 mmol) as a white solid.

mp 230° C. (dec).

$^1$H (DMSO-$d_6$, 300 MHz) δ7.1–7.5 (4H, br s), 7.4 (2H, br s), 8.0 (1H, d), 8.1 (1H, s), 8.15 (1H, d), 9.1 (1H, s) ppm.

LRMS 300, 302 (MH$^+$), 599 (M$_2$H$^+$).

Found: C, 39.49; H, 3.37; N, 22.63. Calc for $C_{10}H_{10}ClN_5O_2S.0.25H_2O$: C, 39.48; H, 3.48; N, 23.02.

(ii) 4-Chloro-1-guanidino-7-sulphamoylisoquinoline hydrochloride

4-Chloro-1-guanidino-7-isoquinolinesulphonamide (30 mg, 0.10 mmol) was dissolved in a solution of EtOH saturated with HCl gas (2.0 mL) and the mixture stirred at room temperature for 1 h. The solvents were evaporated in vacuo and the residue was azeotroped with $CH_2Cl_2$ to give 4-chloro-1-guanidino-7-isoquinolinesulphonamide hydrochloride (32 mg, 0.095 mmol) as a white solid.

mp 296° C. (dec).

$^1$H (DMSO-$d_6$, 400 MHz) δ7.6 (2H, s), 7.7 (1H, d), 8.2 (1H, s), 8.2 (1H, d), 8.3 (1H, d), 8.4–9.0 (4H, br s), 9.1 (1H, d), 11.0 (1H, s) ppm.

LRMS 300, 302 (MH$^+$), 599 (M$_2$H$^+$).

Found: C, 35.55; H, 3.26; N, 20.13. Calc for $C_{10}H_{10}ClN_5O_2S.1.0$ HCl0.05$CH_2Cl_2$: C, 35.46; H, 3.29; N, 20.57.

Example 59

4-Chloro-7-cyclopentylsulphamoyl-1-guanidinoisoquinoline

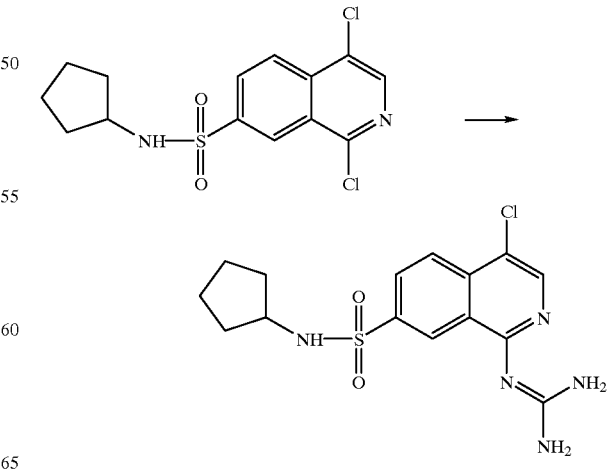

The title compound was prepared by same the general method as Example 56.

mp>250° C. (dec).

$^1$H (DMSO-d$_6$, 400 MHz) δ1.2–1.4 (4H, m), 1.4–1.6 (4H, m), 3.4 (1H, m), 7.7–7.8 (1H, br d), 8.0–8.2 (2H, m), 9.1 (1H, s) ppm.

LRMS 368 (MH$^+$).

Found: C, 48.23; H, 4.97; N, 18.44. Calc for C$_{15}$H$_{18}$ClN$_5$O$_2$S.0.1CH$_2$Cl$_2$: C, 48.19; H, 4.87; N, 18.61.

Example 60

4-Chloro-1-guanidino-7-(1-pyrrolidinosulphonyl) isoquinoline hydrochloride

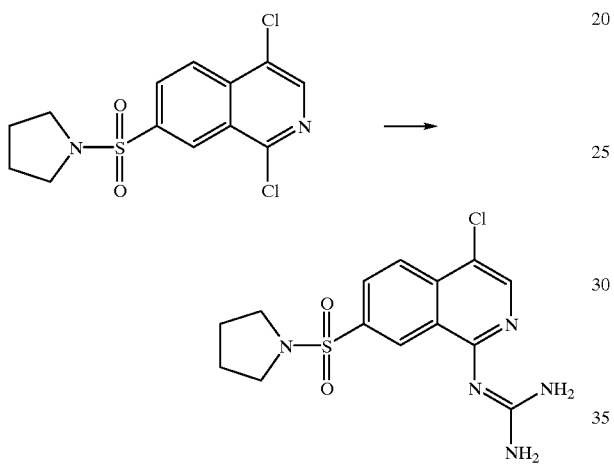

The title salt was prepared by same the general method as Example 56.

mp 299–300° C.

$^1$H (DMSO-d$_6$, 300 MHz) δ1.6–1.7 (4H, m), 3.2–3.3 (4H, m), 8.2–8.9 (4H, br s), 8.3 (1H, d), 8.4 (1H, d), 8.5 (1H, s), 9.1 (1H, s) ppm.

LRMS 354 (MH$^+$).

Found: C, 43.71; H, 4.69; N, 16.67. Calc for C$_{14}$H$_{16}$ClN$_5$O$_2$S.HCl.0.3EtOAc: C, 43.81 H, 4.69; N, 16.81.

Example 61

4-Chloro-1-guanidino-7-morpholinosulphonylisoquinoline hydrochloride

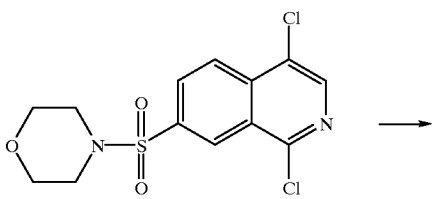

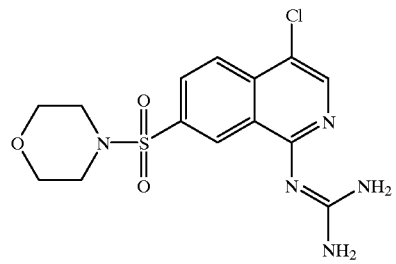

The title salt was prepared by same the general method as Example 56.

mp 285° C. (dec).

$^1$H (Trifluoracetic acid-d, 400 MHz) δ3.4 (4H, s), 4.1 (4H, s), 8.3 (1H, d), 8.5 (1H, s), 8.65 (1H, d), 9.1 (1H, s) ppm.

LRMS 370,372 (MH$^+$).

Found: C, 41.69; H, 4.32; N, 16.17. Calc for C$_{14}$H$_{16}$ClN$_5$O$_3$S.HCl.0.5MeOH: C, 41.24; H, 4.53; N, 16.58.

Example 62

4-Chloro-1-guanidino-7-[(N-methylpiperazino) sulphonyl]isoquinoline

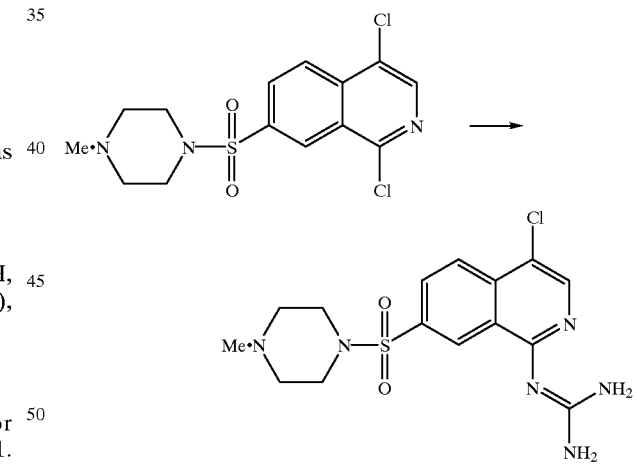

The title compound was prepared by same the general method as Example 56.

mp 262–263° C. (dec).

$^1$H (Trifluoracetic acid-d, 400 MHz) δ3.1 (3H, s), 3.3 (2H, m), 3.4 (2H, m), 3.9 (2H, m), 4.2 (2H, s), 8.3 (1H, d), 8.5 (1H, s), 8.7 (1H, d), 9.0 (1H, s) ppm.

LRMS 383, 385 (MH$^+$).

Found: C, 46.70; H, 4.99; N, 21.62. Calc for C$_{15}$H$_{19}$ClN$_6$O$_2$S.0.25MeOH: C, 46.86; H, 5.16; N, 21.50.

Example 63

4-Chloro-1-guanidino-7-(phenylsulphanyl)isoquinoline

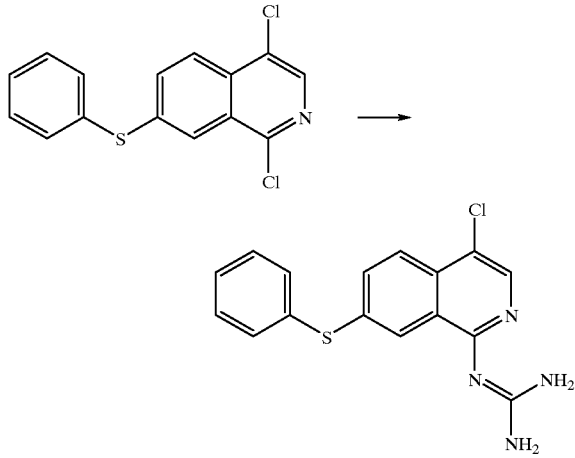

NaH (13.6 mg, 80% dispersion by wt in mineral oil, 0.45 mmol) was added in one portion to a solution of guanidine hydrochloride (44 mg, 0.46 mmol) in DMSO (2 mL) and the mixture was heated at 80° C. under $N_2$ for 10 min. 1,4-Dichloro-7-(phenylsulfanyl)isoquinoline (60 mg, 0.195 mmol) was added and the mixture heated at 80° C. for 1 h. The cooled mixture was poured into water (20 mL) and extracted with EtOAc (3×15 mL). The combined organic extracts were washed with brine, dried ($Na_2SO_4$) and evaporated in vacuo. The residue was extracted with hexanes-i-$Pr_2O$ and this organic solution was decanted, and then stirred with a solution of HCl in $Et_2O$ to give a precipitate. The white solid was collected by filtration and dried in vacuo to give 4-chloro-1-guanidino-7-(phenylsulphanyl)isoquinoline (51 mg, 0.13 mmol).

$^1$H (DMSO-$d_6$, 300 MHz) δ7.3–7.5 (5H, m), 7.7 (1H, d), 8.1–9.2 (4H, br s), 8.1 (1H, d), 8.3 (1H, s), 9.0 (1H, s), 11.3 (1H, s) ppm.

LRMS 329 (MH$^+$).

Anal. Found: C, 50.54; H, 3.95; N, 14.81. Calc for $C_{16}H_{13}ClN_4S.HCl.0.75H_2O$: C, 50.73; H, 4.12; N, 14.79.

Example 64

4-Chloro-1-guanidino-7-(phenylsulphonyl)isoquinoline

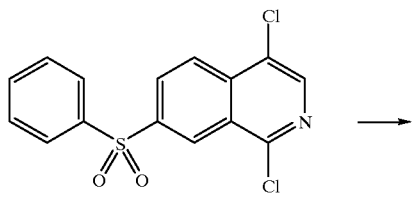

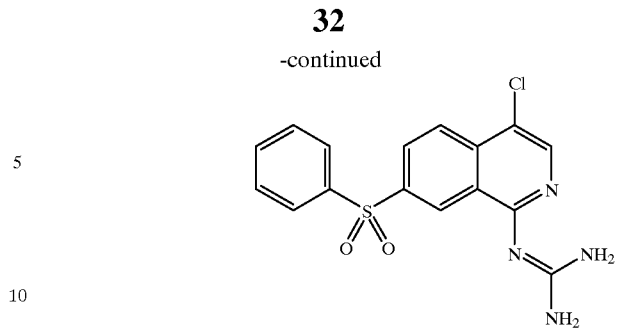

NaH (18 mg, 80% dispersion by wt in mineral oil, 0.60 mmol) was added in one portion to a solution of guanidine hydrochloride (90 mg, 0.94 mmol) in DMSO (2 mL) and the mixture was heated at 50° C. under $N_2$ for 30 min. 1,4-Dichloro-7-(phenylsulfonyl)isoquinoline (80 mg, 0.236 mmol) was added and the mixture heated at 50–60 C. for 0.5 h. The cooled mixture was poured into water (30 mL) and extracted with EtOAc (3×20 mL). The combined organic extracts were washed with brine, dried ($Na_2SO_4$) and evaporated in vacuo. The residue was dissolved in EtOAc and a solution of HCl in $Et_2O$ (1 M) was added which gave a precipitate. The solvents were evaporated in vacuo and the residue triturated with EtOAc to give 4-chloro-1-guanidino-7-(phenylsulphonyl)isoquinoline (65 mg, 0.18 mmol) as a yellow solid.

$^1$H (DMSO-$d_6$, 400 MHz) δ7.6–7.75 (3H, m), 8.1–9.2 (4H, br s), 8.2 (2H, d), 8.35 (1H, d), 8.4 (1H, d), 8.45 (1H, s), 9.5 (1H, s), 11.7 (1H, s) ppm.

LRMS 361 (MH$^+$).

Anal. Found: C, 48.17; H, 3.75; N, 13.16. Calc for $C_{16}H_{13}ClN_4O_2S.HCl.0.25H_2O.0.2EtOAc$: C, 48.11; H, 3.87; N, 13.36.

Preparation 1: 4,7-Dibromoisoquinoline

Bromine (2.77 mL, 53.8 mmol) was added dropwise over 20 min. to a stirred suspension of a 1:1 mixture of 5- and 7-bromoisoquinoline hydrochlorides (prepared by cyclisation of dimethyl(3-bromobenzylidene)aminoacetal according to the procedure of F. T. Tyson *J. Am. Chem. Soc.* 1939, 61, 183-5) (11.43 g, 48.2 mmol) in nitrobenzene (12.5 mL) and the mixture was heated at 170° C. for 5 h. The mixture was cooled to 80° C., diluted with toluene (50 mL) which gave a precipitate and left at 23° C. overnight. The mother liquors were decanted with toluene rinsing (2×20 mL). The solid was digested in aqueous sodium hydroxide (100 mL, 1 M), extracted with ether (3×100 mL) and the ether phase was dried over magnesium sulphate ($MgSO_4$) and concentrated in vacuo. The residue was purified by column chromatography upon silica gel using hexanes-EtOAc (96:4 to 80:20) as eluant to give 4,7-dibromoisoquinoline (5.91 g, 20.6 mmol) as a white solid.

M.Pt. 107–110° C.;

$^1$H NMR (δ, CDCl$_3$, 300 MHz) 7.9 (1H, d), 8.05 (1H, d), 8.15 (1H, s), 8.75 (1H, s), 9.1 (1H, s);

LRMS 285, 287 (MH);

Elemental Analysis—Found: C, 37.90; H, 1.67; N, 4.83. Calculated for $C_9H_5Br_2N$: C, 37.67; H, 1.76; N, 4.88.

Preparation 2: 4-Bromo-7-phenylisoquinoline

A mixture of 4,7-dibromoisoquinoline (556 mg, 1.93 mmol), tetrakis(triphenylphosphine)-palladium(0) (73 mg, 3 mol %), phenylboronic acid (238 mg, 1.95 mmol), and aqueous sodium carbonate ($Na_2CO_3$) (3.9 mL, 1.0 M, 3.9 mmol) in DME (12 mL) was heated at reflux under nitrogen for 20 h. The mixture was diluted with ethyl acetate (EtOAc) (100 mL), washed with water (30 mL), dried over MgSO$_4$ and evaporated in vacuo. The residue was purified by column chromatography upon silica gel using hexanes-EtOAc (95:5 to 80:20) as eluant to give 4-bromo-7-phenylisoquinoline (389 mg, 1.37 mmol) as a straw-colour solid; $^1$H ($\delta$, CDCl$_3$, 300 MHz) 7.4–7.6 (3H, m), 7.65–7.75 (2H, m), 8.1 (1H, d), 8.15 (1H, s), 8.2 (1H, d), 8.7 (1H, s), 9.2 (1H, s); LRMS 283, 284, 286.

Preparation 3: 7-Bromo-1,4-dichloroisoquinoline (i) A solution of 4-bromocinnamic acid (5.03 g, 22.2 mmol) in thionyl chloride (SOCl$_2$) (15 mL) was stirred at 23° C. for 16 h, and then heated at reflux for a further 2 h. The solvents were evaporated in vacuo and the residue azeotroped with toluene (×3) to yield 4-bromocinnamoyl chloride as an orange-brown solid in quantitative yield.

$^1$H NMR ($\delta$, CDCl$_3$, 300 MHz) 6.65 (1H, d), 7.4 (2H, d), 7.6 (2H, d), 7.8 (1H, d).

(ii) A solution of sodium azide (NaN$_3$) (2.2 g, 33.8 mmol) in water (7.5 mL) was added dropwise over 5 min to a stirred solution of 4-bromocinnamoyl chloride (22.2 mmol) in acetone (22 mL) at –10° C. The heterogeneous mixture was stirred at 0° C. for 1 h and diluted with water (25 mL). The precipitate was collected by filtration and dried in vacuo over phosphorus pentoxide (P$_2$O$_5$) to give 4-bromocinnamoyl azide (5.22 g, 20.7 mmol) as a golden-coloured solid.

$^1$H NMR ($\delta$, CDCl$_3$, 300 MHz) 6.4 (1H, d), 7.4 (2H, d), 7.5 (2H, d), 7.65 (1H, d).

(iii) [NB This stage is potentially explosive—take care and use a blast screen.] A warm solution of 4-bromocinnamoyl azide (5.22 g, 20.7 mmol) in diphenyl ether (Ph$_2$O) (25 mL) was added dropwise over 15 min to stirred Ph$_2$O (10 mL) at 270° C. The mixture was heated at 270° C. for 1.5 h, cooled to 23° C. and then poured into hexanes (400 mL). The precipitate was collected by filtration with hexanes (2×100 mL) rinsing and purified by column chromatography upon silica gel using hexanes-EtOAc (6:4 to 100% EtOAc) as eluant to give 7-bromoisoquinolone (1.64 g, 7.3 mmol) as a white solid.

$^1$H NMR ($\delta$, DMSO-d$_6$, 300 MHz) 6.55 (1H, d), 7.25–7.15 (1H, m), 7.6 (1H, d), 7.8 (1H, d), 8.25 (1H, s), 11.4 (1H, br s).

(iv) A mixture of 7-bromoisoquinolone (1.28 g, 5.69 mmol) and PCl$_5$ (2.04 g, 9.80 mmol) was heated at 140° C. for 5 h. The cooled mixture was quenched with ice (50 g) and 0.880 ammonia was added until alkaline by litmus paper. The aqueous mixture was extracted with dichloromethane (3×50 mL) and the combined organic phases were dried over MgSO$_4$ and evaporated in vacuo. The residue was purified by column chromatography upon silica gel using hexanes-EtOAc (97:3 to 95:5) as eluant to give 7-bromo-1,4-dichloroisoquinoline (1.13 g, 4.08 mmol) as a white solid.

M.Pt. 133.5–135° C.;

$^1$H ($\delta$, CDCl$_3$, 300 MHz) 7.9 (1H, d), 8.1 (1H, d), 8.35 (1H, s), 8.5 (1H, s);

LRMS 276, 278 (MH);

Elemental Analysis—Found: C, 39.04; H, 1.32; N, 5.06. Calcd for C$_9$H$_4$BrCl$_2$N: C, 39.03; H, 1.46; N, 5.06.

Preparation 4: 6-Bromoisoquinoline N-oxide

Acetic acid (8 mL) and 30% hydrogen peroxide (4 mL) were heated at 80° C. for 1 h. The cooled solution of peracetic acid was added to 6-bromoisoquinoline (Tyson, F. T. *J. Am. Chem. Soc.*, 1939, 61, 183) (0.389 g, 1.87 mmol) and the mixture was then heated at 80° C. for 18 h. The mixture was diluted with water (15 mL) and concentrated in vacuo to ca. half the volume and the residue was extracted with CH$_2$Cl$_2$ (2×25 mL). The combined organics were washed with saturated aqueous NaHCO$_3$ (25 mL), dried over MgSO$_4$ and evaporated to leave an oil. Azeotroping with PhMe (×3) and then CH$_2$Cl$_2$ (×3) gave 6-bromoisoquinoline N-oxide (0.420 g, quant) as a cream-coloured solid. $^1$H ($\delta$, CDCl$_3$, 300 MHz) 7.6–7.65 (2H, m), 7.77 (1H, dd), 8.0 (1H, s), 8.2 (1H, dd), 8.85 (1H, s);

LRMS 223, 226 (MH).

The following compounds of Preparations 5 to 8 were prepared in a similar manner:

Preparation 5: (i) 5-Bromoisoquinoline N-oxide and (ii) 7-bromoisoquinoline N-oxide The title compounds (1:1, mixture) were prepared from a 1:1 mixture of 5-bromoisoquinoline and 7-bromoisoquinoline, as a white powder.

M.Pt. 149–151° C.;

$^1$H NMR ($\delta$, CDCl$_3$, 300 MHz) 7.5 (1H, dd), 7.6–7.7 (4H, m), 7.85 (1H, d), 7.9 (1H, d), 8.1 (1, dd), 8.2 (1H, dd), 8.7 (1H, s), 8.75 (1H, s);

LRMS 224 (MH).

Preparation 6: (i) 5-Cyanoisoquinoline N-oxide and (ii) 7-cyanoisoquinoline N-oxide The title compounds (1:1, mixture) were prepared from a 1:1 mixture of 5-cyanoisoquinoline and 7-cyanoisoquinoline (Tyson, F. T. *J. Am. Chem. Soc.*, 1939, 61, 183), as a pale yellow powder.

$^1$H NMR ($\delta$, DMSO-d$_6$, 300 MHz) 7.8 (1H, dd), 7.85 (1H, d), 7.95 (1H, d), 8.05 (1H, d), 8.1 (1H, d), 8.15 (1H, s), 8.2 (1H, s), 8.25–8.35 (2H, m), 8.45 (1H, s), 9.0 (1H, s), 9.1 (1H, s);

LRMS 171 (MH), 341 (M$_2$H).

Preparation 7: 4,7-Dibromoisoquinoline N-oxide

The title compound was prepared from 4,7-dibromoisoquinoline.

$^1$H ($\delta$, DMSO-d$_6$, 300 MHz) 7.85 (1H, d), 7.9 (1H, d), 8.25 (1H, s), 8.65 (1H, s), 8.95 (1H, s);

LRMS 302, 303, 305, 306 (MH).

Preparation 8: 4-Bromo-7-phenylisoquinoline N-oxide

The title compound was prepared from 4-bromo-7-phenylisoquinoline as a lemon-coloured solid.

$^1$H NMR ($\delta$, DMSO-d$_6$, 300 MHz) 7.4–7.6 (3H, d), 7.75–7.85 (2H, m), 8.05 (2H, s), (2H, s), 8.25 (1H, s), 8.6 (1H, s), 9.0 (1H, s);

LRMS 299, 301 (MH).

Preparation 9: 7-Benzyloxyisoquinoline N-oxide

A solution of 7-benzyloxyisoquinoline (International Patent Application publication no. WO 94/20459) (0.50 g, 2.13 mmol) in CH$_2$Cl$_2$ (20 mL) was stirred with 3-chloroperbenzoic acid (mCPBA) (1.1 g, 3.19 mmol) at room temperature for 2.5 h. The mixture was diluted with CH$_2$Cl$_2$, and then washed with sodium dithionite (1 M), potassium carbonate (1 M) and brine. The organic layer was dried over MgSO$_4$ and evaporated in vacuo to leave 7-benzyloxyisoquinoline N-oxide (0.521 g, 2.09 mmol) as a cream-coloured powder.

$^1$H ($\delta$, CDCl$_3$, 400 MHz) 5.15 (2H, s), 7.25 (1H, d), 7.3–7.5 (5H, m), 7.55 (1H, d), 8.6 (1H, s); d), 8.0 (1H, d), 8.6 (1H, s);

LRMS 252 (MH).

The following compounds of Preparations 10–14 were prepared in a similar manner:

Preparation 10: 5-(Ethoxycarbonylmethoxy)isoquinoline N-oxide

The title compound was prepared from 5-(ethoxycarbonylmethoxy)isoquinoline (see British Patent application publication no. GB 2065121 A) as a tan-coloured solid.

¹H NMR (δ, CDCl₃, 400 MHz) 1.3 (3H, t), 4.2 (2H, q), 4.8 (2H, s), 6.8 (1H, d), 7.3 (1H, d), 7.4 (1H, dd), 8.05–8.15 (2H, m), 8.7 (1H, s);
LRMS 248 (MH).

Preparation 11: 5-Benzyloxyisoquinoline N-oxide

The title compound was prepared from 5-benzyloxyisoquinoline (see Japanese Patent application JP 51070772) as a yellow solid.
¹H (δ, CDCl₃, 400 MHz) 5.2 (2H, s), 6.95 (1H, d), 7.25 (1H, d), 7.3–7.5 (6H, m), 8.1 (2H, s), 8.7 (1H, s);
LRMS 252 (MH).

Preparation 12: 5-Phenylisoquinoline N-oxide

The title compound was prepared from 5-phenylisoquinoline (Pridgen, L. N. *J. Het. Chem.* 1980, 17, 1289) as a yellow viscous oil.
¹H NMR (δ, DMSO-d₆, 400 MHz) 7.4–7.5 (6H, m), 7.6 (1H, d), 7.7 (1H, dd), 7.9 (1H, d), 8.1 (1H, d), 9.0 (1H, s);
LRMS 222 (MH).

Preparation 13: 6-Methylisoquinoline N-oxide

The title compound was prepared from 6-methylisoquinoline (Brown, E. V. *J. Org. Chem.* 1977, 42, 3208) as an off-white solid.
¹H (δ, DMSO-d₆, 300 MHz) 2.5 (3H, s), 7.5 (1H, d), 7.7 (1H, s), 7.75–7.85 (2H, m), d), 8.85 (1H, s);
LRMS 160 (MH), 319 (M₂H).

Preparation 14: 6,7-(Methylenedioxy)isoquinoline N-oxide

The title compound was prepared from 6,7-(methylenedioxy)isoquinoline (P.Fritsch, *Ann.* 1895, 286, 1) as a cream-coloured solid.
¹H (δ, DMSO-d₆, 400 MHz) 6.1 (2H, s), 7.05 (1H, s), 7.15 (1H, s), 7.7 (1H, d), 8.0 (1H, d), 8.7 (1H, s);
LRMS 190 (MH), 379 (M₂H).

Preparation 15: 6-Bromo-1-chloroisoquinoline

Phosphorus oxychloride (0.60 mL, 6.44 mmol) was added in one portion to a stirred solution of 6-bromoisoquinoline N-oxide (409 mg, 1.83 mmol) in CH₂Cl₂ (10 mL) and the mixture was heated at reflux for 6 hours. Excess solvents were evaporated in vacuo, the residue suspended in water (10 mL) and basified with 0.880 ammonia. This mixture was extracted with CH₂Cl₂ (2×25 mL) and the combined organics were dried over MgSO₄ and evaporated in vacuo to leave the crude product. Purification by column chromatography upon silica gel using hexanes-EtOAc (90:10) as eluant gave 6-bromo-1-chloroisoquinoline (215 mg, 0.86 mmol) as a cream-coloured solid.
M.Pt. 105–107° C.;
¹H (δ, CDCl₃, 300 MHz) 7.5 (1H, d), 7.75 (1H, dd), 8.05 (1H, d), 8.2 (1H, d), 8.3 (1H, d);
LRMS 244 (MH);
Elemental Analysis—Found: C, 44.50; H, 1.98; N, 5.73. Calcd for C₉H₅BrClN: C, 44.58; H, 2.08; N, 5.78.

The compounds of Preparations 16–25 listed below were prepared similarly from the corresponding N-oxides from Preparation 15:

Preparation 16: 1-Chloro-5-(ethoxycarbonylmethoxy)isoquinoline

The title compound was prepared from 5-(ethoxycarbonylmethoxy)isoquinoline N-oxide as a white solid.
M.Pt. 52–4° C.;
¹H NMR (δ, CDCl₃, 300 MHz) 1.3 (3H, t), 4.3 (2H, q), 4.8 (2H, s), 7.0 (1H, d), 7.65 (1H, dd), 7.9 (1H, d), 8.1 (1H, d), 8.3 (1H, d);
LRMS 265 (MH);
Elemental Analysis—Found: C, 58.70; H, 4.48; N, 5.18. Calcd for C₁₃H₁₂ClNO₃: C, 58.77; H, 4.48; N, 5.18.

Preparation 17: 5-Benzyloxy-1-chloroisoquinoline

The title compound was prepared from 5-benzyloxyisoquinoline N-oxide as a white solid.
M.Pt. 95–96° C.;
¹H (δ, CDCl₃, 300 MHz) 5.2 (2 H,s), 7.1 (1H, d), 7.3–7.5 (5H, m), 7.55 (1H, dd), 7.85 (1H, d), 8.0 (1H, d), 8.2 (1H, d);
LRMS 270,272 (MH);
Elemental Analysis—Found: C, 71.18; H, 4.43; N, 5.09. Calcd for C₁₆H₁₂ClNO: C, 71.25; H, 4.48; N, 5.19.

Preparation 18: 1-Chloro-5-phenylisoquinoline

The title compound was prepared from 5-phenylisoquinoline N-oxide as an oil.
¹H NMR (CDCl₃, 400 MHz) 7.35–7.55 (5H, m), 7.6–7.75 (3H, m), 8.2 (1H, d), 8.35 (1H, d);
LRMS 240, 242 (MH);
El.Anal. Found: C, 74.66; H, 4.17; N, 5.81. Calcd for C₁₅H₁₀ClN+0.1 H₂O: C,74.66; H, 4.26; N, 5.80.

Preparation 19: 1-Chloro-6-methylisoquinoline

The title compound was prepared from 6-methylisoquinoline N-oxide, as a straw-coloured solid.
¹H NMR (δ, CDCl₃, 300 MHz) 2.6 (3H, s), 7.45–7.6 (2H, m), 7.6 (1H, s), 8.2–8.3 (2H, m);
LRMS 178, 180 (MH).

Preparation 20: 7-Bromo-1-chloroisoquinoline

The title compound was prepared from a mixture of 5- and 7-bromoisoquinoline N-oxides and separated from 5-bromo-1-chloroisoquinoline by chromatography, to give a white solid.
¹H (δ, CDCl₃, 300 MHz) 7.5 (1H, d), 7.7 (1H, d), 7.8 (1H, d), 8.3 (1H, d), 8.5 (1H, s);
LRMS 244, 246 (MH).

Preparation 21: 1-Chloro-7-cyanoisoguinoline

The title compound was prepared from a mixture of 5- and 7-cyanoisoquinoline N-oxides and separated from 1-chloro-5-cyanoisoquinoline by chromatography, to give a white powder.
¹H (δ, CDCl₃, 400 MHz) 7.7 (1H, d), 7.9 (1H, d), 7.95 (1H, d), 8.45 (1H, d), 8.75 (1H, s);
LRMS 189 (MH).

Preparation 22: 7-Benzyloxy-1-chloroisoquinoline

The title compound was prepared from 7-benzylisoquinoline N-oxide, giving a white powder.
M.Pt. 128–31° C.;
¹H (δ, CDCl₃, 400 MHz) 5.2 (2H, s), 7.3–7.5 (7H, m), 7.65 (1H, s), 7.75 (1H, d), 8.35 (1H, d);
LRMS 270, 272 (MH);
El.Anal. Found: C, 71.04; H, 4.47; N, 5.12. Calcd for C₁₆H₁₂ClNO: C, 71.25; H, 4.48; N, 5.19.

Preparation 23: 1-Chloro-4,7-dibromoisoquinoline

The title compound was prepared from 4,7-dibromoisoquinoline N-oxide as a white solid.
¹H (δ, CDCl₃, 400 MHz) 7.9 (1H, dd), 8.05 (1H, d), 8.45 (1H, s), 8.5 (1H, d);
LRMS 321 (MH).

Preparation 24: 4-Bromo-1-chloro-7-phenylisoquinoline

The title compound was prepared from 4-bromo-7-phenylisoquinoline N-oxide as a white solid.
M.Pt. 144–7° C.;
¹H (δ, CDCl₃, 300 MHz) 7.4–7.6 (3H, m), 7.7–7.75 (2H, m), 8.1 (1H, d), 8.45 (1H, s), 8.5 (1H, s);
LRMS 321 (MH);
El.Anal. Found: C, 56.71; H, 2,89; N, 4.30. Calcd for C₁₅H₉BrClN: C, 56.55; H, 2.85; N, 4.40.

Preparation 25: 1-Chloro-6,7-(methylenedioxy)isoquinoline

The title compound was prepared from 6,7-(methylenedioxy)isoquinoline N-oxide as a cream solid.

$^1$H NMR (δ, CDCl$_3$, 300 MHz) 6.15 (2H, s), 7.05 (1H, s), 7.4 (1H, d), 7.6 (1H, s), 8.1 (1H, d);

LRMS 207, 210 (MH).

Preparation 26: 3,5-dimethoxyphenylboronic acid

To 1-bromo-3,5-dimethoxybenzene (1.4 g, 6.45 mmol) (Dean, N. B; Whalley, W. B. *J. Chem. Soc.* 1954, 4638) in THF (60 mL) under nitrogen at −70° C. was added n-BuLi (2.6 mL, 2.5M in hexanes). After 10 min. the clear yellow solution was treated with trimethyl borate (1.5 mL, 13.2 mmol) in THF (2 mL) and stirred for a further hour, allowed to warm to room temperature over 3 hours and quenched with water (10 mL). After dilution with water (50 mL) the mixture was extracted with methylene chloride (×2). The combined organics were washed with brine and concentrated to an off-white solid which was recrystallised from diethyl ether to give a white solid (400 mg, 2.2 mmol).

M.Pt. 195–7° C.;

$^1$H NMR (δ, DMSO-d$_6$, 400 MHz) 3.7 (3H, s), 3.75 (3H, s), 6.45–6.5 (1H, m), 6.85–6.95 (2H, m);

LRMS 183 (MH).

Preparation 27: 1,4-Dichloro-7-(4-methylphenyl)isoquinoline

A mixture of 7-bromo-1,4-dichloroisoquinoline (276 mg, 1.0 mmol), tetrakis(triphenylphosphine)palladium(0) (60 mg, 5 mol %), 4-methylphenylboronic acid (137 mg, 1.00 mmol), and aqueous Na$_2$CO$_3$ (2.0 mL, 1.0 M, 2.0 mmol) in DME (6 mL) was heated at reflux under N$_2$ for 20 h. The mixture was diluted with EtOAc (100 mL), washed with water (30 mL), dried over MgSO$_4$ and evaporated in vacuo. The residue was purified by column chromatography upon silica gel using hexanes-EtOAc (99:1 to 97:3) as eluant to give 1,4-dichloro-7-(4-methylphenyl)isoquinoline (139 mg, 0.48 mmol) as a solid.

$^1$H (δ, CDCl$_3$, 300 MHz) 2.45 (3H, s), 7.35 (2H, d), 7.65 (2H, d), 8.1 (1H, s), 8.5 (1H, d); 8.3 (1H, s), 8.5 (1H, d).

LRMS 288, 290, 292 (MH).

The following compounds of Preparations 28–41 were prepared similarly:

Preparation 28: 1-Chloro-7-phenylisoquinoline

The title compound was prepared from 7-bromo-1-chloroisoquinoline and phenylboronic acid, as an oil.

$^1$H (δ, CDCl$_3$, 400 MHz) 7.4–7.55 (3H, m), 7.65 (1H, d), 7.75 (2H, d), 7.9 (1H, d), 8.05 (1H, d), 8.3 (1H, d), 8.55 (1H, s);

LRMS 240 (MH).

Preparation 29: 1-Chloro-7-(3,4-methylenedioxyphenyl)isoquinoline

The title compound was prepared from 7-bromo-1-chloroisoquinoline and 3,4-methylenedioxyphenylboronic acid (Banwell, M. G.; Cowden, C. J. *Aust. J. Chem.* 1994, 47, 2235), as a white powder.

$^1$H (δ, CDCl$_3$, 400 MHz) 6.1 (2H, s), 7.05 (1H, d), 7.3 (1H, d), 7.4 (1H, s), 7.9 (1H, d), 8.1 (1H, d), 8.15 (1H, d), 8.25 (1H, d), 8.3 (1H, s);

LRMS 284, 286 (MH);

El.Anal. Found: C, 67.54; H, 3.51; N, 4.87. Calcd for C$_{16}$H$_{10}$ClNO$_2$: C, 67.74; H, 3.55; N, 4.94.

Preparation 30: 7-(2-Benzofuranyl)-1,4-dichloroisoquinoline

The title compound was prepared from 7-bromo-1,4-dichloroisoquinoline and benzo[b]furan-2-boronic acid as a yellow solid.

M.Pt. 162° C.;

$^1$H (δ, CDCl$_3$, 400 MHz) 7.25–7.3 (2H, m), 7.3 (1H, dd), 7.55–7.65 (2H, m), 8.25 (2H, d), 8.3 (1H, d), 8.75 (1H, s);

LRMS 316 (MH);

El.Anal. Found: C, 62.93; H, 2.79; N, 4.33. Calcd for C$_{17}$H$_9$Cl$_2$NO: C, 63.21; H, 2.97; N, 4.32.

Preparation 31: 1,4-Dichloro-7-(3-thienyl)isoquinoline

The title compound was prepared from 7-bromo-1,4-dichloroisoquinoline and thiophene-3-boronic acid, as a yellow solid.

M.Pt. 109° C.;

$^1$H (δ, CDCl$_3$, 400 MHz) 7.45 (1H, d), 7.5 (1H, d), 7.7 (1H, s), 8.1 (1H, d), 8.2 (1H, d), 8.3 (1H, s), 8.45 (1H, s);

LRMS 280, 282 (MH).

Preparation 32: 1,4-Dichloro-7-(2-methoxyphenyl)isoquinoline

The title compound was prepared from 7-bromo-1,4-dichloroisoquinoline and 2-methoxyphenylboronic acid as a pale cream solid.

$^1$H (δ, CDCl$_3$, 400 MHz) 3.8 (3H, s), 7.05 (1H, d), 7.1 (1H, dd), 7.35–7.45 (2H, m), 8.05 (1H, d), 8.2 (1H, d), 8.3 (1H, s), 8.4 (1H, s);

LRMS 304, 306 (MH).

Preparation 33: 1,4-Dichloro-7-(3-methoxyphenyl)isoquinoline

The title compound was prepared from 7-bromo-1,4-dichloroisoquinoline and 3-methoxyphenylboronic acid as a pale cream solid.

$^1$H (δ, CDCl$_3$, 300 MHz) 3.95 (3H, s), 7.0 (1H, d), 7.25 (1H, s), 7.3 (1H, d), 7.45 (1H, dd), 8.1 (1H, dd), 8.25 (1H, d), 8.35 (1H, s), 8.5 (1H, s);

LRMS 304, 306, 308 (MH).

Preparation 34: 1,4-Dichloro-7-(4-methoxyphenyl)isoquinoline

The title compound was prepared from 7-bromo-1,4-dichloroisoquinoline and 4-methoxyphenylboronic acid as a pale yellow solid.

M.Pt. 124–6° C.;

$^1$H (δ, CDCl$_3$, 400 MHz) 3.9 (3H, s), 7.05 (2H, d), 7.7 (2H, d), 8.1 (1H, d), 8.25 (1H, d), 8.3 (1H, d), 8.45 (1H, s);

LRMS 304, 306, 308 (MH);

El.Anal. Found: C, 62.28; H, 3.56; N, 4.46. Calcd for C$_{16}$H$_{11}$Cl$_2$NO+0.05 CH$_2$Cl$_2$: C, 62.50; H, 3.63; N, 4.54.

Preparation 35: 1,4-Dichloro-7-(3,4-methylenedioxyphenyl)isoquinoline

The title compound was prepared from 7-bromo-1,4-dichloroisoquinoline and 3,4-methylenedioxyphenylboronic acid as a solid.

$^1$H (δ, DMSO-d$_6$, 300 MHz) 6.1 (2H, s), 7.1 (1H, d), 7.35 (1H, d), 7.45 (1H, s), 8.25 (1H, d), 8.35 (1H, d), 8.4 (1H, s), 8.45 (1H, s);

LRMS 318, 320 (MH).

Preparation 36: 1,4-Dichloro-7-(3,5-dimethoxyphenyl)isoquinoline

The title compound was prepared from 7-bromo-1,4-dichloroisoquinoline and 3,5-dimethoxyphenylboronic acid as an off-white solid.

M.Pt. 140–2° C.; $^1$H (δ, CDC$_3$, 400 MHz) 3.85 (6H, s), 6.55 (1H, s), 6.8 (2H, s), 8.1 (1H, d), 8.25 (1H, d), 8.3 (1H, s), 8.5 (1H, s);

LRMS 333, 335, 337 (MH);

El.Anal. Found: C, 61.17; H, 4.05; N, 3.78. Calcd for C$_{17}$H$_{13}$Cl$_2$NO$_2$+0.14 EtOAc: C, 60.86; H, 4.11; N, 4.04.

Preparation 37: 7-(3-Cyanophenyl)-1,4-dichloroisoquinoline

The title compound was prepared in a similar manner to Preparation 42, from 7-bromo-1,4-dichloroisoquinoline and 3-cyanophenylboronic acid (International Patent Application publication no. WO94/11372) to give a white solid.

M.Pt. 197–199° C.;

$^1$H NMR (δ, CDCl$_3$, 300MHz) 8.5 (1H,s), 8.4 (1H,s), 8.3 (1H,d), 8.1 (1H,d), 8.0 (1H,s), 7.95 (1H,d), 7.7 (1H,d), 7.65 (1H,d);

LRMS 298,300;

El.Anal. Found C, 64.01; H, 2.67; N, 9.20. Calcd for C$_{16}$H$_8$Cl$_2$N$_2$: C, 64.24; H, 2.70; N, 9.36.

Preparation 38: 4-Bromo-1-chloro-7-(3-chlorophenyl) isoquinoline

The title compound was prepared in a similar manner to Preparation 42, from 1-chloro-4,7-dibromoisoquinoline and 3-chlorophenylboronic acid as a white solid.

M.Pt. 140–2° C.;

$^1$H (δ, CDCl$_3$, 300 MHz) 7.4–7.55 (2H, m), 7.6 (I1H, d), 7.75 (1H, s), 8.1 (1H, d), 8.3 (1H, d), 8.5 (2H, s);

LRMS 352, 354, 356 (MH);

El.Anal. Found: C, 50.38; H, 2.20; N, 3.93. Calcd for C$_{15}$H$_8$BrCl$_2$N: C, 50.60; H, 2.33; N, 3.93.

Preparation 39: 4-Bromo-1-chloro-7-(4-methylphenyl) isoquinoline

The title compound was prepared in a similar manner to Preparation 42, from 1-chloro-4,7-dibromoisoquinoline and 4-methylphenylboronic acid as a solid.

M.Pt. 108–110° C.;

$^1$H (δ, CDCl$_3$, 400 MHz) 2.4 (3H, s), 7.3 (2H, d), 7.6 (2H, d), 8.1 (1H, d), 8.2 (1H, d), 8.4 (1H, s), 8.45 (1H, s);

LRMS 332, 334, 336 (MH).

Preparation 40: 4-Bromo-1-chloro-7-(4-methoxyphenyl) isoquinoline

The title compound was prepared in a similar manner to Preparation 42, from 1-chloro-4,7-dibromoisoquinoline and 4-methoxyphenylboronic acid as a white solid.

M.Pt. 94–96° C.;

$^1$H (δ, CDCl$_3$, 400 MHz) 3.85 (3H, s), 7.0 (2H, d), 7.65 (2H, d), 8.05 (1H, 8.15 (1H, d), 8.4 (2H, s);

LRMS 348, 350, 352 (MH);

El.Anal. Found: C, 55.16; H, 3.13; N, 4.02. Calcd for C$_{16}$H, BrClNO: C, 55.12; H, 3.18; N, 4.02.

Preparation 41: 4-Bromo-1-chloro-7-(3-methoxyphenyl) isoquinoline

The title compound was prepared in a similar manner to Preparation 42, from 1-chloro-4,7-dibromoisoquinoline and 3-methoxyphenylboronic acid as a white solid.

$^1$H (δ, CDCl$_3$, 400 MHz) 3.9 (3H, s), 6.9–7.05 (2H, m), 7.3 (1H, d), 7.4 (1H, d), 8.1 (1H, d), 8.2 (1H, d), 8.45 (1H, s), 8.5 (1H, s);

LRMS 347, 349, 351 (MH);

El.Anal. Found: C, 55.49; H, 3.20; N, 3.94. Calcd for C$_{16}$H, BrClNO: C, 55.12; H, 3.18; N, 4.02.

Preparation 42: 1,4-Dichloro-7-(2,6-dimethoxyphenyl) isoquinoline

A solution of 7-bromo-1,4-dichloroisoquinoline (396 mg, 1.42 mmol) and 2,6-dimethoxyphenylboronic acid (261 mg, 1.43 mmol) (J.Chem.Soc., Chem. Commun. 1995, 1085) in anhydrous DME (10 mL) was treated with tetrakis (triphenylphosphine)palladium(0) (38 mg, 19 mol %) and caesium fluoride (485mg, 3.19mmol) and the resultant mixture heated at reflux under N$_2$ for 16 h. The reaction mixture was cooled to room temperature, partitioned between EtOAc (35 mL) and water (10 mL), dried and evaporated to give a solid which was purified by column chromatography upon silica gel using hexanes-EtOAc (99:1 to 96:4) as eluant to give the title compound as an off-white solid (120.6 mg, 0.36 mmol).

$^1$H (δ, CDCl$_3$, 300 MHz) 8.35 (1H, s), 8.3 (1H, s), 8.2 (1H, d), 7.85 (1H, d), 7.35 (1H, t), 6.7 (2H, d), 3.75 (6H, s);

LRMS 334, 336, 338 (MH).

Preparation 43: 1-Chloro-7-(2-phenyl-E-ethenyl) isoquinoline

A solution of 7-bromo-1-chloroisoquinoline (200 mg, 0.80 mmol), styrene (94 mg, 0.90 mmol), tri-o-tolylphosphine (30 mg, 12 mol %), palladium (II) acetate (Pd(OAc)$_2$) (10 mg, 5 mol %) and triethylamine (0.34 mL, 2.5 mmol) in DMF (0.75 mL) were placed in a MOS-2000™ (650 W) microwave and irradiated at full power for 7×40s (reaction monitored by TLC). The mixture was poured into water and extracted with EtOAc. The combined organic layers were dried over MgSO$_4$, evaporated in vacuo and the residue was purified by column chromatography upon silica gel using hexanes-EtOAc (100:0 to 95:5) as eluant to give 1-chloro-(2-phenylethen-1-yl)isoquinoline (135 mg, 0.508 mmol) as a yellow solid.

M.Pt. 118–121° C.;

$^1$H (δ, CDCl$_3$, 300 MHz) 7.3–7.35 (3H, m), 7.44 (2H, dd), 7.55–7.65 (3H, m), 7.8 (1H, d), 8.0 (1H, d), 8.25 (1H, d), 8.3 (1H, s);

LRMS 266, 268 (MH);

El.Anal. Found: C, 76.87; H, 4.61; N, 5.18. Calcd for C$_{17}$H$_{12}$ClN: C, 76.84; H, 4.55; N, 5.27.

Preparation 44: 1-chloro-5-isoquinolinecarboxaldehyde

A solution of n-BuLi (1.76 mL, 2.5 M in hexanes, 4.4 mmol) was added to a stirred solution of 5-bromo-1-chloroisoquinoline (Braye, E.; Eloy, F.; Hoogzand, C.; Lenaers, R. Eur. J. Med. Chem., Chim. Therap. 1974, 9, 197) (1.0 g, 4.12 mmol) in THF-ether (36 mL, 1:1) at −78° C. under N$_2$. After 20 minutes, DMF (0.66 mL, 8.5 mmol) was added and after an additional 30 minutes at −78° C. the reaction was quenched with EtOH (3 mL) and warmed to room temperature. The mixture was diluted with ether (150 mL), washed with saturated NH$_4$Cl (50 mL), brine, dried over MgSO$_4$, and evaporated in vacuo. The residue was purified by column chromatography upon silica gel using hexanes-EtOAc (95:5 to 50:50) as eluant to give 1-chloro-5-isoquinolinecarboxaldehyde (308 mg, 1.61 mmol) as a white solid.

$^1$H (δ, CDCl$_3$, 400 MHz) 7.9 (1H, dd), 8.25 (1H, d), 8.5 (1H, d), 8.7 (1H, d), 9.0 (1H, d), 10.4 (1H, s);

LRMS 192, 194 (MH).

Preparation 45: 1-chloro-7-isoquinolinecarboxaldehyde

The title compound was prepared in a similar manner to Prep.44, from 7-bromo-1-chloroisoquinoline, as a white solid.

$^1$H (δ, DMSO-d$_6$, 300 MHz) 7.95 (1H, d), 8.2 (2H, s), 8.4 (1H, d), 8.85 (1H, s), 10.2 (1H, s).

LRMS 192, 194 (MH).

Preparation 46: 7-Carboxy-1-chloroisoquinoline hydrochloride

A solution of n-BuLi (1.2 mL, 2.5 M in hexanes, 3.0 mmol) was added dropwise to a stirred solution of the 7-bromo-1-chloroisoquinoline (0.64 g, 2.64 mmol) in THF (10 mL) and ether (10 mL) at −78° C. under N$_2$. After 20 min, crushed solid C0$_2$ (excess) was added in one portion and the mixture allowed to warm to room temperature. The solvents were evaporated in vacuo and the residue partioned between aqueous NaOH (20 mL, 0.5 M) and ether (50 mL). The aqueous phase was acidified with conc HCl, extracted with EtOAc (3×50 mL) and the combined organic extracts were dried over MgSO$_4$ and evaporated to leave 7-carboxy-1-chloroisoquinoline hydrochloride (0.277 g, 1.13 mmol) as an off-white solid.

¹H (δ, DMSO-d₆, 300 MHz) 7.95 (1H, d), 8.15 (1H, d), 8.3 (1H, d), 8.4 (1H, d), 8.8 (1H, s), 13.5 (1H, br s);
LRMS 208, 210 (MH).

Preparation 47: 1-Chloro-7-(1-hydroxycyclohex-1-yl)isoquinoline

A solution of 7-bromo-1-chloroisoquinoline (200 mg, 0.82 mmol) in anhydrous THF (4 mL) at −78° C. was treated with s-BuLi (1.3M in cyclohexane, 0.7 mL, 0.91 mmol) to afford a dark green solution which after 4 minutes was quenched with cyclohexanone (100 mL, 0.96 mmol). The cooling bath was removed and the reaction mixture allowed to reach ambient temperature, stirred for 20 minutes and quenched with a drop of water. The THF was removed in vacuo and water (5 mL) added to the residue which was extracted with ethylacetate (3×10 mL). The combined organic extracts were washed with water (5 mL) and brine (5 mL) and then dried over MgSO₄ and condensed onto silica gel (1 g) and purified by column chromatography (silica gel, 15 g) using hexanes-EtOAc (100:15 to 100:20) as eluant to afford the title compound as a white solid (83 mg, 0.32 mmol).

M.Pt. 109.5–111° C.;
¹H (δ, CDCl₃, 300 MHz) 1.3–2.1 (1H, m), 7.55 (1H, d), 7.85 (1H, d), 7.95 (1H, d), 8.25 (1H, d), 8.45 (1H, s);
LRMS 262, 264 (MH).

The following compounds of Preparations 48–51 were made in a similar manner:

Preparation 48: 1-Chloro-7-(1-hydroxycyclopent-1-yl)isoquinoline

The title compound was prepared from 7-bromo-1-chloroisoquinoline quenching the formed anion with cyclopentanone to give a yellow solid.

¹H (δ, CDCl₃, 300 MHz) 1.5–2.2 (9H, m), 7.6 (1H, d), 7.8 (1H, d), 7.9 (1H, d), 8.25 (1H, d), 8.45 (1H, s);
LRMS 248, 250 (MH).

Preparation 49: 1-Chloro-7-(1-hydroxy-1-phenylethyl)isoquinoline

The title compound was prepared from 7-bromo-1-chloroisoquinoline quenching the formed anion with acetophenone to give a cream solid.

M.Pt. 134–5° C.;
¹H (δ, CDCl₃, 400 MHz) 2.0 (3H, m), 2.3 (1H, br s), 7.2–7.35 (3H, m), 7.35–7.45 (2H, m), 7.5 (1H, d), 7.65 (1H, d), 7.7 (1H, d), 8,2 (1H, d), 8.45 (1H, s);
LRMS 284, 286 (MH);
El.Anal. found: C, 71.49; H, 5.06; N, 4.90. Calcd for C₁₇H₁₄ClNO+0.08 EtOAc: C, 71.54; H, 5.07; N, 4.82.

Preparation 50: 1-Chloro-7-(α-hydroxybenzyl)isoquinoline

The title compound was prepared from 7-bromo-1-chloroisoquinoline quenching the formed anion with benzaldehyde to give a white solid.

¹H (δ, CDCl₃, 300 MHz) 2.45 (1H, d), 6.05 (1H, d), 7.2–7.45 (5H, m), 7.55 (1H, d), 7.7 (1H, d), 7.75 (1H, d), 8.15 (1H, d), 8.4 (1H, s);
LRMS 270, 272 (MH);
El.Anal. Found: C, 70.1 1; H, 4.63; N, 4.85. Calcd for C₁₆H₁₂ClN+0.2 EtOAc: C, 70.22; H, 4.77; N, 4.87.

Preparation 51: 1,4-Dichloro-7-(α-hydroxybenzyl)isoquinoline

The title compound was prepared from 7-bromo-1,4-dichloroisoquinoline quenching the formed anion with benzaldehyde to give a white solid.

M.Pt. 121–122° C.;
¹H (δ, CDCl₃, 300 MHz) 2.3–2.6 (1H, br s), 6.1 (1H, s), 7.25–7.5 (5H, m), 7.85 (1H, d), 8.15 (1H, d), 8.3 (1H, s), 8.45 (1H, s);
LRMS 304, 306 (MH);
El.Anal. Found: C, 62.55; H, 3.45; N, 4.61. Calcd for C₁₆H₁₁Cl₂NO+0.2 water: C, 62.44; H, 3.73; N, 4.55.

Preparation 52: 1-Chloro-7-(1-hydroxyethyl)isoquinoline

A slurry of 1-chloro-7-isoquinolinecarboxaldehyde (148 mg, 0.78 mmol) in anhydrous THF (8 mL) at −78° C. was treated with MeLi (1.0M in THF, 0.86 mL, 0.86 mmol) over 30 min. After 15 min, the solution was warmed to 0° C. and stirred for a further 1 h. The reaction mixture was then diluted with EtOAc (30 mL), washed with saturated ammonium chloride solution (20 mL), brine (20 mL), dried over MgSO₄ and condensed to an orange/brown oil. Purification by column chromatography upon silica gel (25 g) using hexanes-EtOAc (10:3) as eluant gave the title compound as a whitish oil (85 mg, 0.41 mmol).

¹H (δ, CDCl₃, 400 MHz) 1.55 (3H, d), 2.15 (1H, s), 5.1 (1H, q), 7.55 (1H, d), 7.7–7.8 (2H, m), 8.2 (1H, d), 8.25 (1H, d);
LRMS 208, 210 (MH).

Preparation 53: 1-Chloro-5-hydroxymethylisoquinoline

A solution of 1-chloro-5-isoquinolinecarboxaldehyde (308 mg, 1.6 mmol) and sodium borohydride (NaBH₄) (68 mg, 1.8 mmol) in MeOH (6 mL) was stirred at room temperature for 2 h. The reaction was quenched with water (2 mL) and concentrated in vacuo. The residue was suspended in CH₂Cl₂, washed with water, with brine and then dried over MgSO₄ and evaporated. The residue was purified by column chromatography upon silica gel using hexanes-EtOAc (80:20 to 50:50) as eluant to give 1-chloro-5-(hydroxymethyl)isoquinoline (240 mg, 1.23 mmol) as a white solid.

¹H (δ, CDCl₃, 400 MHz) 2.0 (1H, br s), 5.15 (2H, s), 7.7 (1H, dd), 7.8 (1H, d), 8.35 (2H, m); 8.35 (2H, m);
LRMS 193 (MH), 387 (M₂H).

Preparation 54: 1-Chloro-7-hydroxymethylisoquinoline

The title compound was prepared in a similar manner to Preparation 53, from 1-chloroisoquinoline-7-carboxaldehyde, to give a white powder.

M.Pt. 118–121° C.;
¹H (δ, DMSO-d₆, 300 MHz) 4.7 (2H, d), 5.5 (1H, t), 7.8 (1H, d), 7.85 (1H, d), 8.0 (1H, d), 8.2 (1H, s), 8.25 (1H, d);
LRMS 194, 196 (MH);
El.Anal. Found: C, 62.24; H, 4.34; N, 7.01. Calcd for C₁₀H₈ClNO: C, 62.01; H, 4.16; N, 7.23.

Preparation 55: 1-Chloro-7-chloromethylisoquinoline hydrochloride

1-Chloro-7-(hydroxymethyl)-isoquinoline (510 mg, 2.63 mmol) was slowly added to thionyl chloride (4 mL) at ambient temperature and the resultant mixture stirred for 1.5 h giving complete solution. The thionyl chloride was removed in vacuo and methylene chloride (20 mL) was added. The resultant white precipitate was removed by filtration and washed with further methylene chloride (20 mL) then dried in vacuo to afford the title compound (400 mg, 1.61 mmol). A second crop (112 mg, 0.45 mmol) was obtained by evaporation of the methylene chloride and trituration with ether/methylene chloride.

M.Pt. 138–140° C.;
¹H (δ, DMSO-d₆, 300 MHz) 5.0 (2H, s), 7.8–7.95 (2H, m), 8.05 (1H, d), 8.25–8.35 (2H, m);
Elemental Analysis—Found: C, 47.98; H, 3.17; N, 5.58. Calcd for C₁₀H₈Cl₃N: C, 48.32; H, 3.24; N, 5.64.

Preparation 56: 1-Chloro-7-[(2-methyl-1H-imidazol-1-yl)methyl]isoquinoline

Sodium hydride (60% dispersion in oil, 48 mg, 1.2 mmol) was added to a solution of 2-methylimidazole (100 mg, 1.2 mmol) in dry DMF (2 mL) and stirred at room temperature until evolution of H₂ had ceased after which the hydrochloride salt of 1-chloro-7-(chloromethyl)-isoquinoline (150 mg, 0.6 mmol) was added. The reaction mixture was stirred for 3 h, poured into water (10 mL) and extracted with EtOAc (3×10 mL). The organic extracts were combined, dried over $MgSO_4$ and condensed to an oil which was taken up in diisopropyl ether and allowed to crystallise. The solid was removed by filtration to afford white crystals of the title compound (70 mg, 0.27 mmol). A further crop of product (70 mg, 0.27 mmol) was obtained by concentration of the mother liquors.

$^1$H ($\delta$, $CDCl_3$, 400 MHz) 2.35 (3H, s), 5.2 (2H, s), 6.85 (1H, s), 7.95 (1H, s), 7.35 (1H, d), 7.55 (1H, d), 7,8 (1H, d), 8.0 (1H, s), 8.15 (1H, d);

LRMS 258, 260 (MH);

El.Anal. Found: C, 65.14; H, 4.66; N, 16.28. Calcd for $C_{14}H_{12}ClN_3$: C, 65.24; H, 4.69; N, 16.31.

The compounds of Preparations 57 and 58 were made in a similar manner:

Preparation 57: 1-Chloro-7-[(2-methyl-1H-benzo[d]imidazol-1-yl)methyl]isoquinoline The title compound was prepared from 2-methylbenzimidazole to give a cream solid.

M.Pt. 245–7° C.;

$^1$H ($\delta$, $CDCl_3$, 400 MHz) 2.6 (3H, s), 6,6 (2H, s), 7.1–7.25 (3H, m), 7.3 (1H, d), 7.5 (1H, d), 7.7–7.8 (2H, m), 8.15 (1H, s), 8.25 (1H, d);

LRMS 308, 310 (MH);

El.Anal. Found: C, 70.16; H, 4.55; N, 13.54. Calcd for $C_{18}H_{14}ClN_3$: C, 70.24; H, 4.59; N, 13.65.

Preparation 58: 1-Chloro-7-(phenoxymethyl)isoquinoline

The title compound was prepared from phenol, and the off-white solid was used without further purification.

M.Pt.<60° C.;

LRMS 270, 272 (MH).

Preparation 59: 5-Carboxy-1-chloroisoquinoline hydrochloride

A solution of 5-carbethoxy-1-chloroisoquinoline (German Patent DE 2816863) (1.75 g, 7.4 mmol) and NaOH (0.8 g, 20 mmol) in $MeOH-H_2O$ (50 mL, 4:1) was stirred at 23° C. for 5 h. The solvents were evaporated in vacuo and the residue partioned between $CH_2Cl_2$ and aqueous NaOH (2 M). The aqueous phase was acidified with conc HCl and extracted with copious EtOAc (×4). The combined organics were washed with brine, dried over $MgSO_4$ and concentrated in vacuo to leave 5-carboxy-1-chloroisoquinoline hydrochloride (1.8 g, 7.4 mmol) as a white solid.

$^1$H ($\delta$, DMSO-$d_6$, 300 MHz) 7.8 (1H, dd), 8.4 (1H, d), 8.5 (1H, d), 8.6 (1H, d), 8.7 (1H, d), 13.6. (1H, br s);

LRMS 208, 210 (MH).

Preparation 60: 5-Carboxymethoxy-1-chloroisoquinoline hydrochloride

The title compound was prepared in a similar manner to Preparation 59, from 5-(ethoxycarbonylmethoxy)-1-chloroisoquinoline, giving a white solid.

M.Pt.>200° C.;

$^1$H ($\delta$, DMSO-$d_6$, 300 MHz) 4.9 (2H, s), 7.2 (1H, d), 7.7 (1H, dd), 7.8 (1H, d), 8.0 (1H, d), 8.3 (1H, d), 12.6 (1H, br s);

LRMS 238 (MH).

Preparation 61: 5-Carboxamido-1-chloroisoquinoline

A solution of 5-carboxy-1-chloroisoquinoline hydrochloride (395 mg, 1.62 mmol) in $SOCl_2$ (5 mL) containing DMF (1 drop) was heated at reflux under $N_2$ for 2 h. The solvents were evaporated in vacuo and the residue azeotroped with PhMe to yield 1-chloro-5-isoquinoyl chloride hydrochloride (1.62 mmol) as an off-white solid. The acid chloride was used immediately without purification or characterisation.

A solution of 1-chloro-5-isoquinoyl chloride hydrochloride (1.62 mmol) in an $NH_3$ saturated $CH_2Cl_2$ (25 mL) was stirred at 23° C. for 18 h. The solvents were evaporated in vacuo, the residue redissolved in $CH_2Cl_2$ and washed with water, and with brine. The organic phase was dried over $MgSO_4$ and concentrated in vacuo to leave the crude product which was purified by trituration with ether to give 5-carboxamido-1-chloroisoquinoline (92 mg, 0.45 mmol) as a white solid.

$^1$H ($\delta$, DMSO-$d_6$, 400 MHz) 7.7 (1H, br s), 7.8 (1 H,dd), 8.0 (1H, d), 8.1 (1H, br s), 8.2 (1H, d), 8.3 (1H, d), 8.4 (1H, d);

LRMS 206, 209 (MH);

Elemental Analysis—Found: C, 57.61; H, 3.33; N, 13.30. Calculated for $C_{10}H_7ClN_2O+0.04CH_2Cl_2$: C, 57.42; H, 3.40; N, 13.34.

The compounds of Preparations 62 and 63 were prepared in a similar manner:

Preparation 62: 5-(Carbamoylmethoxy)-1-chloroisoquinoline

The title compound was prepared from 5-carboxymethoxy-1-chloroisoquinoline hydrochloride, as a white powder.

M.Pt. 163–6° C.;

$^1$H ($\delta$, DMSO-$d_6$, 400 MHz) 4.6 (2H, s), 7.2 (1H, d), 7.45 (1H, br s), 7.65 (1H, br s), 7.7 (1H, dd), 7.8 (1H, d), 8.25–8.2 (2H, m);

LRMS 237, 239 (MH);

El.Anal. Found: C, 51.83; H, 4.13; N, 11.07. Calcd for $C_{11}H_9ClN_2O_2+H_2O$: C, 51.88; H, 4.35; N, 11.00.

Preparation 63: 7-N-Benzylcarbamoyl-1-chloroisoquinoline

The title compound was prepared from 7-carboxy-1-chloroisoquinoline hydrochloride and benzylamine, and gave a tan-coloured solid.

M.Pt. 144–5° C.;

$^1$H ($\delta$, $CDCl_3$, 400 MHz) 4.7 (2H, d), 6.7 (1H, br s), 7.45–7.25 (5H, m), 7.6 (1H, d), 7.85 (1H, d), 8.15 (1H, d), 8.3 (1H, d), 8.65 (1H, s);

LRMS 297 (MH), 593 ($M_2$H).

Preparation 64: 1-Chloro-5-sulphamoylisoquinoline

To an ice-cold solution of fuming sulphuric acid (20% $SO_3$, 2 mL) was added 1-chloroisoquinoline (1.0 g, 6.1 mmol) portionwise with stirring. After stirring at room temperature for 3 hours, the reaction was heated at 80° C. for 18 h, then cooled in an ice bath, poured onto ice (70 g), washed with ether, and concentrated in vacuo. The residues were treated with isopropanol giving a white solid which was filtered and dried to give 1-chloro-5-isoquinolinesulphonic acid (1.16 g, 4.77 mmol).

$^1$H ($\delta$, $D_2O$, 400 MHz) 7.6 (1H, t), 8.10.84 (4H, m);

LRMS 244 (MH).

A suspension of 1-chloro-5-isoquinolinesulphonic acid (1.14 g, 4.68 mmol) in thionyl chloride (13 mL) and DMF (0.3 mL, 3.9 mmol) was heated to reflux for 3 h. Concentration in vacuo and azeotroping with toluene gave 1-chloro-5-chlorosulphonylisoquinoline as an off-white solid which was used immediately.

A solution of 1-chloro-5-chlorosulphonylisoquinoline (613 mg, 2.34 mmol) in methylene chloride saturated with ammonia gas (20 mL) was stirred at RT for 18 h, concentrated in vacuo to a white solid and purified by column chromatography upon silica gel (preabsorbed) using EtOAc-hexanes (1:1) as eluant to give 1-chloro-5-sulphamoylisoquinoline as a white solid (206 mg, 0.85 mmol).

M.Pt. 216–8° C.;

$^1$H (δ, DMSO-d$_6$, 400 MHz) 7.8 (1H, s), 7.9 (1H, t), 8.4 (1H, d), 8.45 (1H, s), 8.5 (1H, d);

LRMS 243, 245 (MH);

Found: C, 44.46; H, 3.01; N, 11.49. Calcd for C$_9$H$_7$ClN$_2$O$_2$S: C, 44.54; H, 2.91; N, 11.54.

Preparation 65: 1-Chloro-7-sulphamoylisoquinoline

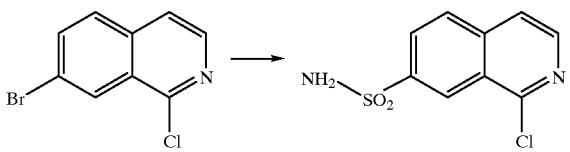

n-Butyllithium (0.35 mL, 2.5 M in hexanes, 0.875 mmol) was added dropwise to a stirred solution of 7-bromo-1-chloroisoquinoline (200 mg, 0.825 mmol) in tetrahydrofuran-ether (THF-Et$_2$O) (2.0 mL, 1: 1) under N$_2$ at -78 3C. After 5 min, the mixture was added to a solution of sulphuryl chloride (SO$_2$Cl$_2$) (0.14 mL, 1.74 mmol) in hexane (2.0 mL) at −25° C. under N$_2$ and the mixture was warmed to 23° C. and stirred for 3 h. Concentrated aqueous ammonia (3.0 mL, 0.880) was added and then all solvents were evaporated in vacuo. The residue was suspended in EtOAc, washed with aqueous HCl (2 M), brine, and then evaporated in vacuo. The residue was purified by column chromatography upon silica gel using hexanes-EtOAc (50:50 to 30:70) as eluant to give the title compound (37 mg, 0.152 mmol) as a white solid.

m.p. 220–222° C.

$^1$H (CD$_3$OD, 400 MHz) δ7.9 (1H, d), 8.2 (1H, d), 8.3 (1H, d), 8.4 (1H, d), 8.9 (1H, s) ppm.

LRMS 243, 245 (MH$^+$).

Preparation 66: 1-Chloro-7-phenylsulphamoylisoquinoline

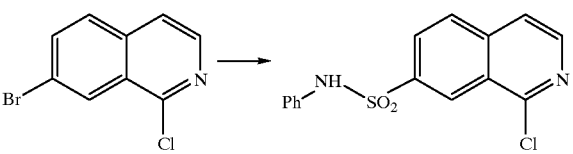

n-Butyllithium (0.88 mL, 2.5 M in hexanes, 2.2 mmol) was added dropwise to a stirred solution of 7-bromo-1-chloroisoquinoline (500 mg, 2.06 mmol) in THF-ether (10 mL, 1:1) under N$_2$ at −78° C. After 5 min, the mixture was added to a solution of SO$_2$Cl$_2$ (0.35 mL, 4.36 mmol) in hexane (10 mL) at −25° C. under N$_2$, the mixture was warmed to 23° C. and stirred for 4.5 h. The solvents were evaporated in vacuo, azeotroping with PhMe, the residue was suspended in CH$_2$Cl$_2$ (12 mL) and then aniline (0.25 mL, 2.74 mmol) and NEt$_3$ (1.15 mL, 8.25 mmol) were added. The mixture was stirred at room temperature overnight, washed with aqueous HCl (2 M), brine, and then evaporated in vacuo. The residue was purified by column chromatography upon silica gel using hexanes-EtOAc (80:20 to 50:50) as eluant to give the title compound (116 mg, 0.36 mmol) as an off-white solid.

$^1$H (CD$_3$OD, 400 MHz) δ7.0–7.15 (3H, m), 7.2–7.25 (2H, m), 7.8 (1H, d), 8.1 (2H, 2×d), 8.4 (1H, d), 8.7 (1H, s) ppm.

LRMS 319, 321 (MH$^+$).

Preparation 67: 7-Chlorosulphonyl-1,4-dichloroisoquinoline

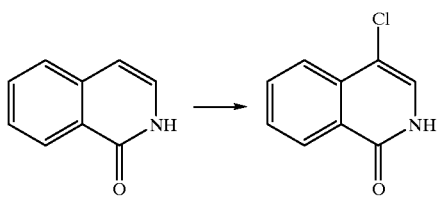

A solution of N-chlorosuccinimide (9.66 g, 72 mmol) in acetonitrile (MeCN) (80 mL) was added dropwise to a stirred solution of 1-(2H)-isoquinolone (10 g, 69 mmol) in MeCN (250 mL) which was being heated under reflux. The mixture was heated under reflux for an additional 1.5 h and then cooled to room temperature. The resulting precipitate was collected by filtration, with MeCN rinsing, and then dried in vacuo to give 4-chloro-1(2H)-isoquinolone (11.3 g, 62.9 mmol) as a pale pink solid.

$^1$H (DMSO-d$_6$, 300 MHz) δ7.5 (1H, s), 7.6 (1H, dd), 7.8–7.9 (2H, m), 8.25 (1H, d), 11.5 (1H, br s), ppm.

LRMS 180, 182 (MH$^+$), 359, 361, 363 (M$_2$H$^+$).

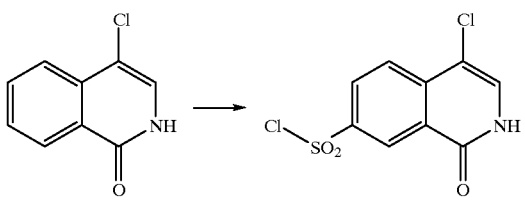

4-Chloro-1-(2H)-isoquinolone (20.62 g, 115 mmol) was added portionwise to stirred chlorosulphonic acid (61 mL, 918 mmol) at 0° C. The mixture was heated at 100° C. for 3.5 d and then cooled to room temperature. The reaction mixture was added in small portions onto ice-water [CAUTION] and the resulting precipitate was collected by filtration. The solid was washed with water, triturated with MeCN and then dried in vacuo to give 4-chloro-7-chlorosulphonyl-1-(2H)-isoquinolone (18.75 g, 67.4 mmol) as a cream solid.

$^1$H (DMSO-d$_6$, 400 MHz) δ7.45 (1H, s), 7.8 (1H, d), 8.0 (1H, d), 8.5 (1H, s), 11.5 (1H, br s) ppm.

Found: C, 39.37; H, 2.09; N, 4.94. Calc for C$_9$H$_5$Cl$_2$NO$_3$S: C, 38.87; H, 1.81; N, 5.04.

(iii)

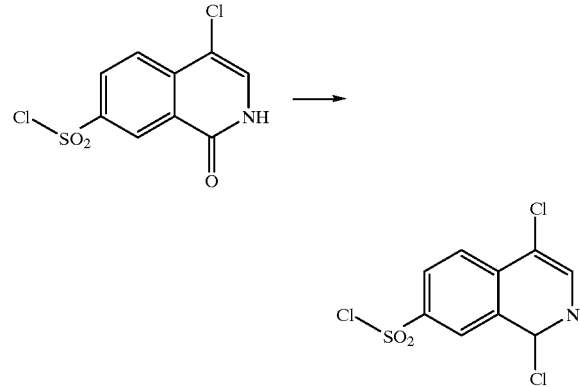

Phosphorus oxychloride (POCl$_3$) (9.65 mL, 103.5 mmol) was added to a stirred suspension of 4-chloro-7-chlorosulphonyl-1-(2H)-isoquinolone (22.1 g, 79.6 mmol)

in MeCN (500 mL) at room temperature and the mixture was then heated at reflux for 15 h. On cooling, the MeCN solution was decanted from the insoluble sludge and evaporated in vacuo. The residue was extracted with hot EtOAc and evaporated to leave a solid which was stirred with Et$_2$O (1.2 L) at room temperature overnight. The ethereal solution was decanted from the insoluble material and evaporated in vacuo to give 7-chlorosulphonyl-1,4-dichloroisoquinoline (20 g, 67 mmol) as a pale yellow solid.

$^1$H (DMSO-d$_6$, 400 MHz) δ8.2 (2H, s), 8.5 (1H, s), 8.55 (1H, s) ppm.

Anal. Found: C, 37.19; H, 1.34; N, 4.77. Calc for C$_9$H$_4$Cl$_3$NO$_2$S: C, 36.45; H, 1.36; N, 4.72.

Preparation 68: 1,4-Dichloro-7-sulphamoylisoquinoline

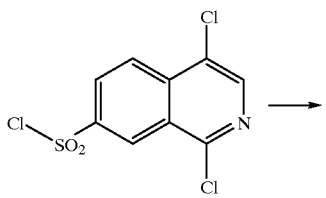

7-chlorosulphonyl-1,4-dichloroisoquinoline (110 mg, 0.37 mmol) was dissolved in a solution of saturated methanolic ammonia (NH$_3$) (10 mL) and the solution stirred at room temperature for 1.5 hours. The solvents were evaporated in vacuo and the residue was azeotroped with CH$_2$Cl$_2$ and then partitioned between EtOAc and water. The organic phase was washed with brine, dried (MgSO$_4$) and evaporated in vacuo to give 1,4-dichloro-7-sulphamoylisoquinoline (98 mg, 0.35 mmol) as a white solid.

$^1$H (DMSO-d$_6$, 400 MHz) δ7.8 (2H, s), 8.35 (1H, d), 8.45 (1H, d), 8.6 (1H, s), 8.75 (1H, s) ppm.

LRMS 276, 278 (MH$^+$).

Preparation 69: 7-Cyclopentylsulphamoyl-1,4-dichloroisoquinoline

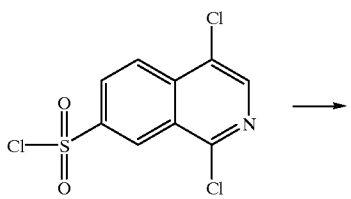

A mixture of cyclopentylamine (0.10 mL, 1.0 mmol), NEt$_3$ (0.17 mL, 1.2 mmol) and 7-chlorosulphonyl-1,4-dichloroisoquinoline (250 mg, 0.84 mmol) in CH$_2$Cl$_2$ (15 mL) was stirred at 23° C. for 18 h. The mixture was diluted with CH$_2$Cl$_2$ (30 mL), washed with dilute HCl (2 M), saturated aqueous sodium bicarbonate (NaHCO$_3$), brine, dried (MgSO$_4$) and evaporated in vacuo to give the title compound (250 mg, 0.72 mmol) as a white solid.

mp 165–167° C. (dec).

$^1$H (CDCl$_3$, 300 MHz) δ1.3–1.95 (8H, m), 3.75 (1H, sextet), 4.6 (1H, d), 8.2 (1H, d), 8.4 (1H, d), 8.5 (1H, s), 8.9 (1H, s) ppm.

LRMS 346 (MH$^+$).

Found: C, 48.76; H, 4.04; N, 7.98. Calc for C$_{14}$H$_{14}$Cl$_2$N$_2$O$_2$S: C, 48.71; H, 4.09; N, 8.11.

Preparation 70: 1,4-Dichloro-7-pyrrolidinosulphonylisoquinoline

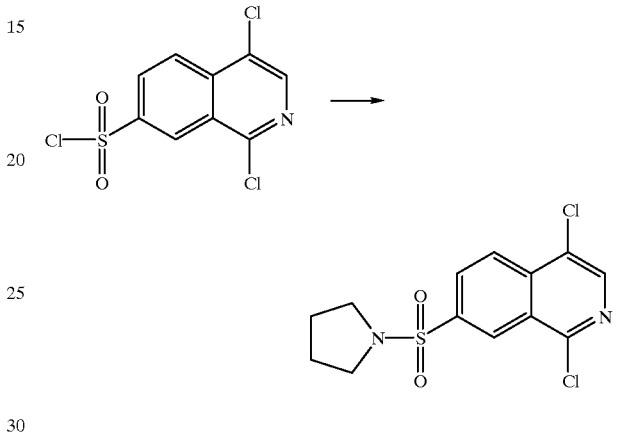

The title compound was prepared by same the general method as Preparation 69.

mp 197–199° C.

$^1$H (CDCl$_3$, 300 MHz) δ1.8 (4H, m), 3.4 (4H, m), 8.2 (1H, d), 8.4 (1H, d), 8.5 (1H, s), 8.8 (1H, s) ppm.

LRMS 331, 333 (MH$^+$).

Found: C, 47.23; H, 3.60; N, 8.32. Calc for C$_{13}$H$_{12}$Cl$_2$N$_2$O$_2$S: C, 47.14; H, 3.65; N, 8.46.

Preparation 71: 1,4-Dichloro-7-morpholinosulphonylisoquinoline

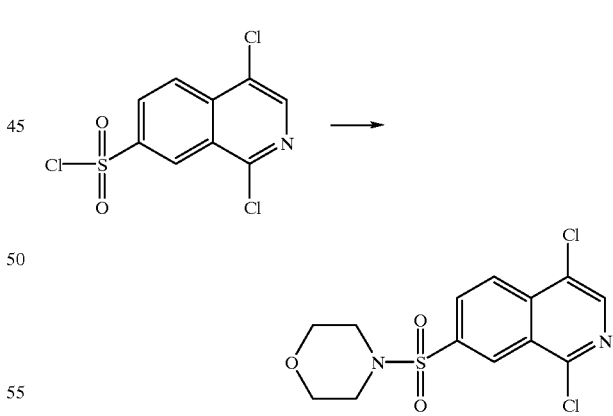

The title compound was prepared by same the general method as Preparation 69.

mp 170–171° C.

$^1$H (CDCl$_3$, 400 MHz) δ3.1 (4H, s), 3.8 (4H, s), 8.1 (1H, d), 8.4 (1H, s), 8.5 (1H, d), 8.8 (1H, s) ppm.

LRMS 347, 349 (MH$^+$).

Found: C, 44.90; H, 3.43; N, 7.83. Calc for C$_{13}$H$_{12}$Cl$_2$N$_2$O$_3$S: C, 44.97; H, 3.48; N, 8.07.

Preparation 72: 1,4-Dichloro-7-(N-methylpiperazino)sulphonylisoquinoline hydrochloride

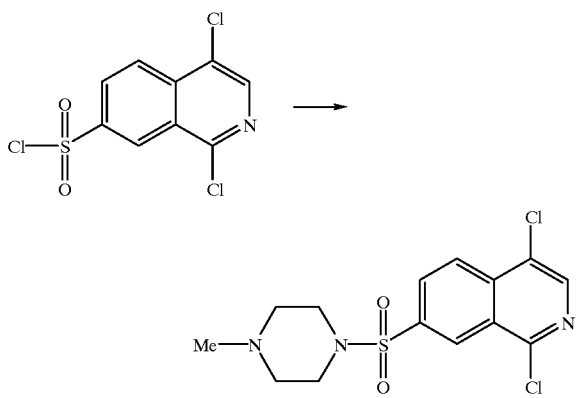

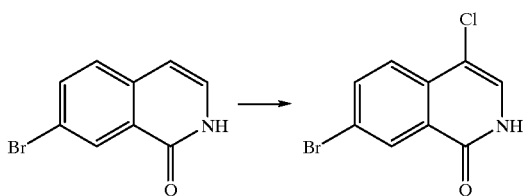

The title salt was prepared by same the general method, see Preparation 69.

mp 260.5–261.5° C.

$^1$H (CDCl$_3$, 400 MHz) δ2.8 (3H, s), 3.1 (2H, br s), 3.5 (4H, br m), 4.0 (2H, br d), 8.1 (1H, d), 8.4 (1H, d), 8.5 (1H, s), 8.8 (1H, s), 13.5 (1H, br s) ppm.

LRMS 360, 362 (MH$^+$).

Found: C, 41.93; H, 4.15; N, 10.08. Calc for C$_{14}$H$_{15}$Cl$_2$N$_3$O$_2$S.HCl.0.4H$_2$O: C, 41,63; H, 4.19; N, 10.40.

Preparation 73: 7-Bromo-4-chloro-1(2H)-isoquinolone

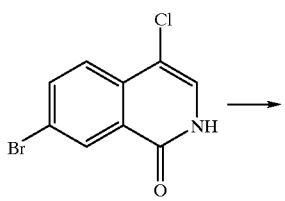

A solution of N-chlorosuccinimide (4.13 g, 31 mmol) in MeCN (50 mL) was added dropwise to a stirred solution of 7-bromo-1-(2H)-isoquinolone (6.6 g, 29.5 mmol) in MeCN (150 mL) which was heating under reflux. The mixture was heated under reflux for an additional 3 h and then cooled to room temperature. The resulting precipitate was collected by filtration, with MeCN rinsing, and then dried in vacuo to give 7-bromo-4-chloro-1(2H)-isoquinolone (6.72 g, 26.0 mmol) as a white solid.

mp 241–243° C.

$^1$H (DMSO-d$_6$, 300 MHz) δ7.5 (1H, s), 7.73 (1H, d), 7.8 (1H, dd), 8.3 (1H, s) ppm.

LRMS 259 (MH$^+$), 517 (M$_2$H$^+$).

Anal. Found: C, 41.69; H, 1.90; N, 5.37. Calc for C$_9$H$_5$BrClNO: C, 41.80; H, 1.95; N, 5.42.

Preparation 74: 4-Chloro-7-(phenylsulfanyl)-1(2H)-isoquinolone

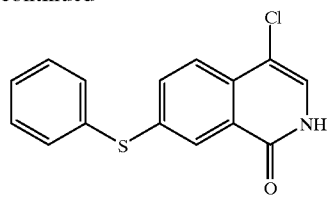

NaH (45 mg, 80% dispersion in mineral oil, 1.5 mmol) was added to a stirred solution of 7-bromo-4-chloro-1-(2H)-isoquinolone (390 mg, 1.5 mmol) in THF (15 mL) under N$_2$ at 0° C. and the mixture was stirred for 5–10 min which gave a clear orange solution. This solution was cooled to −78° C., a solution of n-BuLi (0.60 mL, 2.5 M in hexanes, 1.5 mmol) was added dropwise and the solution was stirred for an additional 15 min. A solution of S-phenyl benzenethiosulphate (PhSO$_2$SPh) (378 mg, 1.5 mmol) in THF (5 mL) was added, the solution was stirred at −70° C. for 10 min and then allowed to warm slowly to room temperature. Water (30 mL) was added and the mixture was extracted with EtOAc (3×20 mL). The combined organic extracts were washed with water, brine, dried (Na$_2$SO$_4$) and evaporated in vacuo. The residue was purified by column chromatography upon silica gel using CH$_2$Cl$_2$—MeOH-0.880NH$_3$ (95:5:0.5) as eluant, followed by recrystallisation from EtOAc, to give 4-chloro-7-(phenylsulfanyl)-1(2H)-isoquinolone (186 mg, 0.64 mmol) as a white solid. A second crop of material (40 mg, 0.14 mmol) was recovered from the mother liquors.

$^1$H (DMSO-d$_6$, 300 MHz) δ7.35–7.5 (6H, m), 7.7 (1H, d), 7.8 (1H, d), 8.0 (1H, s) ppm.

LRMS 288, 290 (MH$^+$), 575 (M$_2$H$^+$).

Anal. Found: C, 61.85; H, 3.48; N, 4.81. Calc for C$_{15}$H$_{10}$ClNOS.0.25H$_2$O: C, 61.64; H, 3.62; N, 4.79.

Preparation 75: 1,4-Dichloro-7-(phenylsulfanyl)isoquinoline

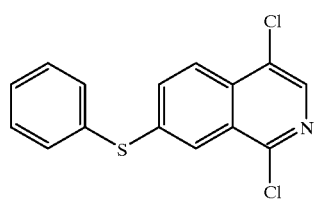

POCl$_3$ (46 μL, 0.50 mmol) was added to a stirred suspension of 4-chloro-7-(phenylsulfanyl)-1-(2H)-isoquinolone (120 mg, 0.42 mmol) in MeCN (2 mL) at 23° C., and the mixture was heated at reflux for 1.5 h which gave a clear solution. This cooled solution was poured into water (20 mL) and the mixture was extracted with EtOAc (×3). The combined organic extracts were washed with brine, dried (Na$_2$SO$_4$) and evaporated in vacuo. The residue was purified by column chromatography upon silica gel using hexanes-EtOAc (90:10) as eluant to give 1,4-dichloro-7-(phenylsulfanyl)isoquinoline (92 mg, 0.30 mmol) as an oil which solidified on standing.

¹H (CDCl₃, 300 MHz) δ7.45 (3H, m), 7.55 (2H, m), 7.65 (1H, dd), 8.1 (1H, d), 8.1 (1H, s), 8.3 (1H, s) ppm.

LRMS 306, 308 (MH⁺).

Anal. Found: C, 57.90; H, 2.99; N, 4.67. Calc for C₁₅H₉Cl₂NS.0.25H₂O: C, 57.98; H, 3.08; N, 4.51.

Preparation 76: 1,4-Dichloro-7-(phenylsulfonyl) isoquinoline

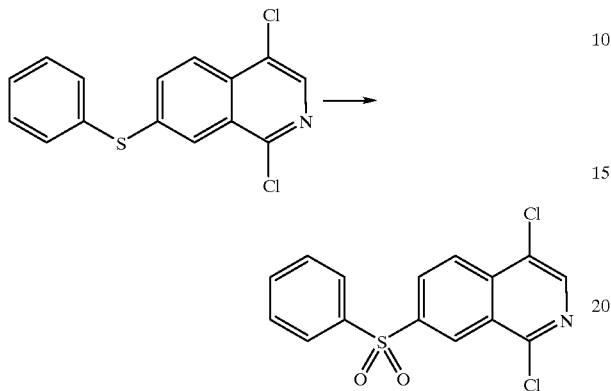

mCPBA (270 mg, 50–55% by wt, 0.78 mmol) was added to a stirred solution of 1,4-dichloro-7-(phenylsulfanyl) isoquinoline (120 mg, 0.39 mmol) in CH₂Cl₂ (20 mL) at 23° C. and the mixture was stirred for 4 h. The solution was washed with aqueous NaHCO₃ (×3, 10%) brine, dried (Na₂SO₄) and evaporated in vacuo. The residue was purified by column chromatography upon silica gel using hexanes-EtOAc (70:30) as eluant, followed by crystallisation with CH₂Cl₂-i-Pr₂O, to give 1,4-dichloro-7-(phenylsulfonyl) isoquinoline (87 mg, 0.25 mmol) as a white solid.

¹H (CDCl₃, 300 MHz) δ7.5–7.7 (3H, m), 8.05 (2H, d), 8.15 (1H, d), 8.35 (1H, s), 9.05 (1H, s) ppm.

LRMS 338, 340 (MH⁺).

Anal. Found: C, 52.55; H. 2.59; N. 4.10. Calc for C₁₅H₉Cl₂NO₂S.0.25H₂O: C, 52.56; H, 2.79; N, 4.09.

What is claimed is:

1. A compound of formula (I):

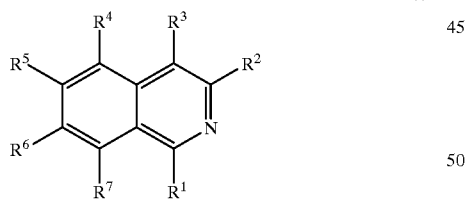

or a pharmaceutically acceptable salt thereof, wherein
one of $R^1$ and $R^2$ is H and the other is N=C(NH₂)₂ or NHC(=NH)NH₂, $R^3$ is H, halogen, $C_{1-6}$ alkyl optionally substituted by one or more halogen, or $C_{1-6}$ alkoxy optionally substituted by one or more halogen, $R^4$, $R^5$, $R^6$ and $R^7$ are each independently H, OH, halogen, $C_{1-6}$ alkyl optionally substituted by one or more substituents independently selected from halogen or OH, $C_{1-6}$ alkoxy optionally substituted by one or more halogen, CN, CO($C_{1-6}$ alkyl optionally substituted by one or more halogen), ($C_m$-alkylene)CO₂R⁸, O($C_n$-alkylene)CO₂R⁸, O($C_n$-alkylene)CN, ($C_n$-alkylene)CN, ($C_m$-alkylene)CONR⁹R¹⁰, ($C_m$-alkylene) NR⁹COR¹⁰, O($C_n$-alkylene)CONR⁹R¹⁰, ($C_m$-alkylene) NR⁹SO₂R¹¹, ($C_m$-alkylene)S(O)ₚR¹¹, ($C_m$-alkylene) SO₂NR⁹R¹⁰, CH=CHCOR⁸, CH=CHCONR⁹R¹⁰, CH=CHSO₂R⁸, CH=CHSO₂NR⁹R¹⁰, CH=CHSO₂aryl, or a group of formula X-aryl or X-het, or, where two of $R^4$, $R^5$, $R^6$ and $R^7$ are attached to adjacent carbon atoms, they can be taken together to form an —O($C_n$-alkylene)O-moiety, $R^8$ is H, $C_{1-6}$ alkyl optionally substituted by one or more halogen, or aryl($C_{1-6}$ alkylene), $R^9$ and $R^{10}$ are each independently H, $C_{1-6}$ alkyl optionally substituted by one or more halogen, aryl($C_{1-6}$ alkylene), aryl, heteroaryl or heteroaryl($C_{1-6}$ alkylene), or $R^9$ and $R^{10}$ may be linked together by an alkylene moiety to form, with the atoms to which they are attached, a 4- to 7-membered ring optionally incorporating an additional hetero-group selected from an O or S atom or a $NR^{12}$ group, $R^{11}$ is aryl, heteroaryl, or $C_{1-6}$ alkyl optionally substituted by one or more halogen, $R^{12}$ is H, $C_{1-6}$ alkyl optionally substituted by one or more halogen, or CO($C_{1-6}$ alkyl optionally substituted by one or more halogen), X is a direct link, $C_n$-alkylene, O, ($C_n$-alkylene)O, O($C_n$-alkylene), CH(OH), C($C_{1-6}$ alkyl)OH, CO, S(O)ₚ($C_m$-alkylene), ($C_m$-alkylene)S(O)ₚ, CH=CH, or C≡C, "aryl" is phenyl or naphthyl optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, O($C_n$-alkylene)CN, ($C_n$-alkylene)CN, CO($C_{1-6}$ alkyl optionally substituted by one or more halogen), ($C_m$-alkylene)CO₂R¹³, O($C_n$-alkylene) CO₂R¹³, ($C_m$-alkylene)CONR¹⁴R¹⁵, ($C_m$-alkylene) NR¹⁴COR¹⁵, O($C_n$-alkylene)CONR¹⁴R¹⁵, ($C_m$-alkylene)S(O)ₚR¹³, ($C_m$-alkylene)SO₂NR¹⁴R¹⁵, ($C_m$-alkylene)NR¹⁴SO₂R¹⁶, CH=CHSO₂R¹³, CH=CHSO₂NR¹⁴R¹⁵, CH=CHSO₂aryl¹, CH=CHCOR¹³, and CH=CHCONR¹⁴R¹⁵, "heteroaryl" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, O($C_n$-alkylene)CN, ($C_n$-alkylene) CN, CO($C_{1-6}$ alkyl optionally substituted by one or more halogen), ($C_m$-alkylene)CO₂R¹³, O($C_n$-alkylene) CO₂R¹³, ($C_m$-alkylene)CONR¹⁴R¹⁵, ($C_m$-alkylene) NR¹⁴COR¹⁵, O($C_n$-alkylene)CONR¹⁴R¹⁵, ($C_m$-alkylene)NR SO₂R¹⁶, ($C_m$-alkylene)S(O)ₚR¹³, ($C_m$-alkylene)SO₂NR¹⁴R¹⁵, CH=CHCOR¹³, CH=CHCONR¹⁴R¹⁵, CH=CHSO₂R¹³, CH=CHSO₂NR¹⁴R¹⁵, or CH=CHSO₂aryl¹, "het" is an optionally benzo-fused 5- or 6-membered heterocyclic group linked to the "X" moiety by any available atom in the heterocyclic or benzo-ring (if present), which heterocyclic group is selected from dioxolyl, dioxolanyl, furyl, thienyl, pyrrolyl, oxazolyl, oxazinyl, thiazinyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, or a fully unsaturated, partially or fully saturated analogue thereof, such "het" group being optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, $O(C_n\text{-alkylene})CN$, $(C_n\text{-alkylene})CN$, $CO(C_{1-6}$ alkyl optionally substituted by one or more halogen), $(C_m\text{-alkylene})CO_2R^{13}$, $O(C_n\text{-alkylene})CO_2R^{13}$, $(C_m\text{-alkylene})CONR^{14}R^{15}$, $(C_m\text{-alkylene})NR^{14}COR^{15}$, $O(C_n\text{-alkylene})CONR^{14}R^{15}$, $(C_m\text{-alkylene})NR^{14}SO_2R^{16}$, $(C_m\text{-alkylene})S(O)_pR^{13}$, $(C_m\text{-alkylene})SO_2NR^{14}R^{15}$, $CH=CHCOR^{13}$, $CH=CHCONR^{14}R^{15}$, $CH=CHSO_2R^{13}$, $CH=CHSO_2NR^{14}R^{15}$, and $CH=CHSO_2aryl^1$, "aryl$^1$" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n\text{-alkylene})CN$, $(C_n\text{-alkylene})CN$, $CO(C_{1-6}$ alkyl optionally substituted by one or more halogen), $(C_m\text{-alkylene})CO_2R^{13}$, $O(C_n\text{-alkylene})CO_2R^{13}$, $(C_m\text{-alkylene})CONR^{14}R^{15}$, $(C_m\text{-alkylene})NR^{14}COR^{15}$, $O(C_n\text{-alkylene})CONR^{14}R^{15}$, $(C_m\text{-alkylene})S(O)_pR^{13}$, $(C_m\text{-alkylene})SO_2NR^{14}R^{15}$, $(C_m\text{-alkylene})NR^{14}SO_2R^{16}$, $CH=CHSO_2R^{13}$, $CH=CHSO_2NR^{14}R^{15}$, $CH=CHCOR^{13}$, and $CH=CHCONR^{14}R^{15}$, $R^{13}$ is H, $C_{1-6}$ alkyl optionally substituted by one or more halogen, or $aryl^2(C_{1-6}$ alkylene), $R^{14}$ and $R^{15}$ are each independently H, $C_{1-6}$ alkyl optionally substituted by one or more halogen, $aryl^2(C_{1-6}$ alkylene), $aryl^2$, heteroaryl$^1$ or heteroaryl$^1(C_{1-6}$ alkylene), or $R^9$ and $R^{10}$ may be linked together by an alkylene moiety to form, with the atoms to which they are attached, a 4- to 7-membered ring optionally incorporating an additional hetero-group selected from an O or S atom or a $NR^{12}$ group, $R^{16}$ is $aryl^2$, heteroaryl$^1$, or $C_{1-6}$ alkyl optionally substituted by one or more halogen, "aryl$^2$" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n\text{-alkylene})CN$, $(C_n\text{-alkylene})CN$, or $CO(C_{1-6}$ alkyl optionally substituted by one or more halogen), "heteroaryl$^1$" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl$^1$" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n\text{-alkylene})CN$, $(C_n\text{-alkylene})CN$, or $CO(C_{1-6}$ alkyl optionally substituted by one or more halogen), wherein the "C-alkylene" linking groups in the definitions above are linear or branched, and are optionally substituted by one or more ($C_{1-6}$ alkyl optionally substituted by one or more halogen) groups, m is an integer from 0 to 3, n is an integer from 1 to 3, and is an integer from 0 to 2.

2. A compound or salt according to claim 1 wherein $R^1$ is $N=C(NH_2)_2$ or $NHC(=NH)NH_2$ and $R^2$ is H.

3. A compound or salt according to claim 1 wherein $R^3$ is H, halogen or $C_{1-6}$ alkyl optionally substituted by one or more halogen.

4. A compound or salt according to claim 1 wherein $R^4$ is H, OH, halogen, $C_{1-6}$ alkyl optionally substituted by one or more substituents independently selected from halogen or OH, $C_{1-6}$ alkoxy optionally substituted by one or more halogen, CN, $(C_m\text{-alkylene})CONR^9R^{10}$, $O(C_n\text{-alkylene})CONR^9R^{10}$, $(C_m\text{-alkylene})SO_2NR^9R^{10}$, or a group of formula X-aryl or X-het.

5. A compound or salt according to claim 1 wherein $R^5$ is H, halogen, or $C_{1-6}$ alkyl optionally substituted by one or more substituents independently selected from halogen or OH.

6. A compound or salt according to claim 1 wherein $R^6$ is H, halogen, $C_6$ alkyl optionally substituted by one or more substituents independently selected from halogen or OH, $C_{1-6}$ alkoxy optionally substituted by one or more halogen, CN, $O(C_n\text{-alkylene})CN$, $(C_n\text{-alkylene})CN$, $(C_m\text{-alkylene})CONR^9R^{10}$, $(C_m\text{-alkylene})CO_2R^8$, $(C_m\text{-alkylene})SO_2NR^9R^{10}$, $(C_m\text{-alkylene})S(O)_pR^{11}$ or a group of formula X-aryl or X-het.

7. A compound or salt according to claim 1 wherein $R^7$ is H.

8. A compound or salt according to claim 1 wherein $R^3$ is H, Cl, Br or methyl optionally substituted by one or more halogen.

9. A compound or salt according to claim 1 wherein $R^4$ is H, Br, OH, CN, $C_{1-6}$ alkoxy, $C_{1-6}$ alkyl optionally substituted by one or more OH, $SO_2NR^9R^{10}$, $CONR^9R^{10}$, $OCH_2CONR^9R^{10}$, $OCH_2aryl$, het or aryl.

10. A compound or salt according to claim 1 wherein $R^5$ is H, Br or methyl optionally substituted by one or more halogen.

11. A compound or salt according to claim 1 wherein $R^6$ is H, Cl, Br, $C_{1-6}$ alkyl optionally substituted by one or more OH, $C_{1-6}$ alkoxy, CN, $(C_m\text{-alkylene})CONR^9R^{10}$, $(C_m\text{-alkylene})CO_2R^8$, $(C_m\text{-alkylene})S(O)_pR^{11}$, $(C_m\text{-alkylene})SO_2NR^9R^{10}$ or a group of formula X-aryl or X-het, where X is a direct link, $CH=CH$, $CH(OH)$, CO, $OCH_2$, $CH_2O$ or $CH_2$.

12. A compound or salt according to claim 1 wherein $R^3$ is H, Cl, Br or methyl.

13. A compound or salt according to claim 1 wherein $R^4$ is H, Br, OH, CN, $C_{1-6}$ alkoxy, $C_{1-6}$ alkyl optionally substituted by one or more OH, $SO_2NR^9R^{10}$, $CONH(aryl(C_{1-6}$ alkyl)), $CONH_2$, $OCH_2CONR^9R^{10}$, $OCH_2aryl$, phenyl or naphthyl.

14. A compound or salt according to claim 1 wherein $R^5$ is H, Br or methyl.

15. A compound or salt according to claim 1 wherein $R^6$ is H, Br, methyl optionally substituted by OH, ethyl optionally substituted by OH, cyclopentyl optionally substituted by OH, cyclohexyl optionally substituted by OH, $C_{1-6}$ alkoxy, CN, O($C_n$-alkylene)CN, ($C_n$-alkylene)CN, $SO_2R^{11}$, $SR^{11}$, $CONR^9R^{10}$, $CO_2R^8$, $SO_2NR^9R^{10}$, a group of formula X-(optionally substituted phenyl) or X-het$^1$, where X is a direct link, CH=CH, CH(OH), CO, OCH$_2$, CH$_2$O or CH$_2$, and where the phenyl moiety linked via X is optionally substituted by one or more halogen, $C_{1-6}$ alkyl optionally substituted by one or more substituents independently selected from halogen and OH, $C_{1-6}$ alkoxy optionally substituted by one or more halogen, or $CO_2R^{13}$, where "het$^1$" is an optionally benzo-fused dioxolyl, furyl, thienyl, imidazolyl, or a partially or fully saturated analogue thereof, and such "het$^1$" group linked via X being optionally substituted by one or more $C_{1-6}$ alkyl optionally substituted by one or more substituents independently selected from halogen and OH.

16. A compound or salt according to claim 1 wherein $R^4$ is H, Br, CN, OCH$_3$, SO$_2$NH$_2$, CH$_2$OH, CONH$_2$, OCH$_2$CONH$_2$, CONHBn, OBn, OH or Ph.

17. A compound or salt according to claim 1 wherein $R^6$ is H, Br, CO$_2$H, (E)CH=CHPh, Ph, OCH$_3$, 1,3-benzo[d]dioxol-5-yl, CN, CH$_2$OH, CONHBn, 4-methoxyphenyl, 1-hydroxycyclohexyl, 1-hydroxycyclopentyl, COPh, CH(OH)CH$_3$, CH(OH)Ph, CCH$_3$(OH)Ph, OCH$_2$Ph, SO$_2$Ph, SPh, CH$_2$OPh, SO$_2$NH$_2$, SO$_2$NHPh, SO$_2$NH(cyclopentyl), SO$_2$(pyrrolidino), SO$_2$(morpholino), SO$_2$(N-methylpiperazino), (2-methylimidazol-1-yl)methyl, (2-methylbenzimidazol-1-yl)methyl, benzofuran-2-yl, thien-3-yl, thien-2-yl, 4-methylphenyl, 2-methoxyphenyl, 3-methoxyphenyl, 3,5-dimethoxyphenyl, 2,6-dimethoxyphenyl, 3-carboxyphenyl, 3-cyanophenyl or 3-chlorophenyl.

18. A compound or salt according to claim 1 wherein $R^6$ is CH(OH)Ph, 2-methoxyphenyl, 3-methoxyphenyl, 4-methoxyphenyl, 2,6-dimethoxyphenyl, SO$_2$NH$_2$, SO$_2$NHPh, SO$_2$NH(cyclopentyl), SO$_2$(pyrrolidino), SO$_2$(morpholino), SO$_2$Ph, SPh, SO$_2$(N-methylpiperazino) or 3-carboxyphenyl.

19. A compound or salt according to claim 1 wherein $R^1$ is N=C(NH$_2$)$_2$ or NH(C(=NH)NH$_2$, each of $R^2$, $R^4$, $R^5$ and $R^7$ are H, $R^3$ is Br or Cl, and $R^6$ is 2-methoxyphenyl, 4-methoxyphenyl, CH(OH)Ph, SO$_2$Ph, SPh, 3-carboxyphenyl or 3-methoxyphenyl.

20. A compound or salt according to claim 1 wherein two of $R^4$, $R^5$, $R^6$ and $R^7$ are attached to adjacent carbon atoms, and are taken together to form a OCH$_2$O moiety.

21. A compound or salt according to claim 1 selected from:
(4-chloro-7-(2-methoxyphenyl)isoquinolin-1-yl)guanidine;
(4-chloro-7-(3-methoxyphenyl)isoquinolin-1-yl)guanidine;
(4-chloro-7-(4-methoxyphenyl)isoquinolin-1-yl)guanidine;
(4-chloro-7-(2,6-dimethoxyphenyl)isoquinolin-1-yl) guanidine;
(4-bromo-7-(3-methoxyphenyl)isoquinolin-1-yl)guanidine;
(4-bromo-7-(4-methoxyphenyl)isoquinolin-1-yl)guanidine;
(4-chloro-7-(α-hydroxybenzyl)isoquinolin-1-yl)guanidine;
(4-chloro-7-(3-carboxyphenyl)isoquinolin-1-yl)guanidine;
1-guanidino-7-sulphamoylisoquinoline;
1-guanidino-7-phenylsulphamoylisoquinoline;
4-chloro-1-guanidino-7-sulphamoylisoquinoline;
4-chloro-7-cyclopentylsulphamoyl-1-guanidinoisoquinoline;
4-chloro-1-guanidino-7-(1-pyrrolidinosulphonyl)isoquinoline hydrochloride;
4-chloro-1-guanidino-7-morpholinosulphonylisoquinoline hydrochloride;
4-chloro-1-guanidino-7-[(N-methylpiperazino)sulphonyl]isoquinoline;
4-chloro-1-guanidino-7-(phenylsulphanyl)isoquinoline;
4-chloro-1-guanidino-7-(phenylsulphonyl)isoquinoline; and the salts thereof.

22. A pharmaceutical composition comprising a compound or salt according to claim 1 in admixture with a compatible adjuvant, diluent or carrier.

23. A method of treating a condition or process mediated by uPA, which comprises administering to a patient in need of said treatment an effective amount of a compound or salt according to claim 1.

24. A method according to claim 23, where the condition or process is chronic dermal ulcer angiogenesis (neovascularization), bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

25. A process for preparing a compound of formula (I):

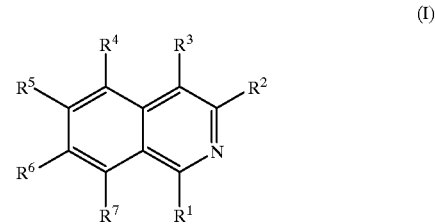

(I)

or a pharmaceutically acceptable salt thereof, wherein
one of $R^1$ and $R^2$ is H and the other is N=C(NH$_2$)$_2$ or NHC(=NH)NH$_2$,
$R^3$ is H, halogen, $C_{1-6}$ alkyl optionally substituted by one or more halogen, or $C_{1-6}$ alkoxy optionally substituted by one or more halogen,
$R^4$, $R^5$, $R^6$ and $R^7$ are each independently H, OH, halogen, $C_{1-6}$ alkyl optionally substituted by one or more substituents independently selected from halogen or OH, $C_{1-6}$ alkoxy optionally substituted by one or more halogen, CN, CO($C_{1-6}$ alkyl optionally substituted by one or more halogen), ($C_m$-alkylene)CO$_2R^8$, O($C_n$-alkylene)CO$_2R^8$, O($C_n$-alkylene)CN, ($C_n$-alkylene)CN, ($C_m$-alkylene)CONR$^9R^{10}$, ($C_m$-alkylene)NR$^9$COR$^{10}$, O($C_n$-alkylene)CONR$^9R^{10}$, ($C_m$-alkylene)NR$^9$SO$_2R^{11}$, ($C_m$-alkylene)S(O)$_pR^{11}$, ($C_m$-alkylene)SO$_2$NR$^9R^{10}$, CH=CHCOR$^8$, CH=CHCONR$^9R^{10}$, CH=CHSO$_2R^8$, CH=CHSO$_2$NR$^9R^{10}$, CH=CHSO$_2$aryl, or a group of formula X-aryl or X-het,
or, where two of $R^4$, $R^5$, $R^6$ and $R^7$ are attached to adjacent carbon atoms, they can be taken together to form an —O($C_n$-alkylene)O-moiety,
$R^8$ is H, $C_{1-6}$ alkyl optionally substituted by one or more halogen, or aryl($C_{1-6}$ alkylene),
$R^9$ and $R^{10}$ are each independently H, $C_{1-6}$ alkyl optionally substituted by one or more halogen, aryl($C_{1-6}$ alkylene), aryl, heteroaryl or heteroaryl($C_{1-6}$ alkylene), or $R^9$ and $R^{10}$ may be linked together by an alkylene moiety to form, with the atoms to which they are attached, a 4- to 7-membered ring optionally incorporating an additional hetero-group selected from an O or S atom or a NR$^{12}$ group, R is aryl, heteroaryl, or $C_{1-6}$ alkyl optionally substituted by one or more halogen, $R^{12}$ is H, $C_{1-6}$ alkyl optionally substituted by one or more halogen, or $CO(C_{1-6}$ alkyl optionally substituted by one or more halogen), X is a direct link, $C_n$-alkylene, O, $(C_n$-alkylene)O, $O(C_n$-alkylene), CH(OH), $C(C_{1-6}$ alkyl)OH, CO, $S(O)_p(C_m$-alkylene), $(C_m$-alkylene)$S(O)_p$, CH=CH, or C≡C, "aryl" is phenyl or naphthyl optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$S(O)_pR^{13}$, $(C_m$-alkylene)$SO_2NR^{14}R^{15}$, $(C_m$-alkylene)$NR^{14}SO_2R^{16}$, $CH=CHSO_2R^{13}$, $CH=CHSO_2NR^{14}R^{15}$, $CH=CHSO_2aryl^1$, $CH=CHCOR^{13}$, and $CH=CHCONR^{14}R^{15}$, "heteroaryl" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$NR^{14}SO_2R^{16}$, $(C_m$-alkylene)$S(O)_pR^{13}$, $(C_m$-alkylene)$SO_2NR^{14}R^{15}$, $CH=CHCOR^{13}$, $CH=CHCONR^{14}R^{15}$, $CH=CHSO_2R^{13}$, $CH=CHSO_2NR^{14}R^{15}$, or $CH=CHSO_2aryl^1$, "het" is an optionally benzo-fused 5- or 6-membered heterocyclic group linked to the "X" moiety by any available atom in the heterocyclic or benzo-ring (if present), which heterocyclic group is selected from dioxolyl, dioxolanyl, furyl, thienyl, pyrrolyl, oxazolyl, oxazinyl, thiazinyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, or a fully unsaturated, partially or fully saturated analogue thereof, such "het" group being optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$NR^{14}SO_2R^{16}$, $(C_m$-alkylene)$S(O)_pR^{13}$, $(C_m$-alkylene)$SO_2NR^{14}R^{15}$, $CH=CHCOR^{13}$, $CH=CHCONR^{14}R^{15}$, $CH=CHSO_2R^{13}$, $CH=CHSO_2NR^{14}R^{15}$, and $CH=CHSO_2aryl^1$, "aryl" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$, $O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$S(O)_pR^{13}$, $(C_m$-alkylene)$SO_2NR^{14}R^{15}$, $(C_m$-alkylene)$NR^{14}SO_2R^{16}$, $CH=CHSO_2R^{13}$, $CH=CHSC_2NR^{14}R^{15}$, $CH=CHCOR^{13}$, and $CH=CHCONR^{14}R^{15}$, $R^{13}$ is H, $C_{1-6}$ alkyl optionally substituted by one or more halogen, or $aryl^2(C_{1-6}$ alkylene), $R^{14}$ and $R^{15}$ are each independently H, $C_{1-6}$ alkyl optionally substituted by one or more halogen, $aryl^2(C_{1-6}$ alkylene), $aryl^2$, $heteroaryl^1$ or $heteroaryl^1(C_{1-6}$ alkylene), or $R^9$ and $R^{10}$ may be linked together by an alkylene moiety to form, with the atoms to which they are attached, a 4- to 7-membered ring optionally incorporating an additional hetero-group selected from an O or S atom or a $NR^{12}$ group, $R^{16}$ is $aryl^2$, $heteroaryl^1$, or $C_{1-6}$ alkyl optionally substituted by one or more halogen, "aryl²" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n$-alkylene)CN, $(C_n$-alkylene)CN, or $CO(C_{1-6}$ alkyl optionally substituted by one or more halogen), "heteroaryl¹" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl¹" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, $O(C_n$-alkylene)CN, $(C_n$-alkylene)CN, or $CO(C_{1-6}$ alkyl optionally substituted by one or more halogen), wherein the "C-alkylene" linking groups in the definitions above are linear or branched, and are optionally substituted by one or more ($C_{1-6}$ alkyl optionally substituted by one or more halogen) groups, m is an integer from 0 to 3, n is an integer from 1 to 3, and is an integer from 0 to 2, said process comprising:
(i) reacting a 1- or 3-aminoisoquinoline derivative (II), wherein $R^3$, $R^4$, $R^5$, $R^6$ and $R^7$ are as defined above:

(II)

[Structure: isoquinoline with R4, R3, R5, R6, R7 substituents and NH2 group]

with cyanamide ($NH_2CN$) or another reagent which acts as a "$NHC^+=NH$" synthon; or (ii) reacting a 1- or 3-aminoisoquinoline derivative (II) as defined above with a reagent which acts as a protected amidine(2+) synthon (IV):

$$PNH \overset{2+}{\frown} NHP_1 \quad (IV)$$

where P and $P_1$ are N-protecting groups, via formation of a compound of formula (V) or salt thereof, wherein $R^3$, $R^4$, $R^5$, $R^6$ and $R^7$ are as defined above:

(V)

[Structure: isoquinoline with R4, R3, R5, R6, R7 substituents and =N-CH(NHP1)(PNH) group]

and deprotection thereof; or (iii) reacting a compound of formula (VI):

(VI)

[Structure: isoquinoline with R4, R3, R5, R6, R7 substituents and Z group]

wherein $R^3$, $R^4$, $R^5$, $R^6$ and $R^7$ are as defined above and where Z is attached at the 1- or 3-position and is a leaving group, by displacing the leaving group by the free base of guanidine.

26. A compound of formula (V)

(V)

[Structure: isoquinoline with R4, R3, R5, R6, R7 substituents and =N-CH(NHP1)(PNH) group]

wherein $R^3$ is H, halogen, $C_{1-6}$ alkyl optionally substituted by one or more halogen, or $C_{1-6}$ alkoxy optionally substituted by one or more halogen, $R^4$, $R^5$, $R^6$ and $R^7$ are each independently H, OH, halogen, $C_{1-6}$ alkyl optionally substituted by one or more substituents independently selected from halogen or OH, $C_{1-6}$ alkoxy optionally substituted by one or more halogen, CN, $CO(C_{1-6}$ alkyl optionally substituted by one or more halogen), $(C_m$-alkylene)$CO_2R^8$, $O(C_n$-alkylene)$CO_2R^8$, $O(C_n$-alkylene)CN, $(C_n$-alkylene)CN,$(C_m$-alkylene)$CONR^9R^{10}$, $(C_m$-alkylene)$NR^9COR^{10}$, $O(C_n$-alkylene)$CONR^9R^{10}$, $(C_m$-alkylene)$NR^9SO_2R^{11}$, $(C_m$-alkylene)$S(O)_pR^{11}$, $(C_m$-alkylene)$SO_2NR^9R^{10}$, CH=$CHCOR^8$, CH=$CHCONR^9R^{10}$, CH=$CHSO_2R^8$, CH=$CHSO_2NR^9R^{10}$, CH=$CHSO_2$aryl, or a group of formula X-aryl or X-het, or, where two of $R^4$, $R^5$, $R^6$ and $R^7$ are attached to adjacent carbon atoms, they can be taken together to form an —$O(C_n$-alkylene)O—moiety, $R^8$ is H, $C_{1-6}$ alkyl optionally substituted by one or more halogen, or aryl($C_{1-6}$ alkylene), $R^9$ and $R^{10}$ are each independently H, $C_{1-6}$ alkyl optionally substituted by one or more halogen, aryl($C_{1-6}$ alkylene), aryl, heteroaryl or heteroaryl($C_{1-6}$ alkylene), or $R^9$ and $R^{10}$ may be linked together by an alkylene moiety to form, with the atoms to which they are attached, a 4- to 7-membered ring optionally incorporating an additional hetero-group selected from an O or S atom or a $NR^{12}$ group, $R^{11}$ is aryl, heteroaryl, or $C_{1-6}$ alkyl optionally substituted by one or more halogen, $R^{12}$ is H, $C_{1-6}$ alkyl optionally substituted by one or more halogen, or $CO(C_{1-6}$ alkyl optionally substituted by one or more halogen), X is a direct link, $C_n$-alkylene, O, $(C_n$-alkylene)O, $O(C_n$-alkylene), CH(OH), C($C_{1-6}$ alkyl)OH, CO, $S(O)_p(C_m$-alkylene), $(C_m$-alkylene)$S(O)_p$, CH=CH, or C≡C, "aryl" is phenyl or naphthyl optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, $O(C_n$-alkylene)CN, $(C_n$-alkylene)CN, $CO(C_{1-6}$ alkyl optionally substituted by one or more halogen), $(C_m$-alkylene)$CO_2R^{13}$,$O(C_n$-alkylene)$CO_2R^{13}$, $(C_m$-alkylene)$CONR^{14}R^{15}$, $(C_m$-alkylene)$NR^{14}COR^{15}$, $O(C_n$-alkylene)$CONR^{14}R^{15}$, $(C_m$-alkylene)$S(O)_pR^{13}$, $(C_m$-alkylene)$SO_2NR^{14}R^{15}$, $(C_m$-alkylene)$NR^{14}SO_2R^{16}$, CH=$CHSO_2R^{13}$, CH=$CHSO_2NR^{14}R^{15}$, CH=$CHSO_2$aryl$^1$, CH=$CHCOR^{13}$, and CH=$CHCONR^{14}R^{15}$, "heteroaryl" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, O($C_n$-alkylene)CN, ($C_n$-alkylene)CN, CO($C_{1-6}$ alkyl optionally substituted by one or more halogen), ($C_m$-alkylene)CO$_2$R$^{13}$, O($C_n$-alkylene)CO$_2$R$^{13}$, ($C_m$-alkylene)CONR$^{14}$R$^{15}$, ($C_m$-alkylene)NR$^{14}$COR$^{15}$, O($C_n$-alkylene)CONR$^{14}$R$^{15}$, ($C_m$-alkylene)NR$^{14}$SO$_2$R$^{16}$, ($C_m$-alkylene)S(O)$_p$R$^{13}$, ($C_m$-alkylene)SO$_2$NR$^{14}$R$^{15}$, CH=CHCOR$^{13}$, CH=CHCONR$^{14}$R$^{15}$, CH=CHSO$_2$R$^{13}$, CH=CHSO$_2$NR$^{14}$R$^{15}$, or CH=CHSO$_2$aryl$^1$, "het" is an optionally benzo-fused 5- or 6-membered heterocyclic group linked to the "X" moiety by any available atom in the heterocyclic or benzo-ring (if present), which heterocyclic group is selected from dioxolyl, dioxolanyl, furyl, thienyl, pyrrolyl, oxazolyl, oxazinyl, thiazinyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, or a fully unsaturated, partially or fully saturated analogue thereof, such "het" group being optionally substituted by one or more substituents independently selected from halogen, $C_{1-6}$ alkyl optionally substituted by one or more substituents independently selected from halogen and OH, $C_{1-6}$ alkoxy optionally substituted by one or more halogen, CN, O($C_n$-alkylene)CN, ($C_n$-alkylene)CN, CO($C_{1-6}$ alkyl optionally substituted by one or more halogen), ($C_m$-alkylene)CO$_2$R$^{13}$, O($C_n$-alkylene)CO$_2$R$^{13}$, ($C_m$-alkylene)CONR$^{14}$R$^{15}$, ($C_m$-alkylene)NR$^{14}$COR$^{15}$, O($C_n$-alkylene)CONR$^{14}$R$^{15}$, ($C_m$-alkylene)NR$^{14}$SO$_2$R$^{16}$, ($C_m$-alkylene)S(O)$_p$R$^{13}$, ($C_m$-alkylene)SO$_2$NR$^{14}$R$^{15}$, CH=CHCOR$^{13}$, CH=CHCONR$^{14}$R$^{15}$, CH=CHSO$_2$R$^{13}$, CH=CHSO$_2$NR$^{14}$R$^{15}$, and CH=CHSO$_2$aryl$^1$, "aryl$^1$" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, O($C_n$-alkylene)CN, ($C_n$-alkylene)CN, CO($C_{1-6}$ alkyl optionally substituted by one or more halogen), ($C_m$-alkylene)CO$_2$R$^{13}$, O($C_n$-alkylene)CO$_2$R$^{13}$, ($C_m$-alkylene)CONR$^{14}$R$^{15}$, ($C_m$-alkylene)NR$^{14}$COR$^{15}$, O($C_n$-alkylene)CONR$^{14}$R$^{15}$, ($C_m$-alkylene)S(O)$_p$R$^{13}$, ($C_m$-alkylene)SO$_2$NR$^{14}$R$^{15}$, ($C_m$-alkylene)NR$^{14}$SO$_2$R$^{16}$, CH=CHSO$_2$R$^{13}$, CH=CHSO$_2$NR$^{14}$R$^{15}$, CH=CHCOR$^{13}$, and CH=CHCONR$^{14}$R$^{15}$, R$^{13}$ is H, $C_{1-6}$ alkyl optionally substituted by one or more halogen, or aryl$^2$($C_{1-6}$ alkylene), R$^{14}$ and R$^{15}$ are each independently H, $C_{1-6}$ alkyl optionally substituted by one or more halogen, aryl$^2$($C_{1-6}$ alkylene), aryl$^2$, heteroaryl$^1$ or heteroaryl$^1$($C_{1-6}$ alkylene), or R$^9$ and R$^{10}$ may be linked together by an alkylene moiety to form, with the atoms to which they are attached, a 4- to 7-membered ring optionally incorporating an additional hetero-group selected from an O or S atom or a NR$^{12}$ group, R$^{16}$ is aryl$^2$, heteroaryl$^1$, or $C_{1-6}$ alkyl optionally substituted by one or more halogen, "aryl$^2$" is phenyl or naphthyl optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, O($C_n$-alkylene)CN, ($C_n$-alkylene)CN, or CO($C_{1-6}$ alkyl optionally substituted by one or more halogen), "heteroaryl$^1$" is an optionally benzo-fused 5- or 6-membered heterocyclic group linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl and pyranyl, said "heteroaryl$^1$" group being optionally substituted by one or more substituents independently selected from halogen, $C_{1-6}$ alkyl optionally substituted by one or more substituents independently selected from halogen or OH, $C_{1-6}$ alkoxy optionally substituted by one or more halogen, CN, O($C_n$-alkylene)CN, ($C_n$-alkylene)CN, or CO($C_{1-6}$ alkyl optionally substituted by one or more halogen), wherein the "C-alkylene" linking groups in the definitions above are linear or branched, and are optionally substituted by one or more ($C_{1-6}$ alkyl optionally substituted by one or more halogen) groups, m is an integer from 0 to 3, n is an integer from 1 to 3, p is an integer from 0 to 2, and P and P$_1$ are the same or different N-protecting groups.

27. The compound of claim 26, wherein the N-protecting groups are selected from the group consisting of t-butoxycarbonyl, benzyloxycarbonyl and arylsulphonyl.

\* \* \* \* \*